US009793488B2

(12) United States Patent
Park et al.

(10) Patent No.: US 9,793,488 B2
(45) Date of Patent: Oct. 17, 2017

(54) COMPOUND FOR ORGANIC OPTOELECTRONIC ELEMENT, ORGANIC LIGHT-EMITTING ELEMENT COMPRISING SAME, AND DISPLAY DEVICE COMPRISING THE ORGANIC LIGHT-EMITTING ELEMENT

(71) Applicant: CHEIL INDUSTRIES INC., Gyeongsangbuk-do (KR)

(72) Inventors: Moo-Jin Park, Uiwang-si (KR); Eun-Sun Yu, Uiwang-si (KR); Ho-Jae Lee, Uiwang-si (KR); Mi-Young Chae, Uiwang-si (KR)

(73) Assignee: CHEIL INDUSTRIES, INC., Gumi-Si, Gyeongsangbuk-Do (KR)

( * ) Notice: Subject to any disclaimer, the term of this patent is extended or adjusted under 35 U.S.C. 154(b) by 716 days.

(21) Appl. No.: 14/359,786

(22) PCT Filed: Dec. 17, 2012

(86) PCT No.: PCT/KR2012/011023
§ 371 (c)(1),
(2) Date: May 21, 2014

(87) PCT Pub. No.: WO2013/100465
PCT Pub. Date: Jul. 4, 2013

(65) Prior Publication Data
US 2014/0326984 A1 Nov. 6, 2014

(30) Foreign Application Priority Data

Dec. 29, 2011 (KR) .................. 10-2011-0146193

(51) Int. Cl.
*H01L 51/54* (2006.01)
*C09K 11/06* (2006.01)
*H01L 51/00* (2006.01)
*C07D 417/14* (2006.01)
*C07D 417/10* (2006.01)
*C07D 417/12* (2006.01)
(Continued)

(52) U.S. Cl.
CPC ........ *H01L 51/0054* (2013.01); *C07D 417/10* (2013.01); *C07D 417/12* (2013.01); *C07D 417/14* (2013.01); *C07D 487/04* (2013.01); *C09K 11/06* (2013.01); *H01L 51/0061* (2013.01); *H01L 51/0071* (2013.01); *H01L 51/0072* (2013.01); *H01L 51/0073* (2013.01); *C09K 2211/1007* (2013.01); *C09K 2211/1011* (2013.01); *C09K 2211/1029* (2013.01); *C09K 2211/1037* (2013.01); *C09K 2211/1088* (2013.01); *C09K 2211/1092* (2013.01); *H01L 51/0081* (2013.01); *H01L 51/0085* (2013.01); *H01L 51/5012* (2013.01); *H01L 51/5056* (2013.01); *H01L 51/5072* (2013.01); *H01L 51/5092* (2013.01); *H01L 51/5096* (2013.01); *H01L 2251/308* (2013.01); *Y02E 10/549* (2013.01)

(58) Field of Classification Search
CPC .. C07D 417/00; C07D 417/02; C07D 417/10; C07D 417/12; C07D 417/14; C07D 487/00; C07D 487/02; C07D 487/04; C07D 209/82; C09K 11/06; C09K 2211/00; C09K 2211/10; C09K 2211/1007; C09K 2211/1011; C09K 2211/1029; C09K 2211/1037; C09K 2211/1088; C09K 2211/1092; Y02E 10/549; H01L 51/0032; H01L 51/005; H01L 51/0054; H01L 51/0061; H01L 51/0071; H01L 51/0072; H01L 51/0073; H01L 51/0081; H01L 51/0085; H01L 51/50; H01L 51/5012; H01L 51/5056; H01L 51/5072; H01L 51/5092; H01L 51/5096; H01L 2251/308
USPC ....... 428/690, 691, 917, 411.4, 336; 427/58, 427/66; 313/500–512; 257/40, 88–104, 257/E51.001–E51.052; 252/301.16–301.35; 548/159
See application file for complete search history.

(56) References Cited

U.S. PATENT DOCUMENTS

2006/0125380 A1* 6/2006 Nagara ............... H01L 51/5016
313/504
2008/0124572 A1* 5/2008 Mizuki ................. C07C 211/54
428/690
(Continued)

FOREIGN PATENT DOCUMENTS

DE WO 2010136109 A1 * 12/2010 ........... C07D 209/82
JP 2004-067658 A 3/2004
(Continued)

OTHER PUBLICATIONS

Machine translation of JP2004-067658. Date of publication: Mar. 4, 2004.*

(Continued)

*Primary Examiner* — Andrew K Bohaty
(74) *Attorney, Agent, or Firm* — Lee & Morse, P.C.

(57) ABSTRACT

Disclosed are a compound for an organic optoelectronic device, an organic light emitting diode including the same, and a display device including the organic light emitting diode. The compound for an organic optoelectronic device represented by the following Chemical Formula 1 provides an organic light emitting diode having life-span characteristics due to excellent electrochemical and thermal stability, and high luminous efficiency at a low driving voltage.

19 Claims, 3 Drawing Sheets

(51) Int. Cl.
*C07D 487/04* (2006.01)
*H01L 51/50* (2006.01)

(56) References Cited

U.S. PATENT DOCUMENTS

| | | | | |
|---|---|---|---|---|
| 2010/0200054 A1* | 8/2010 | Jung | ............ | C09K 11/06 |
| | | | | 136/256 |
| 2011/0315975 A1* | 12/2011 | Kai | ............ | C07D 487/04 |
| | | | | 257/40 |
| 2012/0068170 A1* | 3/2012 | Pflumm | ............ | C07D 209/82 |
| | | | | 257/40 |
| 2012/0133274 A1* | 5/2012 | Kawakami | ............ | C07D 405/14 |
| | | | | 313/504 |

FOREIGN PATENT DOCUMENTS

| | | | |
|---|---|---|---|
| JP | WO 2010113726 A1 * | 10/2010 | ........... C07D 487/04 |
| KR | 10-2006-0045360 A | 5/2006 | |
| KR | 10-2009-0119739 A | 11/2009 | |
| KR | 10-2010-0002153 A | 1/2010 | |
| KR | 10-2010-0029040 A | 3/2010 | |
| KR | 10-2011-0015836 A | 2/2011 | |
| KR | 20110043270 A * | 4/2011 | |
| WO | WO-2010/041872 A2 | 4/2010 | |
| WO | WO-2011/132683 A1 | 10/2011 | |

OTHER PUBLICATIONS

Machine translation of KR2011-0043270. Date of publication: Apr. 27, 2011.*

* cited by examiner

COMPOUND FOR ORGANIC OPTOELECTRONIC ELEMENT, ORGANIC LIGHT-EMITTING ELEMENT COMPRISING SAME, AND DISPLAY DEVICE COMPRISING THE ORGANIC LIGHT-EMITTING ELEMENT

TECHNICAL FIELD

A compound for an organic optoelectronic device being capable of providing an organic optoelectronic device having excellent life-span, efficiency, electrochemical stability, and thermal stability, an organic light emitting diode including the compound, and a display device including the organic light emitting diode are disclosed.

BACKGROUND ART

An organic optoelectronic device is a device requiring a charge exchange between an electrode and an organic material by using holes or electrons.

An organic optoelectronic device may be classified as follows in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (a voltage source).

A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

Examples of an organic optoelectronic device include an organic photoelectric device, an organic light emitting diode, an organic solar cell, an organic photo conductor drum, an organic transistor, and the like, which require a hole injecting or transport material, an electron injecting or transport material, or a light emitting material.

Particularly, an organic light emitting diode (OLED) has recently drawn attention due to an increase in demand for flat panel displays. In general, organic light emission refers to conversion of electrical energy into photo-energy.

Such an organic light emitting diode converts electrical energy into light by applying current to an organic light emitting material. It has a structure in which a functional organic material layer is interposed between an anode and a cathode. The organic material layer includes a multi-layer including different materials, for example a hole injection layer, a hole transport layer, an emission layer, an electron transport layer, and an electron injection layer, in order to improve efficiency and stability of an organic light emitting diode.

In such an organic light emitting diode, when a voltage is applied between an anode and a cathode, holes from the anode and electrons from the cathode are injected to an organic material layer and recombined to generate excitons having high energy. The generated excitons generate light having certain wavelengths while shifting to a ground state.

Recently, it has become known that a phosphorescent light emitting material may be used for a light emitting material of an organic light emitting diode in addition to the fluorescent light emitting material. Such a phosphorescent material emits lights by transporting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material, for example a hole injection material, a hole transport material, an electron transport material, an electron injection material, and the like.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength or color purity decreases because of interactions between molecules, or device efficiency decreases because of a light emitting quenching effect. Therefore, a host/dopant system is included as a light emitting material in order to improve color purity and increase luminous efficiency and stability through energy transfer.

In order to implement excellent performance of an organic light emitting diode, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming material for an organic light emitting diode has thus far not been satisfactory and thus there is a need for a novel material. This material development is also required for other organic optoelectronic devices.

The low molecular organic light emitting diode is manufactured as a thin film in a vacuum deposition method and can have good efficiency and life-span performance. A polymer organic light emitting diode is manufactured in an inkjet or spin coating method has an advantage of low initial cost and being large-sized.

Both low molecular organic light emitting and polymer organic light emitting diodes have an advantage of self-light emitting, high speed response, wide viewing angle, ultra-thin, high image quality, durability, large driving temperature range, and the like. In particular, they have good visibility due to self-light emitting characteristics compared with a conventional LCD (liquid crystal display) and have an advantage of decreasing thickness and weight of LCD up to a third, because they do not need a backlight.

In addition, since they have a response speed 1000 time faster microsecond unit than LCD, they can realize a perfect motion picture without after-image. Based on these advantages, they have been remarkably developed to have 80 times efficiency and more than 100 times life-span since they come out for the first time in the late 1980s. Recently, they keep being rapidly larger such as a 40-inch organic light emitting diode panel.

They are simultaneously required to have improved luminous efficiency and life-span in order to be larger. Herein, their luminous efficiency need smooth combination between holes and electrons in an emission layer. However, since an organic material in general has slower electron mobility than hole mobility, it has a drawback of inefficient combination between holes and electrons. Accordingly, while increasing electron injection and mobility from a cathode and simultaneously preventing movement of holes is required.

In order to improve life-span, a material crystallization caused by Joule heats generated during device operating is required to be prevented. Accordingly, there has been a strong need for an organic compound having excellent electron injection and mobility, and high electrochemical stability.

DISCLOSURE

Technical Problem

A compound for an organic optoelectronic device that may act as a hole injection and transport material or an electron injection and transport material, and also act as a light emitting host along with an appropriate dopant is provided.

An organic light emitting diode having excellent life-span, efficiency, driving voltage, electrochemical stability, and thermal stability and a display device including the same are provided.

Technical Solution

In one embodiment of the present invention, a compound for an organic optoelectronic device represented by the following Chemical Formula 1 is provided.

[Chemical Formula 1]

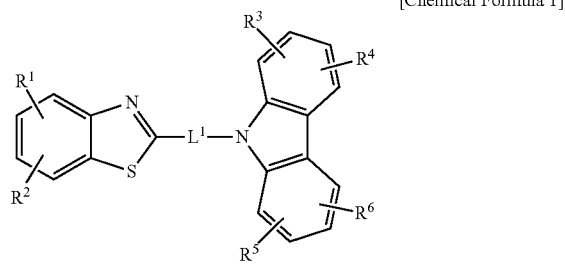

In the above Chemical Formula 1, $L^1$ is a substituted or unsubstituted C6 to C30 arylene group or a substituted or unsubstituted C2 to C30 heteroarylene group, $R^1$ and $R^2$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, $R^3$ to $R^6$ are independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof, and the $R^3$ and $R^4$ are fused to form a ring.

The compound for an organic optoelectronic device represented by the above Chemical Formula 1 may be represented by the following Chemical Formula 2.

[Chemical Formula 2]

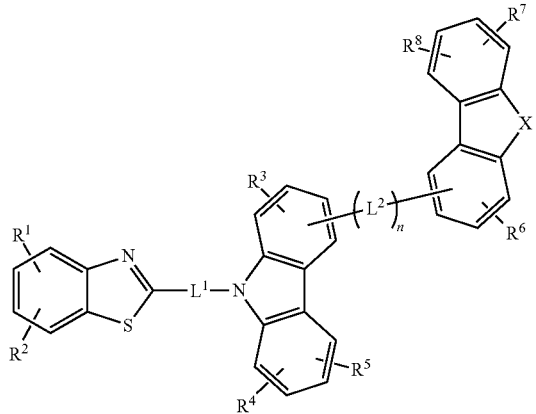

In the above Chemical Formula 2, $L^1$ and $L^2$ are independently a substituted or unsubstituted C6 to C30 arylene group or a substituted or unsubstituted C2 to C30 heteroarylene group, n is an integer ranging from 0 to 3, $R^1$ to $R^8$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, X is —$NR^9$—, —O—, —S— or —$CR^{10}R^{11}$—, wherein the $R^9$ to $R^{11}$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, $R^{10}$ and $R^{11}$ are fused to each other to provide a ring.

The compound for an organic optoelectronic device represented by the above Chemical Formula 1 may be represented by the following Chemical Formula 3.

[Chemical Formula 3]

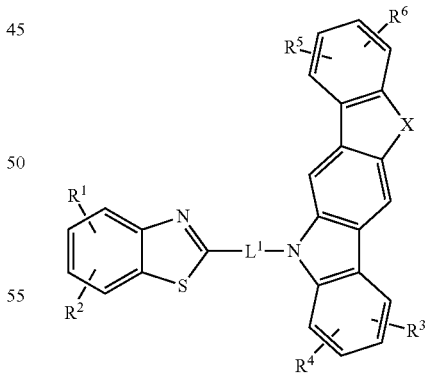

In the above Chemical Formula 3, $L^1$ is a substituted or unsubstituted C6 to C30 arylene group or a substituted or unsubstituted C2 to C30 heteroarylene group, $R^1$ to $R^6$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, X is —$NR^7$—, —O—, —S— or —$CR^8R^9$—, wherein the $R^7$ to $R^9$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, or $R^8$ and $R^9$ are fused to each other to provide a ring.

The compound for an organic optoelectronic device represented by the above Chemical Formula 1 may be represented by the following Chemical Formula 4.

[Chemical Formula 4]

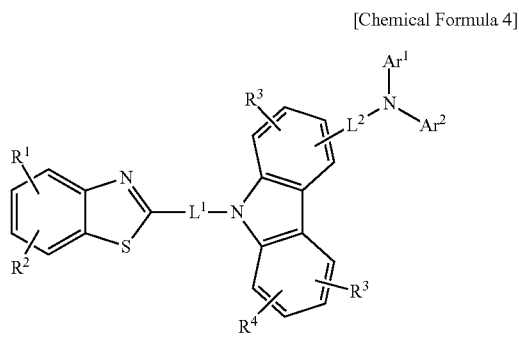

In the above Chemical Formula 4, $L^1$ and $L^2$ are independently a substituted or unsubstituted C6 to C30 arylene group or a substituted or unsubstituted C2 to C30 heteroarylene group, $R^1$ to $R^5$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, $Ar^1$ and $Ar^2$ are independently a substituted or unsubstituted C1 to C10 alkyl group, a substituted or unsubstituted C6 to C30 aryl group, a substituted or unsubstituted C2 to C30 heteroaryl group, or a combination thereof.

The compound for an organic optoelectronic device represented by the above Chemical Formula 1 may be represented by the following Chemical Formula 5.

[Chemical Formula 5]

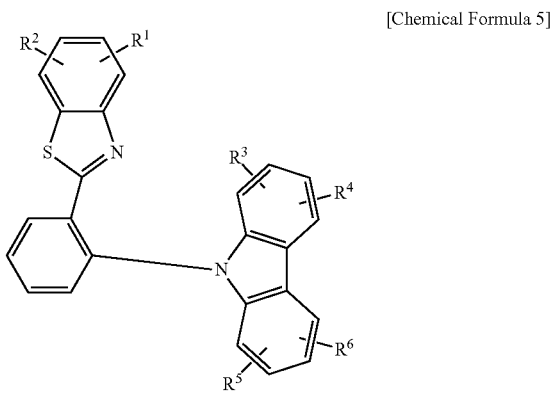

In the above Chemical Formula 5, $R^1$ and $R^2$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, $R^3$ to $R^6$ are independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof, or the $R^3$ and $R^4$ are fused to each other to provide a ring.

The compound for an organic optoelectronic device represented by the above Chemical Formula 1 may be represented by the following Chemical Formula 6.

[Chemical Formula 6]

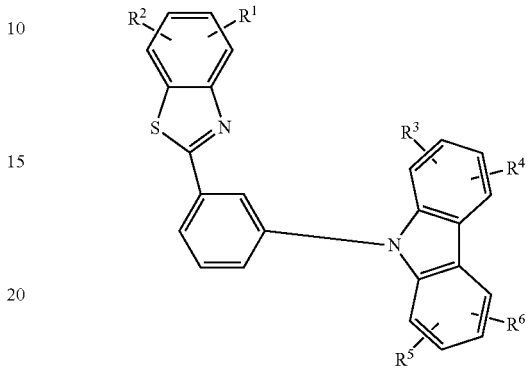

In the above Chemical Formula 6, $R^1$ and $R^2$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, $R^3$ to $R^6$ are independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof, or the $R^3$ and $R^4$ are fused to each other to provide a ring.

The compound for an organic optoelectronic device represented by the above Chemical Formula 1 may be represented by the following Chemical Formula 7.

[Chemical Formula 7]

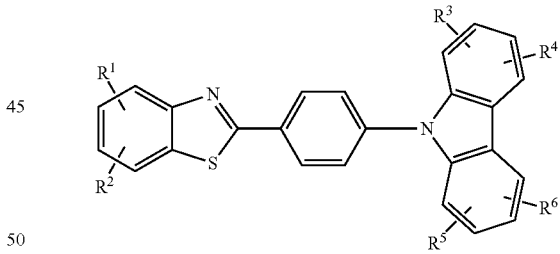

In the above Chemical Formula 7, $R^1$ and $R^2$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, $R^3$ to $R^6$ are independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof, or the $R^3$ and $R^4$ are fused to each other to provide a ring.

The $L^1$ may be a substituted or unsubstituted phenylene group or a substituted or unsubstituted naphthylene group.

The compound for an organic optoelectronic device may be one of compounds represented by the following Chemical Formulae A-1 to A-74.

[Chemical Formula A-1]
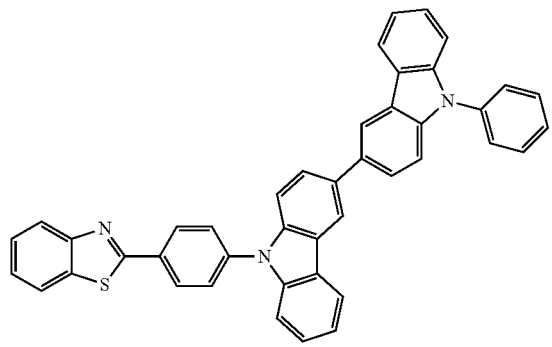
[Chemical Formula A-2]
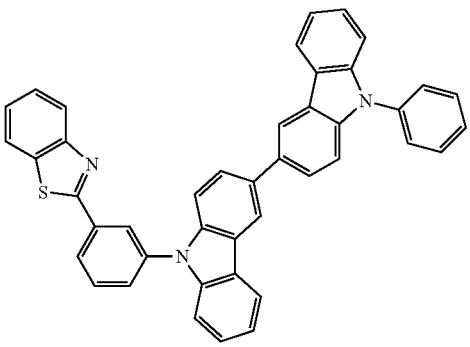
[Chemical Formula A-3]
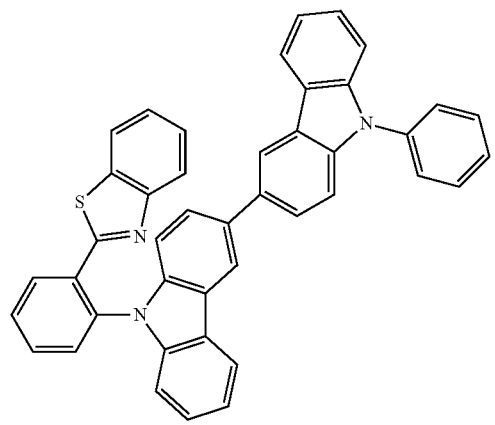
[Chemical Formula A-4]
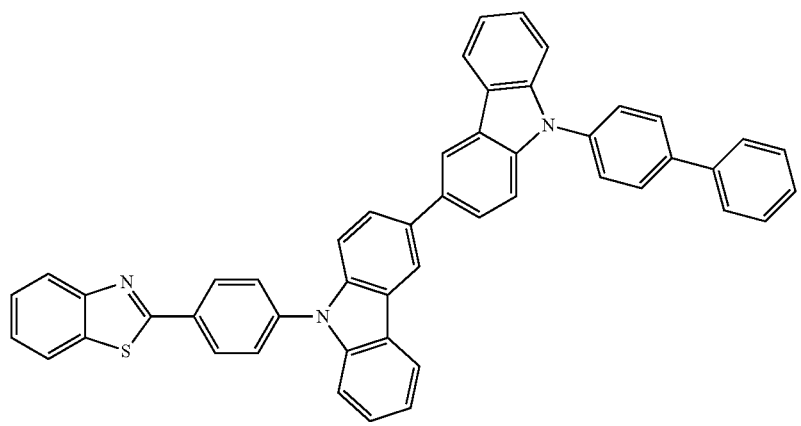
[Chemical Formula A-5]
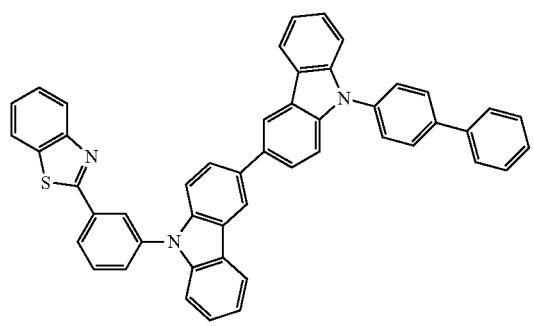
[Chemical Formula A-6]
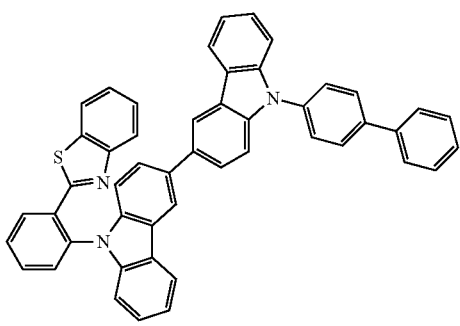

-continued
[Chemical Formula A-7]
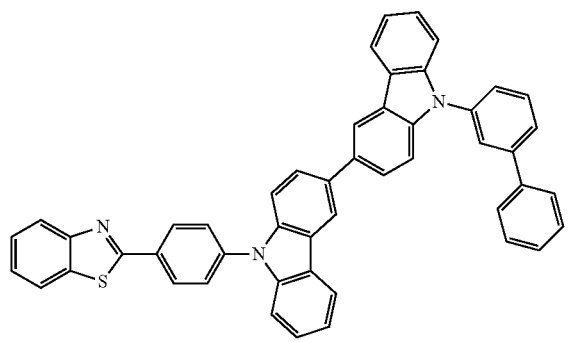
[Chemical Formula A-8]
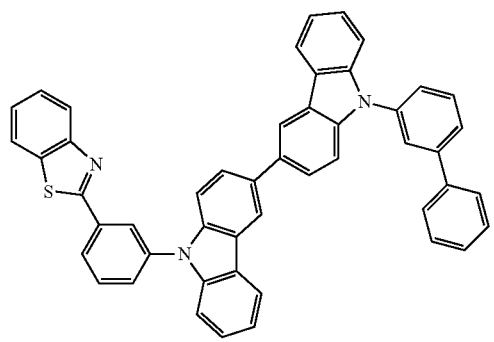
[Chemical Formula A-9]
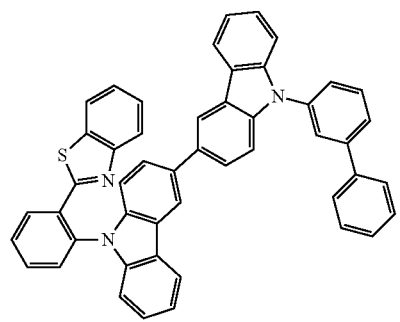
[Chemical Formula A-10]
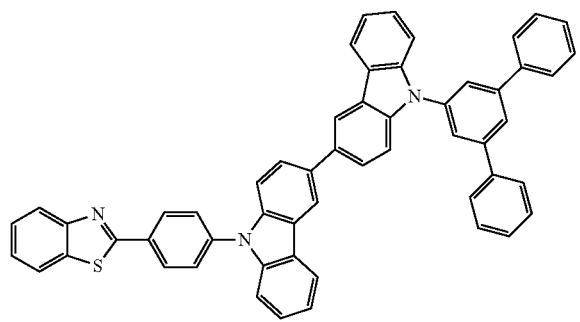
[Chemical Formula A-11]
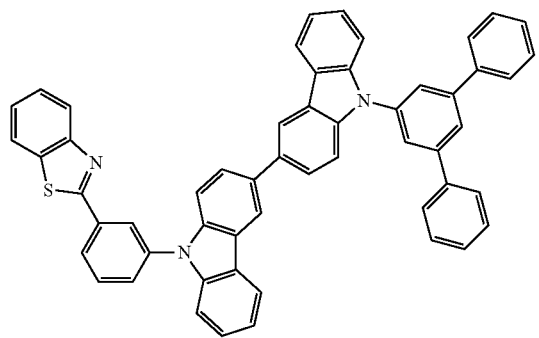
[Chemical Formula A-12]
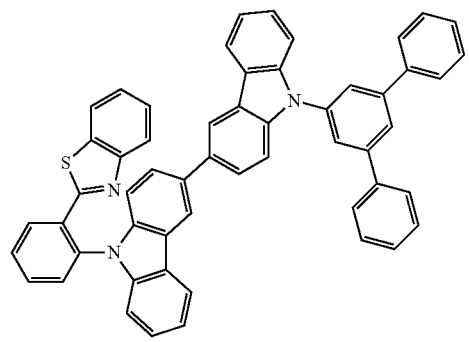
[Chemical Formula A-13]
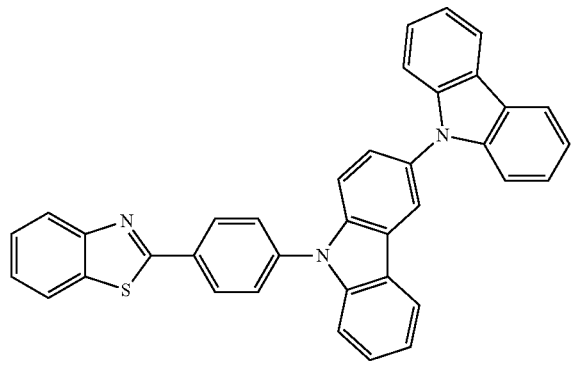
[Chemical Formula A-14]
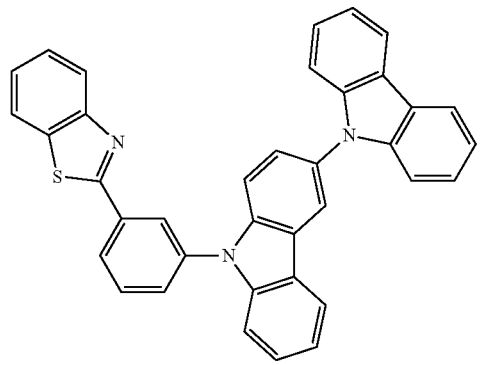

[Chemical Formula A-15]
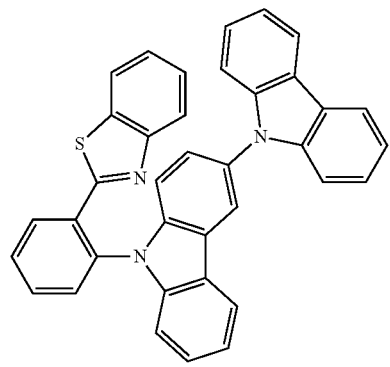
[Chemical Formula A-16]
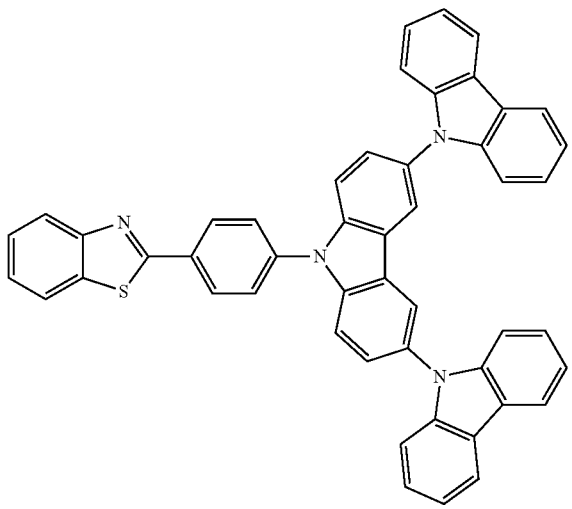
[Chemical Formula A-17]
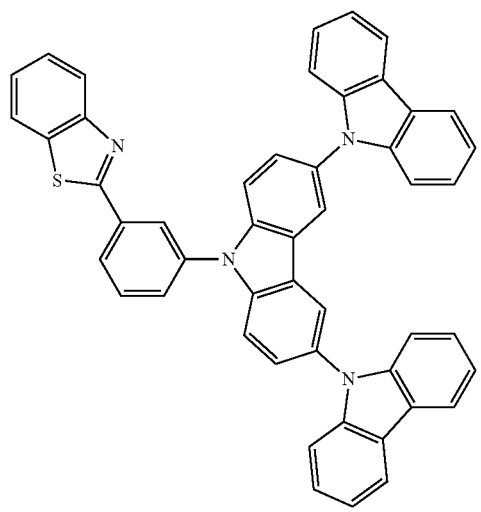
[Chemical Formula A-18]
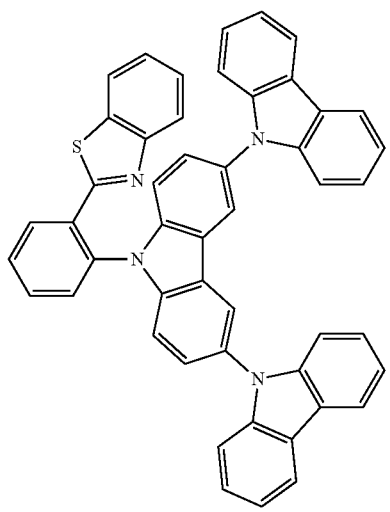
[Chemical Formula A-19]
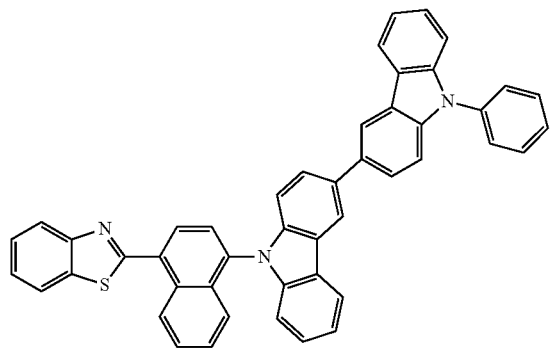
[Chemical Formula A-20]
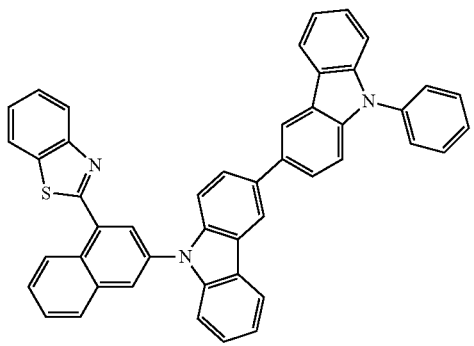

[Chemical Formula A-21]
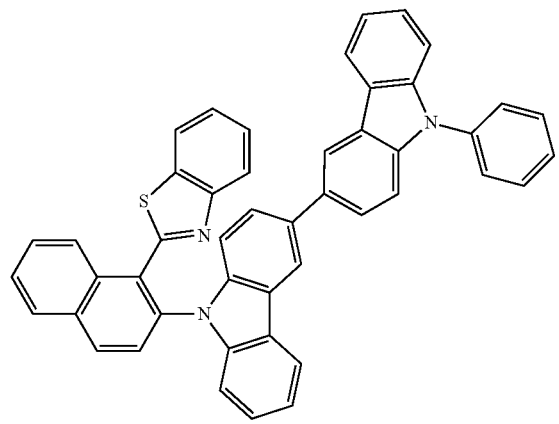
[Chemical Formula A-22]
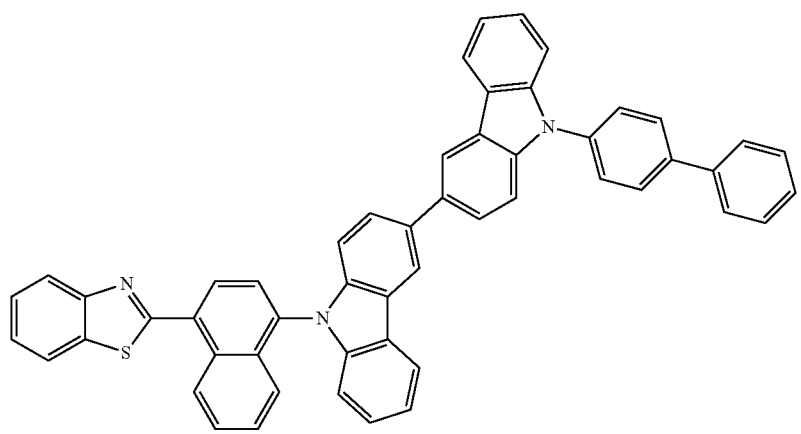
[Chemical Formula A-23]
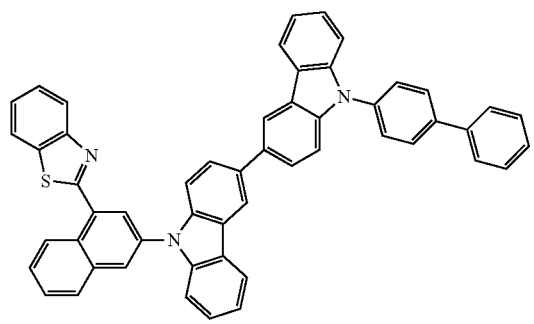
[Chemical Formula A-24]
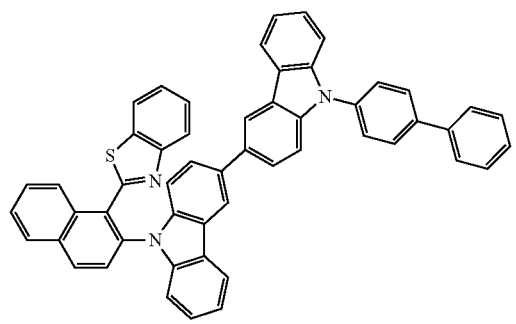
[Chemical Formula A-25]
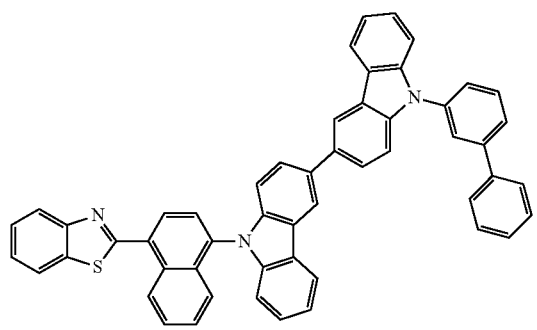
[Chemical Formula A-26]
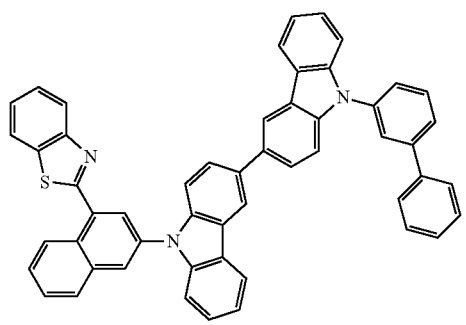

-continued
[Chemical Formula A-27]
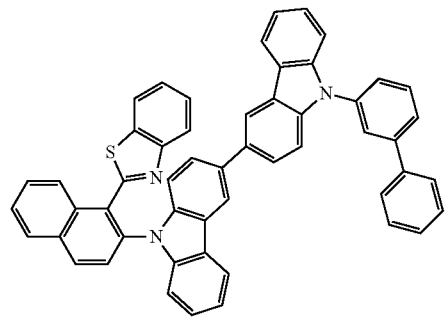
[Chemical Formula A-28]
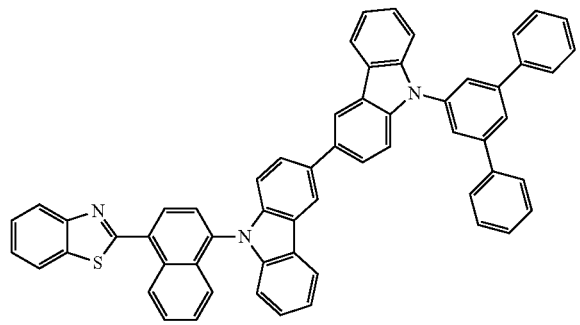
[Chemical Formula A-29]
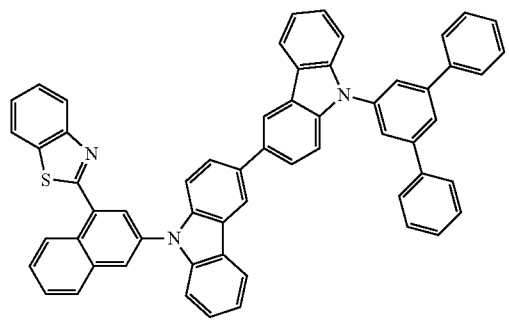
[Chemical Formula A-30]
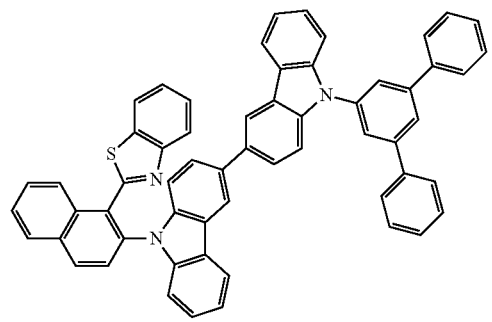
[Chemical Formula A-31]
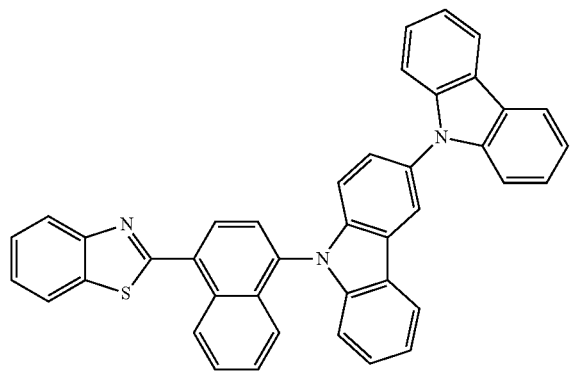
[Chemical Formula A-32]
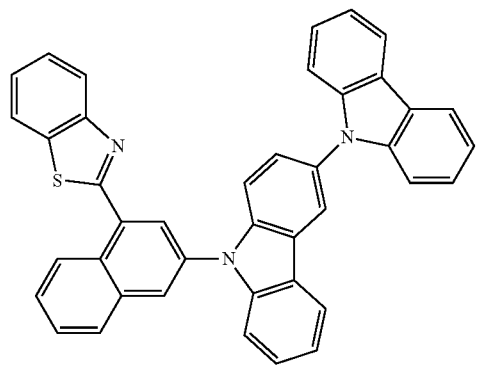
[Chemical Formula A-33]
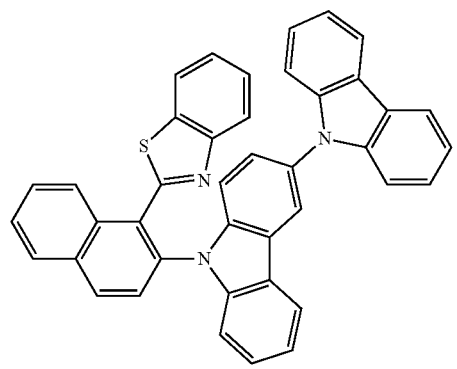
[Chemical Formula A-34]
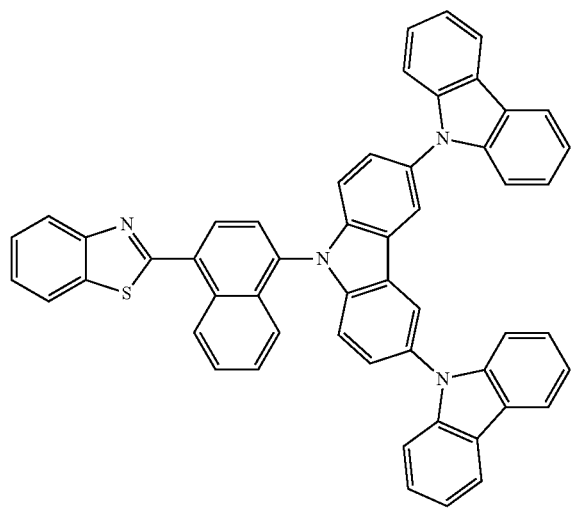

-continued
[Chemical Formula A-35]
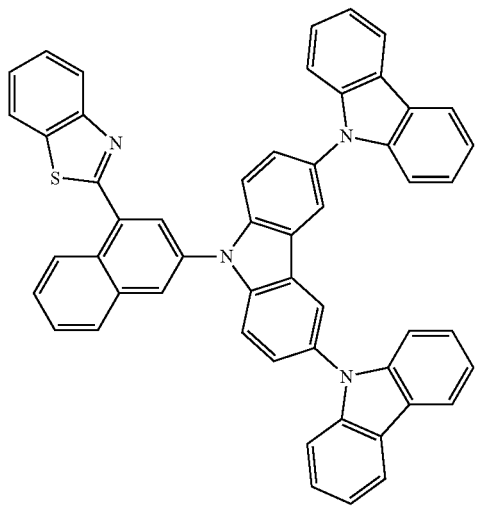
[Chemical Formula A-36]
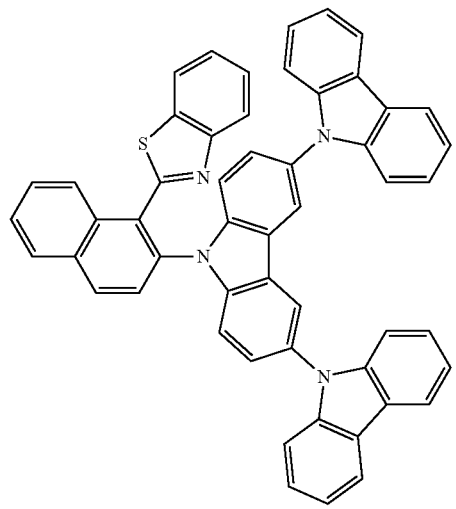
[Chemical Formula A-37]
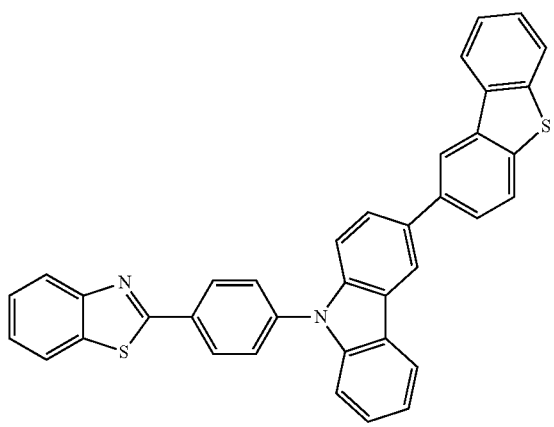
[Chemical Formula A-38]
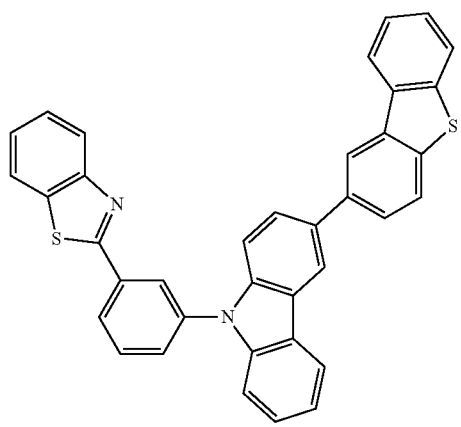
[Chemical Formula A-39]
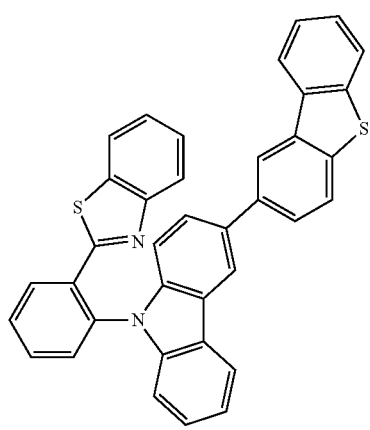
[Chemical Formula A-40]
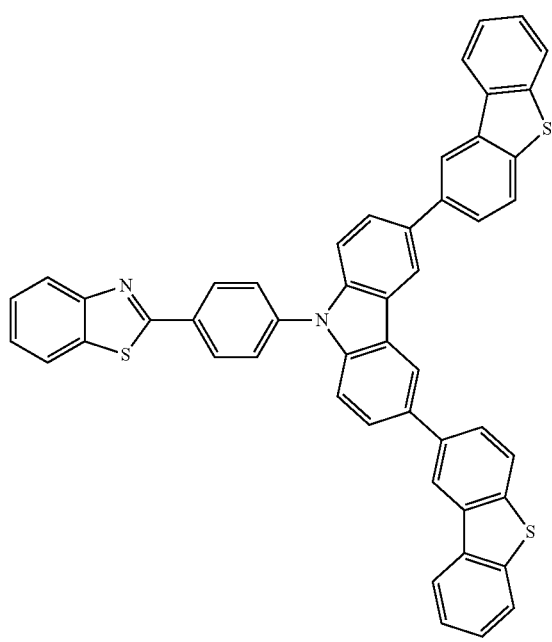

[Chemical Formula A-41]
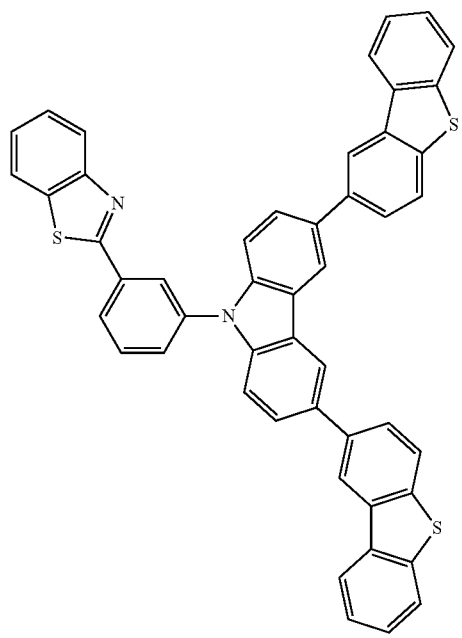
[Chemical Formula A-42]
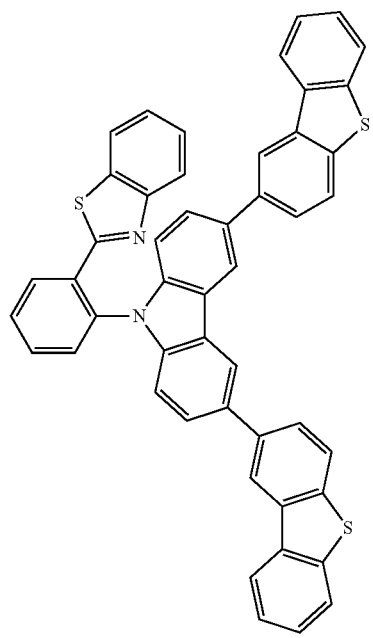
[Chemical Formula A-43]
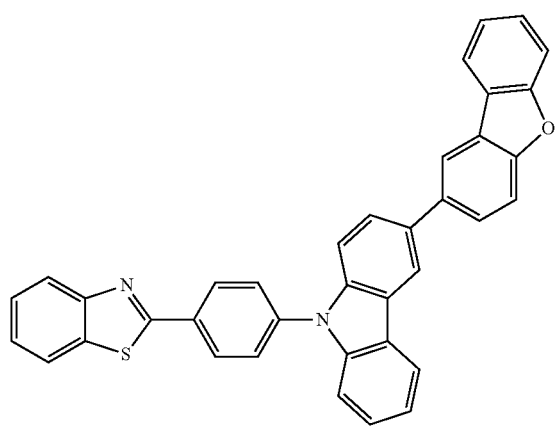
[Chemical Formula A-44]
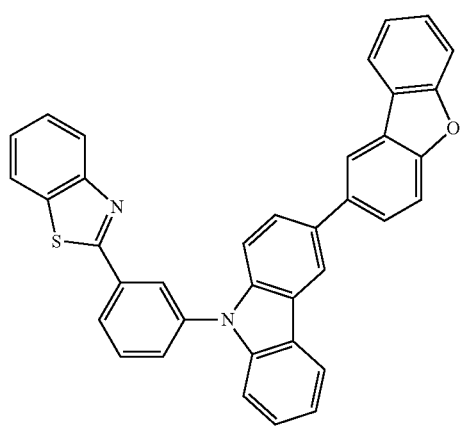

-continued
[Chemical Formula A-45]
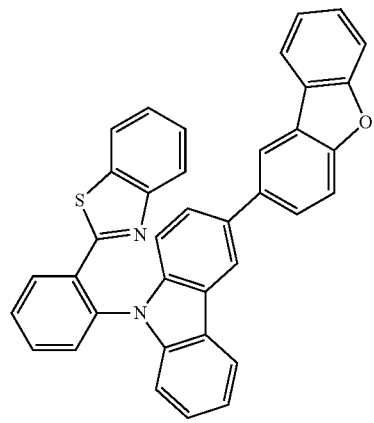
[Chemical Formula A-46]
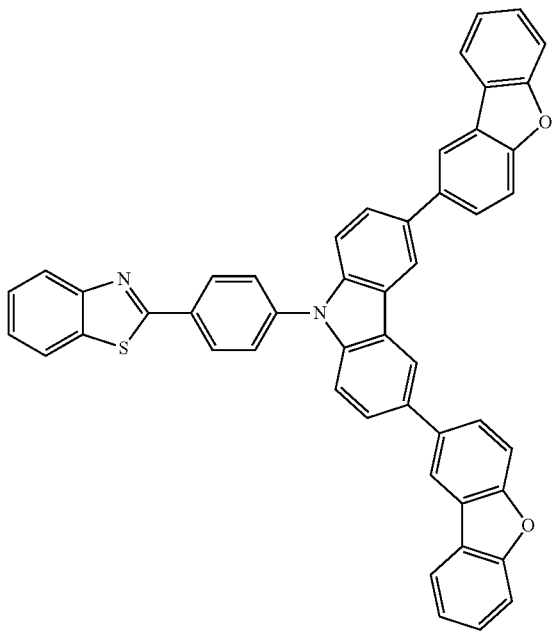
[Chemical Formula A-47]
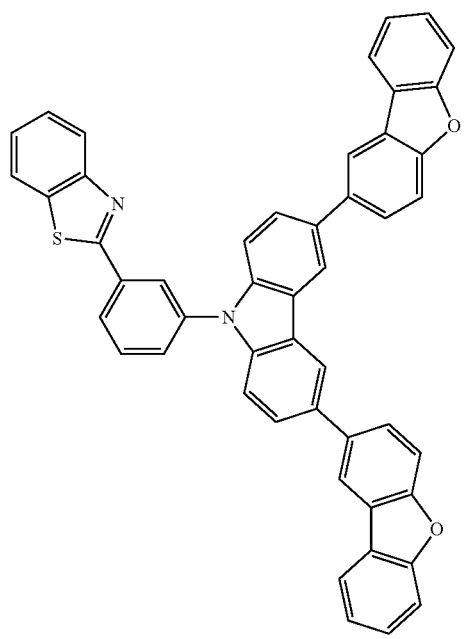
[Chemical Formula A-48]
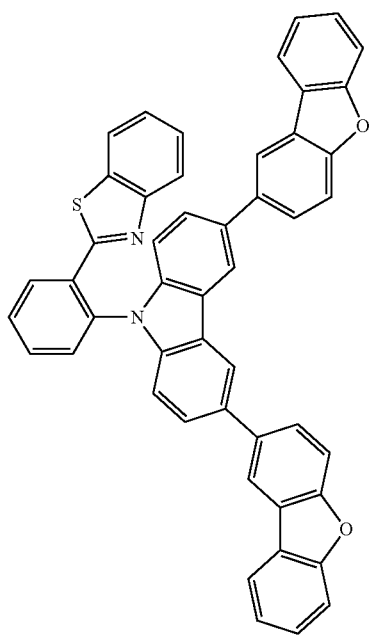

[Chemical Formula A-49]
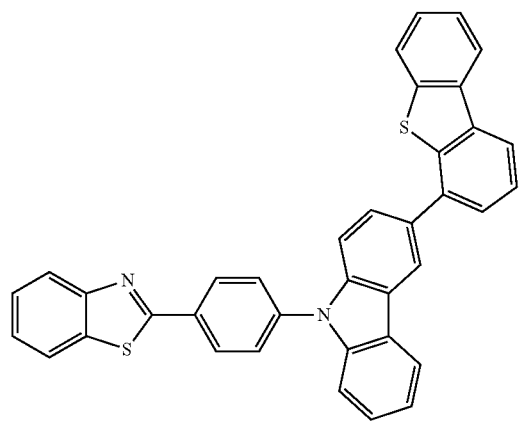
[Chemical Formula A-50]
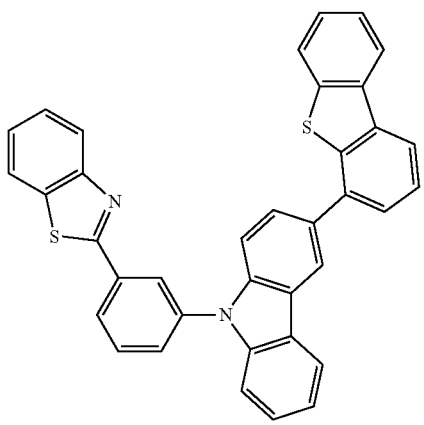
[Chemical Formula A-51]
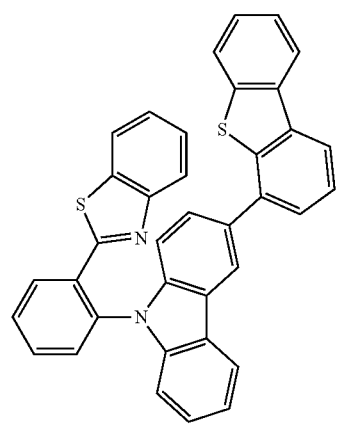
[Chemical Formula A-52]
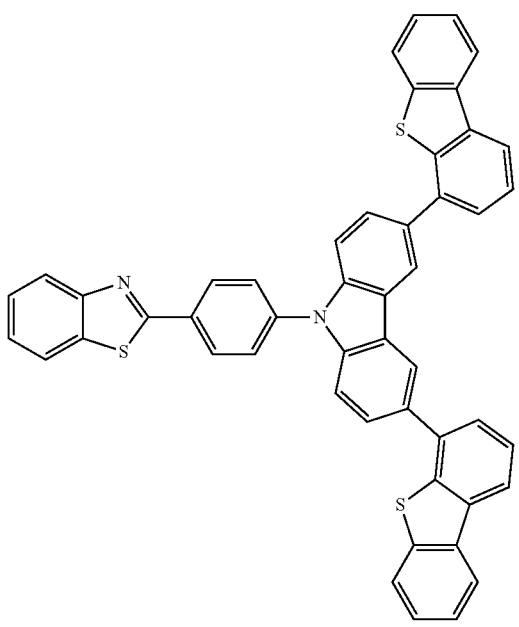

[Chemical Formula A-53]
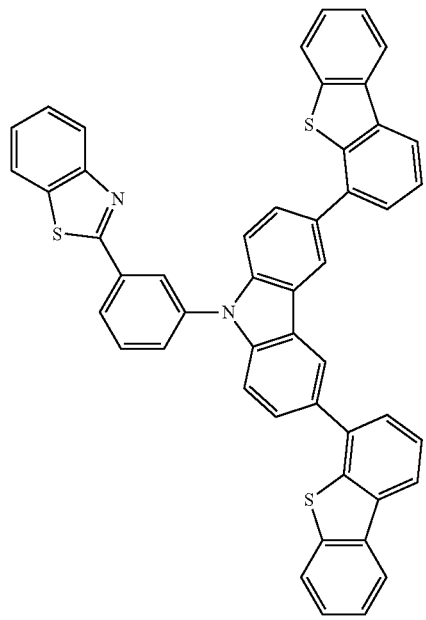
[Chemical Formula A-54]
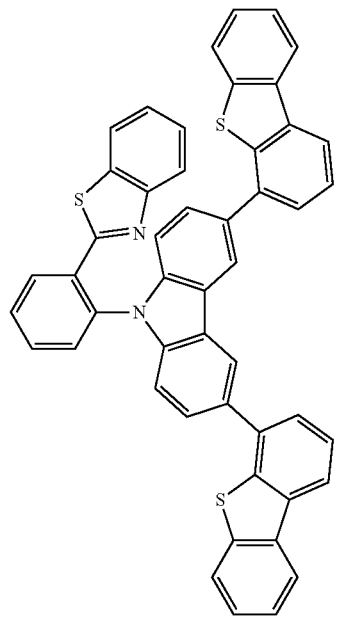
[Chemical Formula A-55]
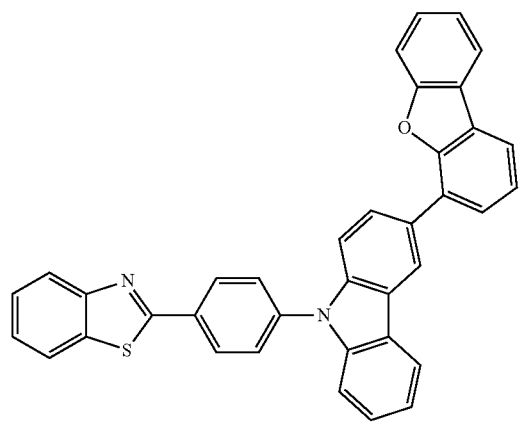
[Chemical Formula A-56]
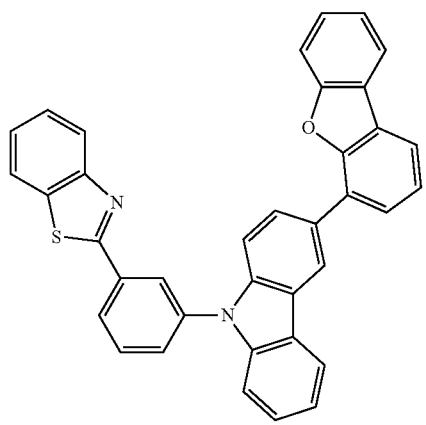

-continued
[Chemical Formula A-57]
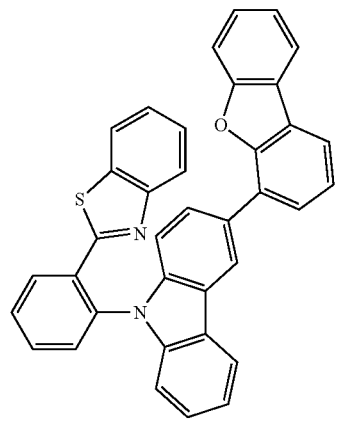
[Chemical Formula A-58]
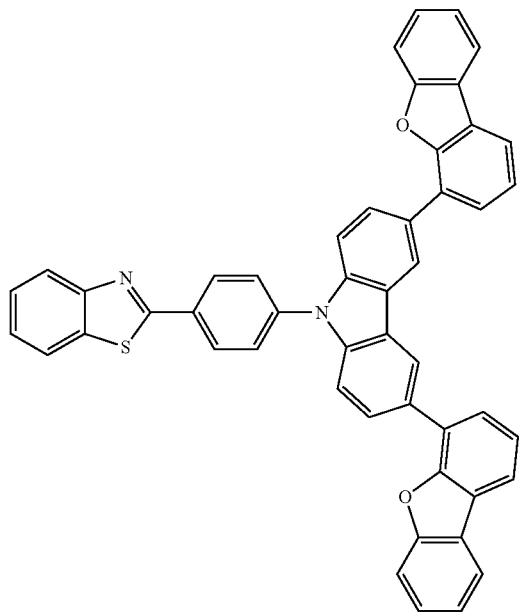
[Chemical Formula A-59]
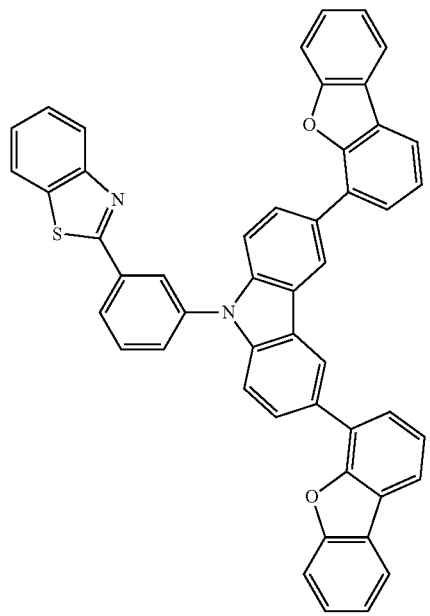
[Chemical Formula A-60]
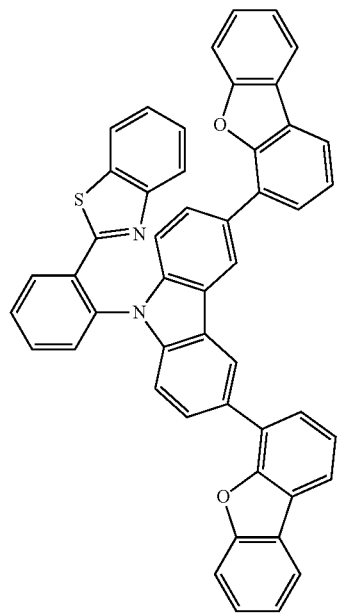
[Chemical Formula A-61]
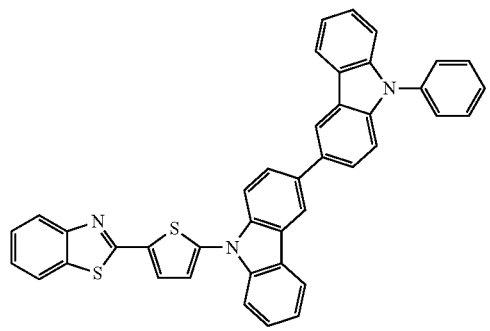
[Chemical Formula A-62]
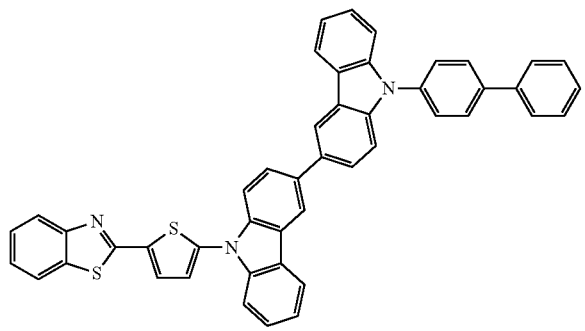

-continued
[Chemical Formula A-63]
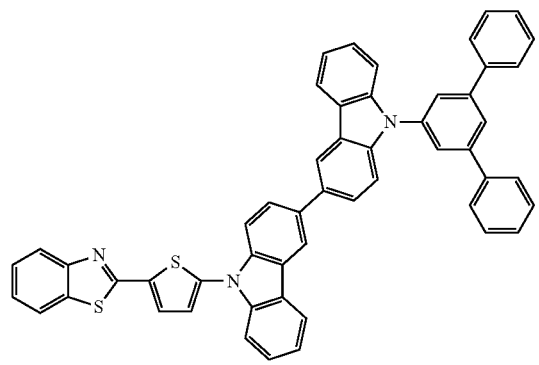
[Chemical Formula A-64]
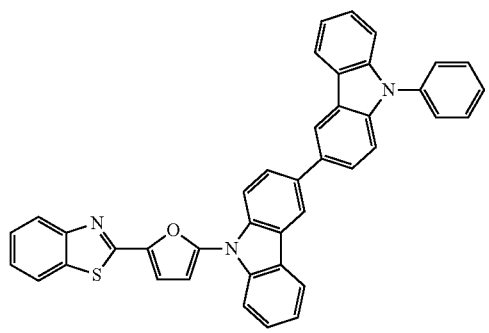
[Chemical Formula A-65]
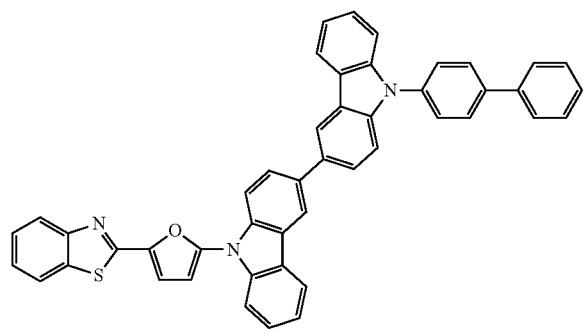
[Chemical Formula A-66]
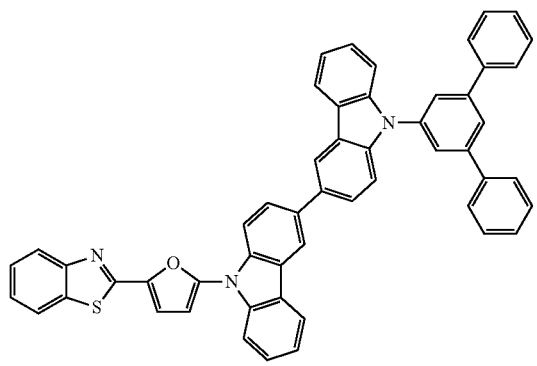
[Chemical Formula A-67]
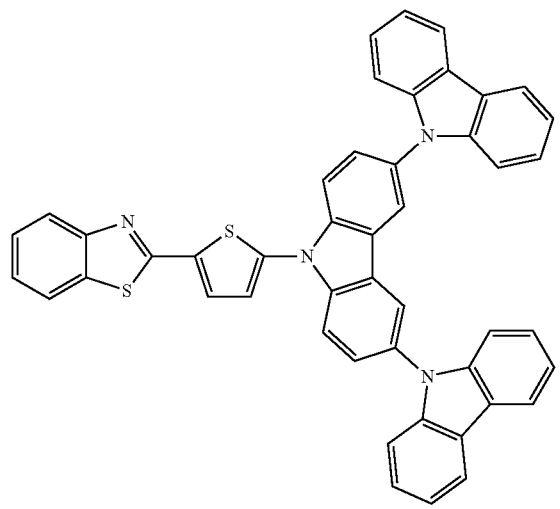
[Chemical Formula A-68]
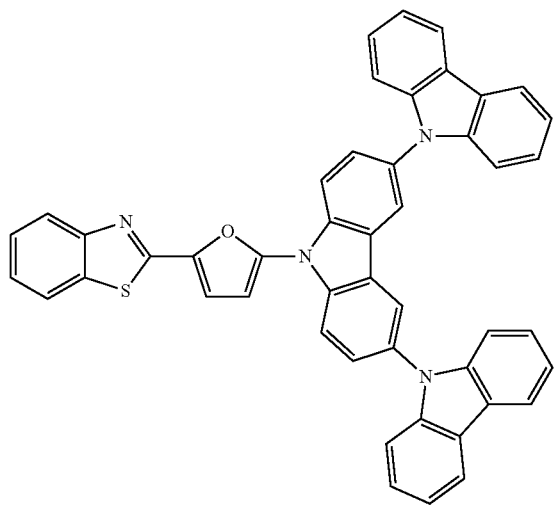

-continued
[Chemical Formula A-69]
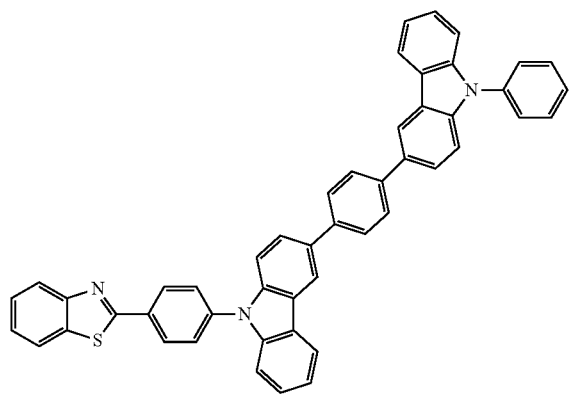
[Chemical Formula A-70]
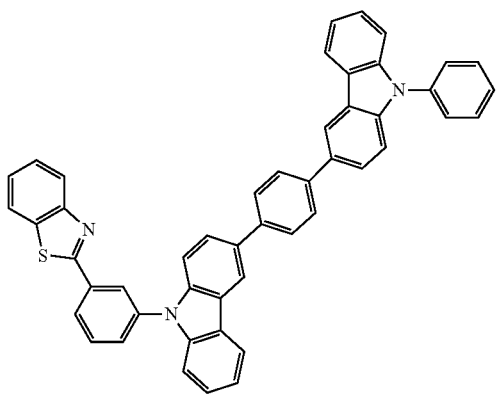
[Chemical Formula A-71]
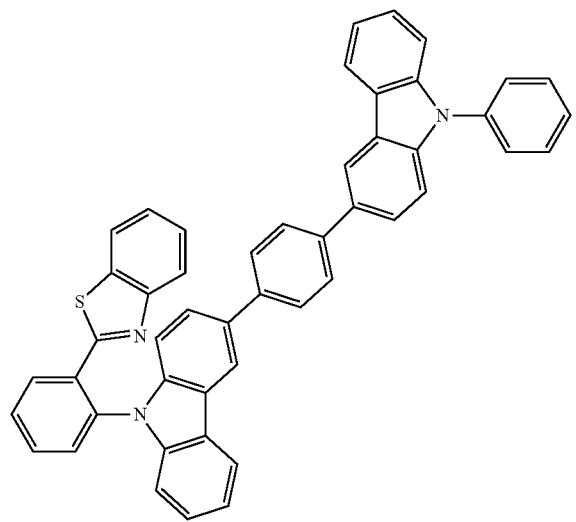
[Chemical Formula A-72]
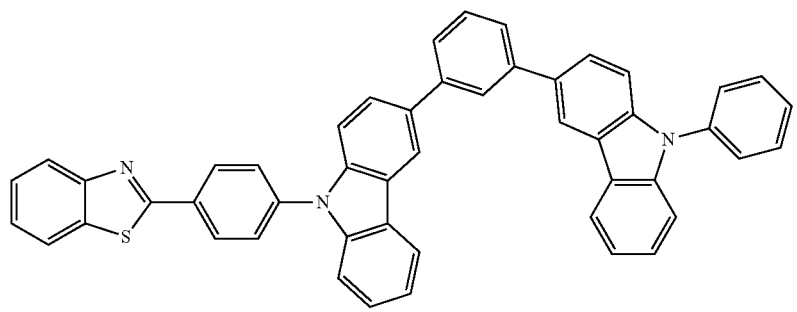
[Chemical Formula A-73]
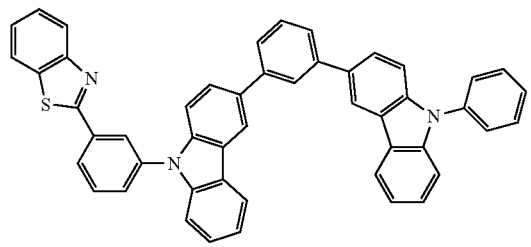
[Chemical Formula A-74]
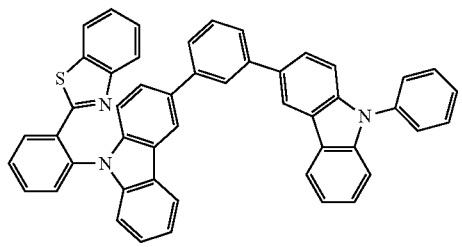

The compound for an organic optoelectronic device may be one of compounds represented by the following Chemical Formulae B-1 to B-8.
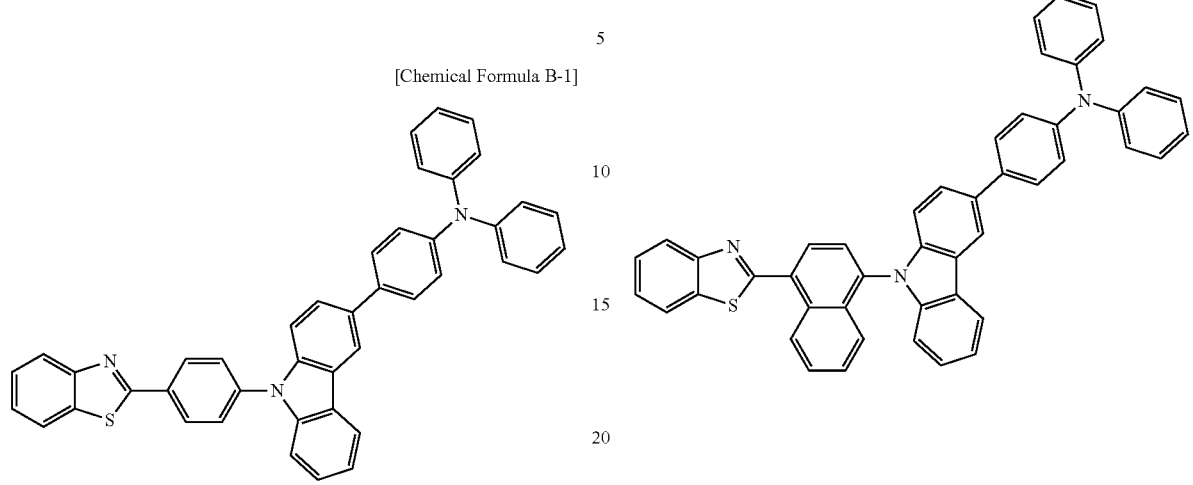

[Chemical Formula B-7]
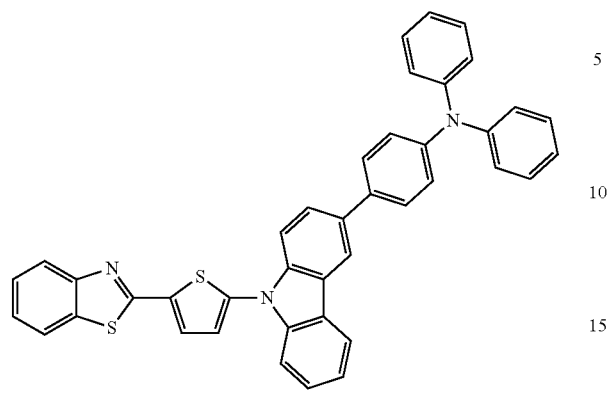
[Chemical Formula C-2]
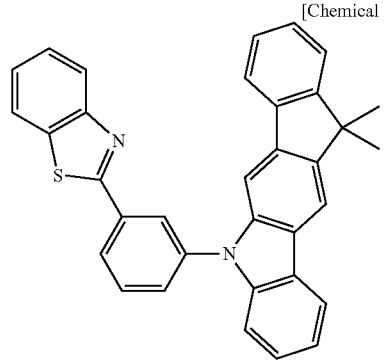
[Chemical Formula C-3]
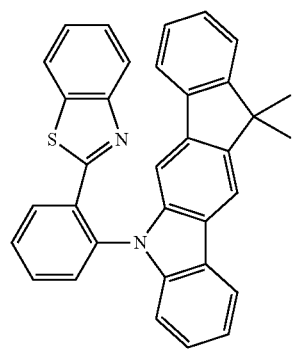
[Chemical Formula B-8]
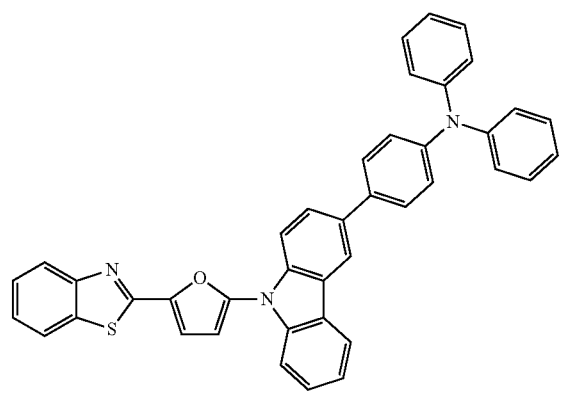
[Chemical Formula C-4]
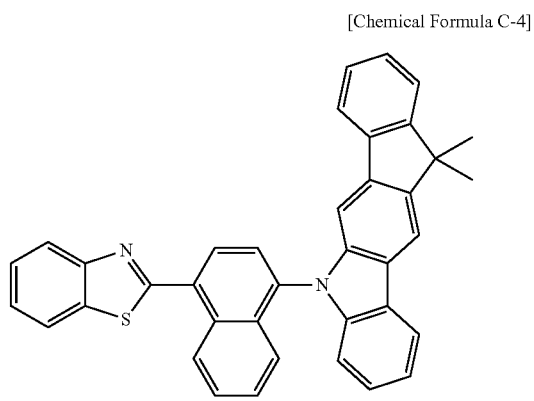
The compound for an organic optoelectronic device may be one of compounds represented by the following Chemical Formulae C-1 to C-45.
[Chemical Formula C-1]
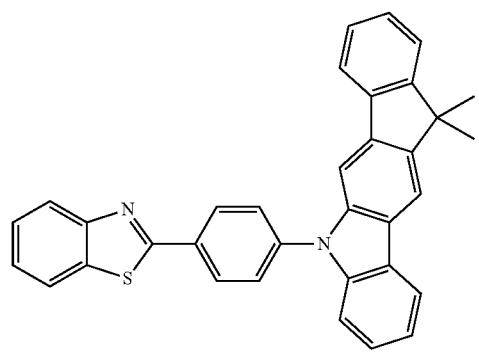
[Chemical Formula C-5]
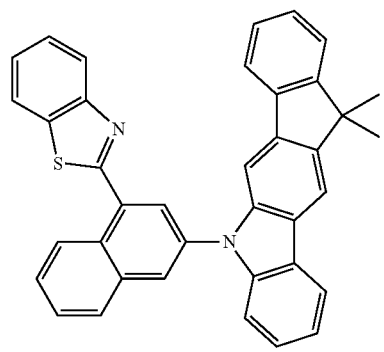

[Chemical Formula C-6]
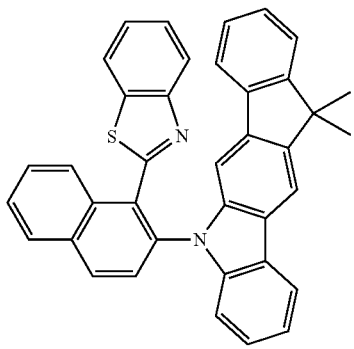
[Chemical Formula C-7]
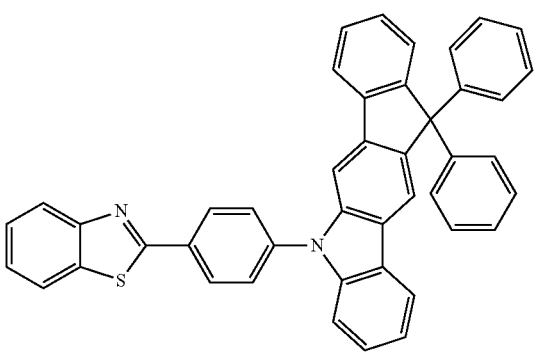
[Chemical Formula C-8]
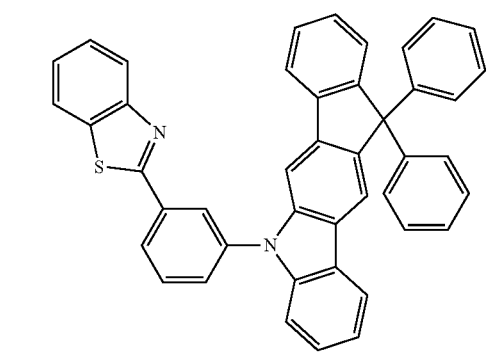
[Chemical Formula C-9]
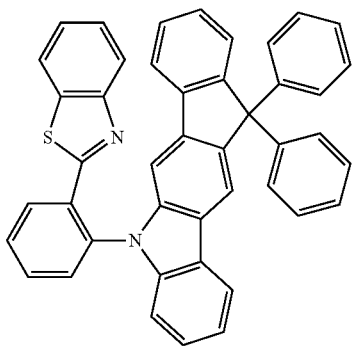
[Chemical Formula C-10]
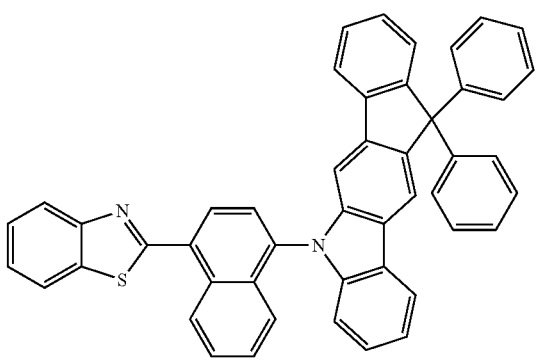
[Chemical Formula C-11]
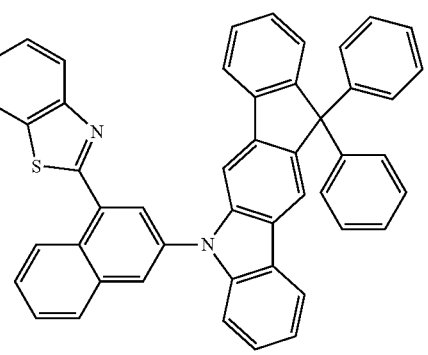
[Chemical Formula C-12]
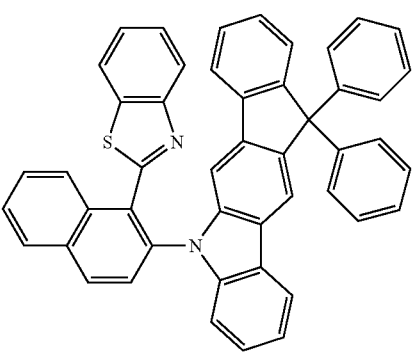
[Chemical Formula C-13]
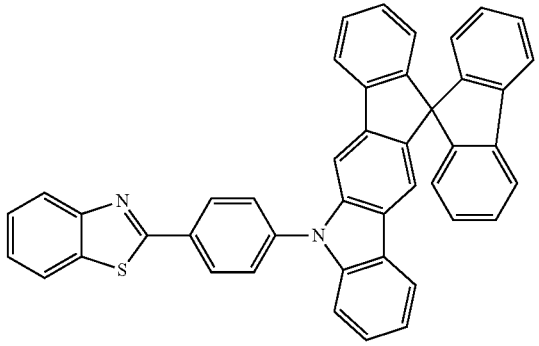

[Chemical Formula C-14]
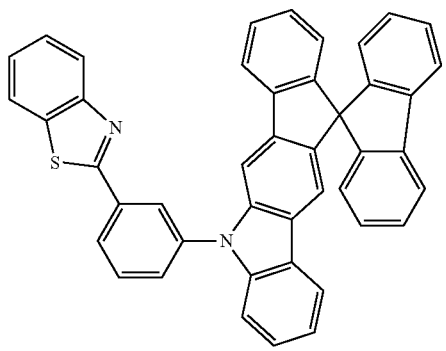
[Chemical Formula C-15]
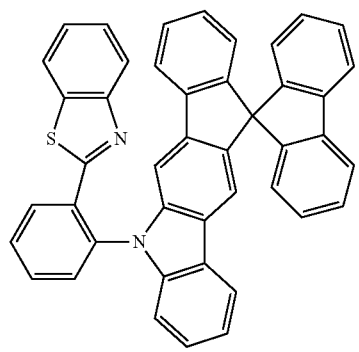
[Chemical Formula C-16]
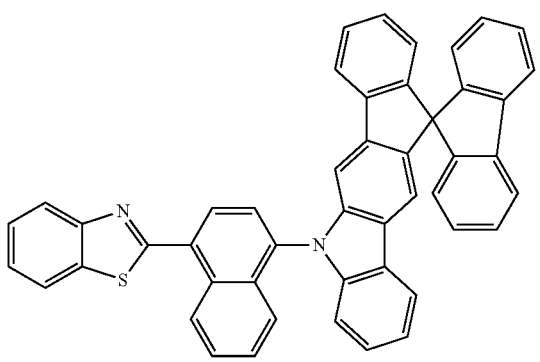
[Chemical Formula C-17]
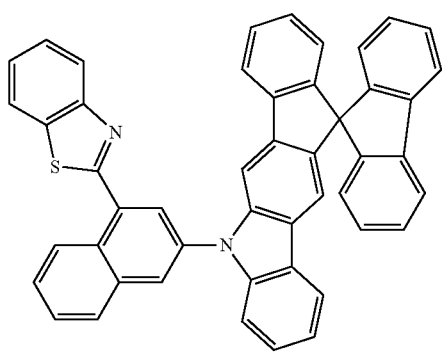
[Chemical Formula C-18]
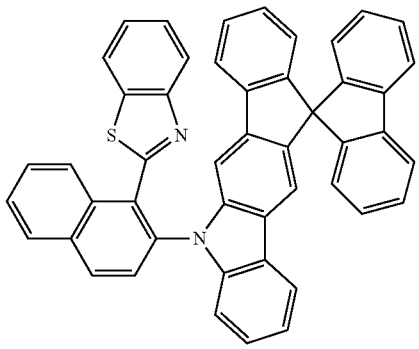
[Chemical Formula C-19]
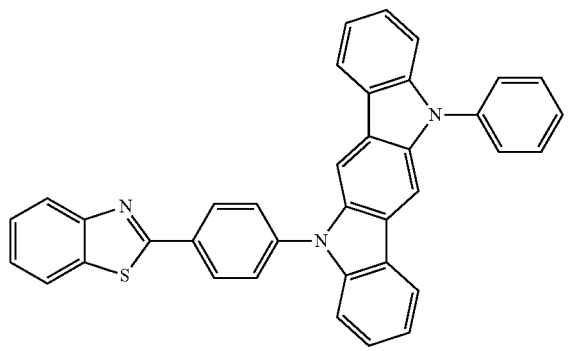
[Chemical Formula C-20]
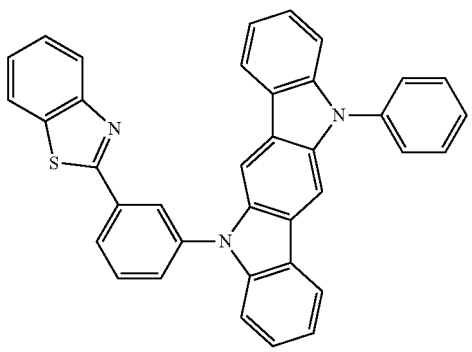
[Chemical Formula C-21]
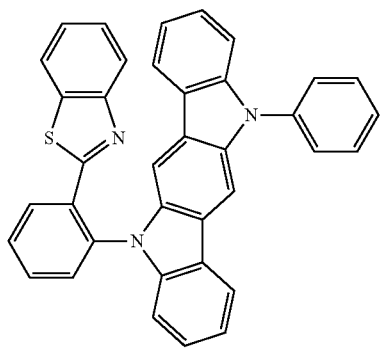

[Chemical Formula C-22]
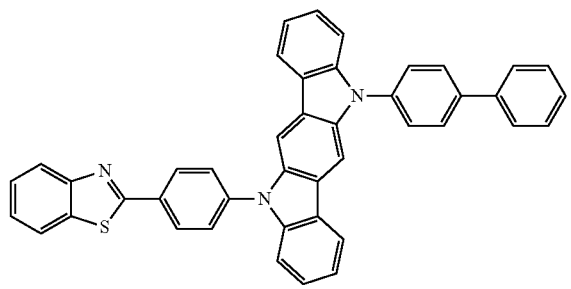
[Chemical Formula C-23]
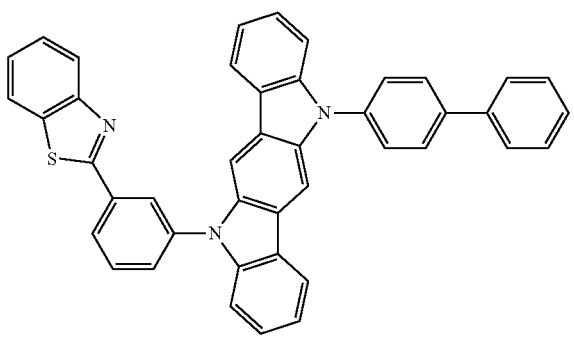
[Chemical Formula C-24]
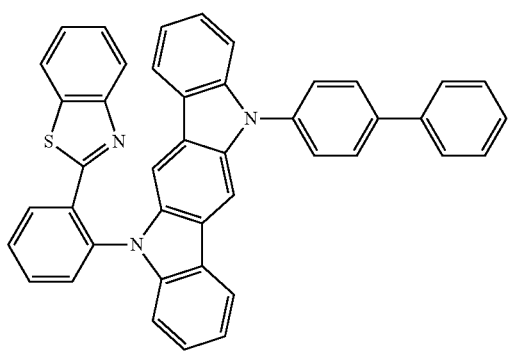
[Chemical Formula C-25]
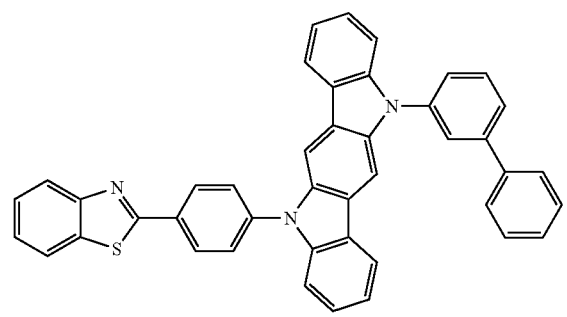
[Chemical Formula C-26]
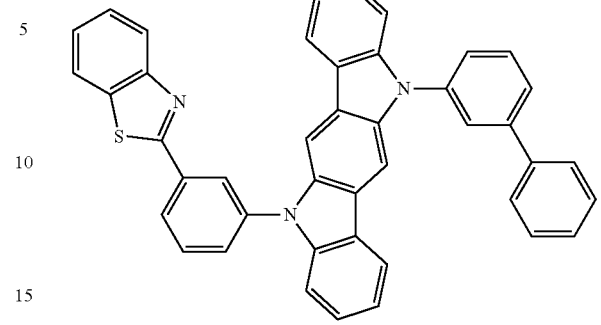
[Chemical Formula C-27]
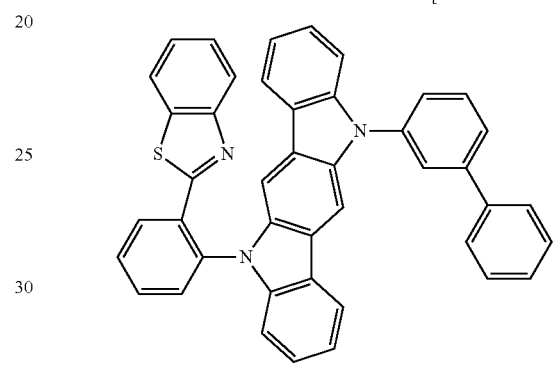
[Chemical Formula C-28]
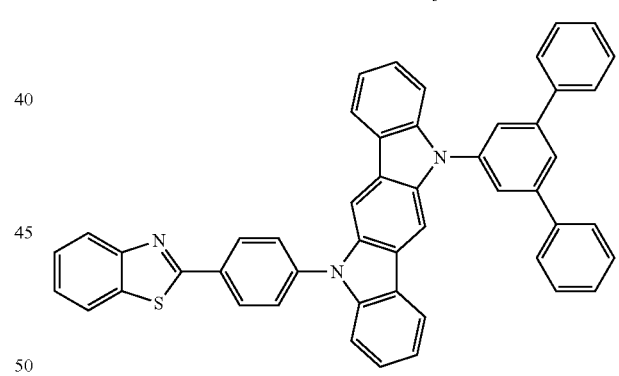
[Chemical Formula C-29]
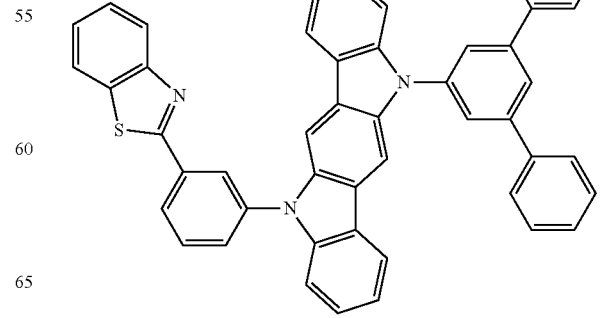

[Chemical Formula C-30]
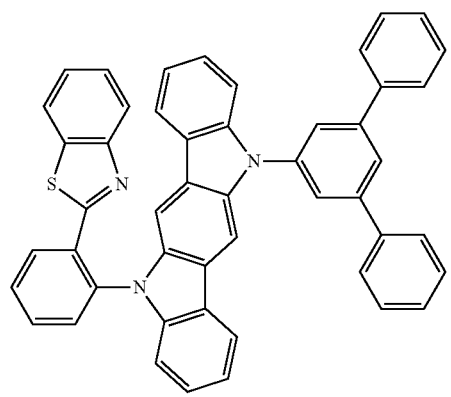
[Chemical Formula C-34]
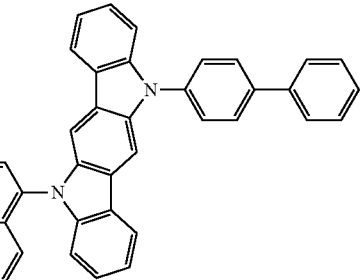
[Chemical Formula C-31]
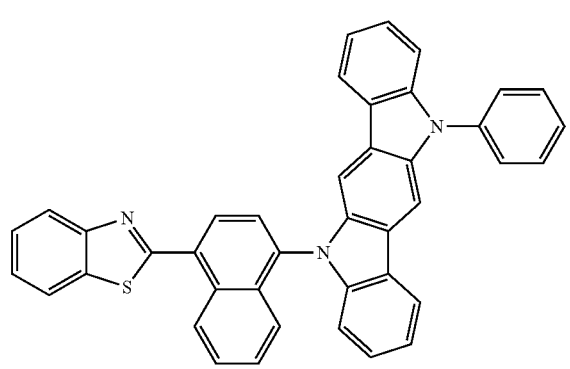
[Chemical Formula C-35]
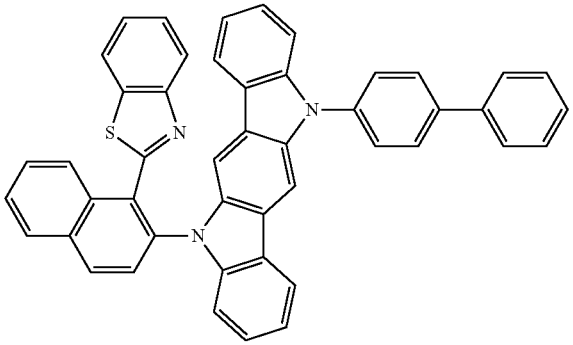
[Chemical Formula C-32]
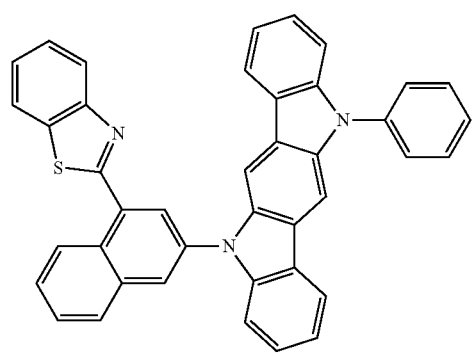
[Chemical Formula C-36]
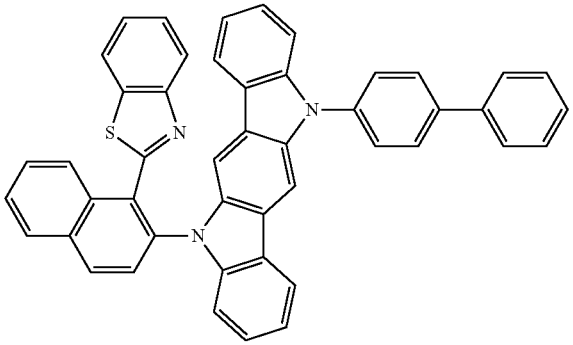
[Chemical Formula C-33]
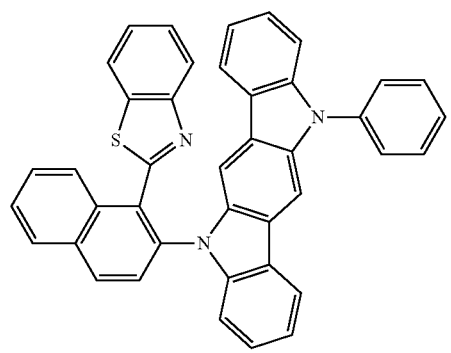
[Chemical Formula C-37]
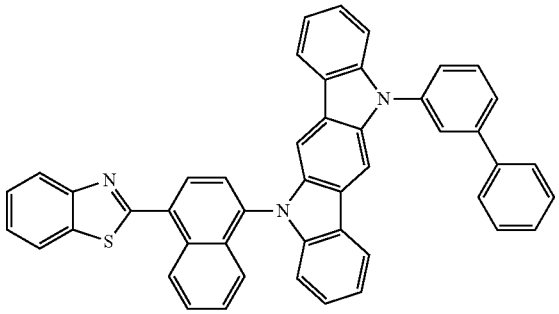

[Chemical Formula C-38]
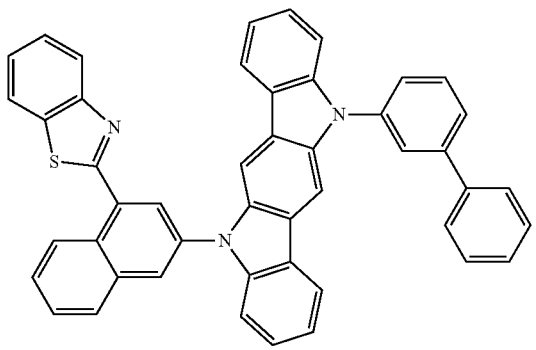
[Chemical Formula C-39]
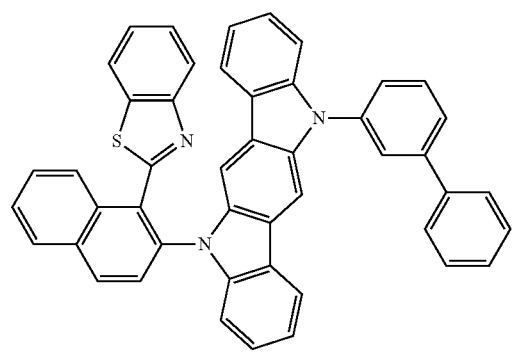
[Chemical Formula C-40]
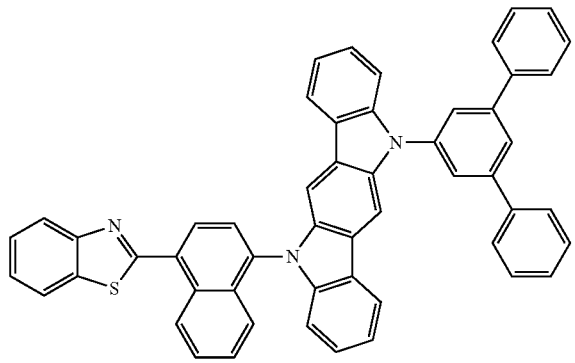
[Chemical Formula C-41]
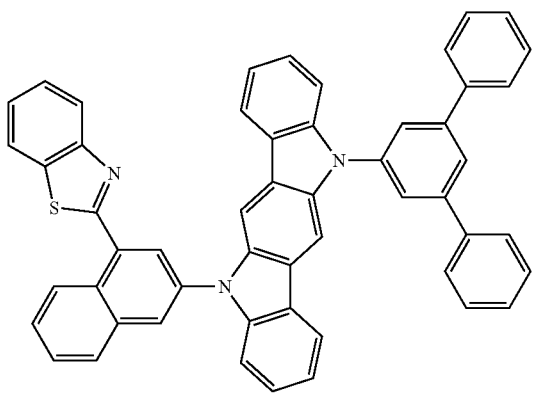
[Chemical Formula C-42]
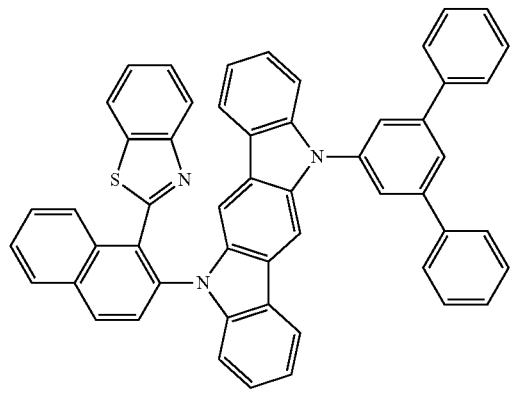
[Chemical Formula C-43]
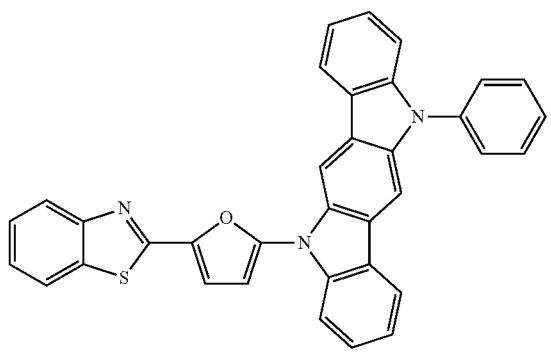
[Chemical Formula C-44]
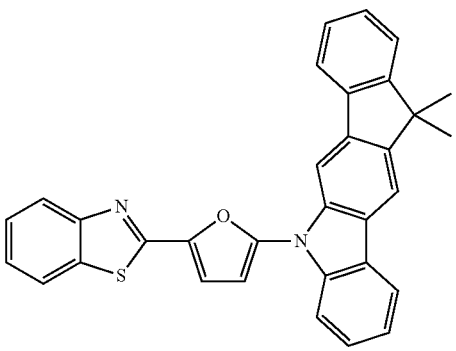
[Chemical Formula C-45]
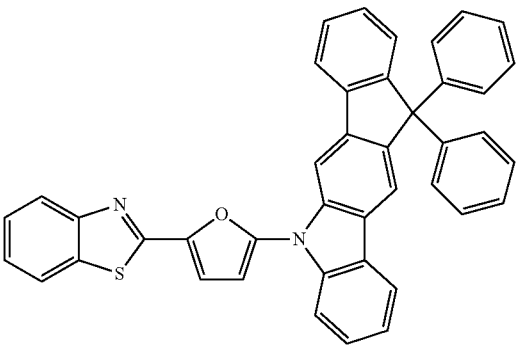

The compound for an organic optoelectronic device may be one of compounds represented by the following Chemical Formulae D-1 to D-8.
[Chemical Formula D-1]
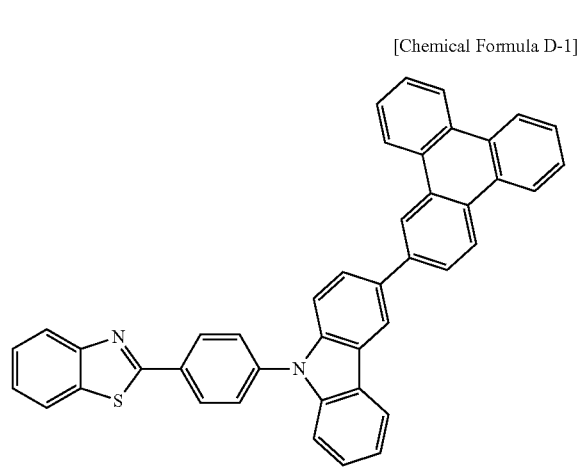
[Chemical Formula D-2]
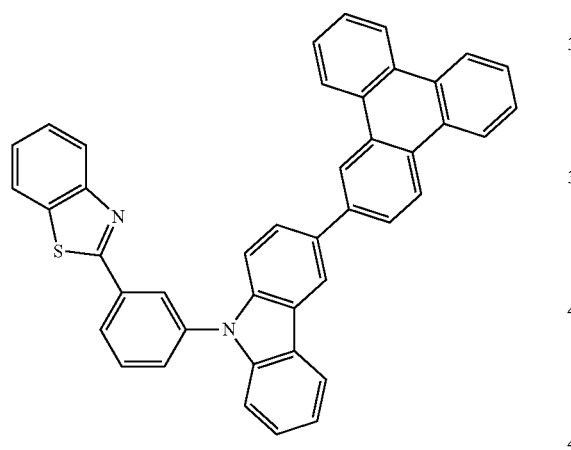
[Chemical Formula D-3]
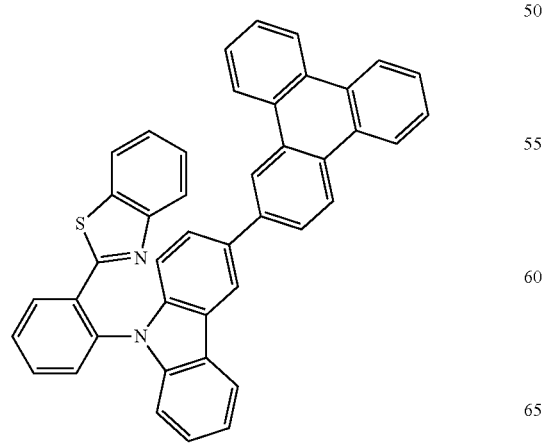
[Chemical Formula D-4]
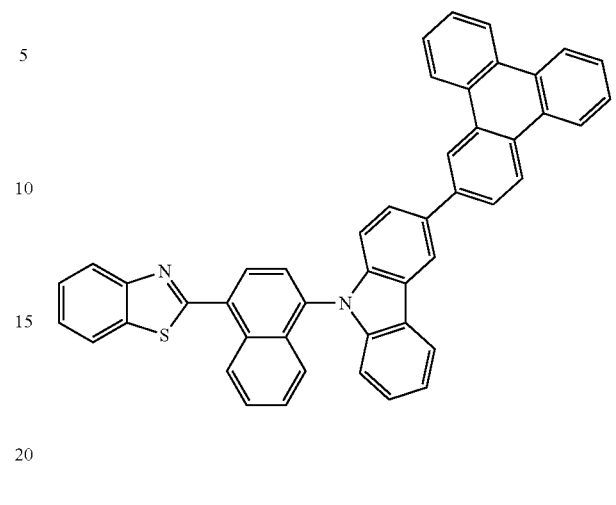
[Chemical Formula D-5]
[Chemical Formula D-6]
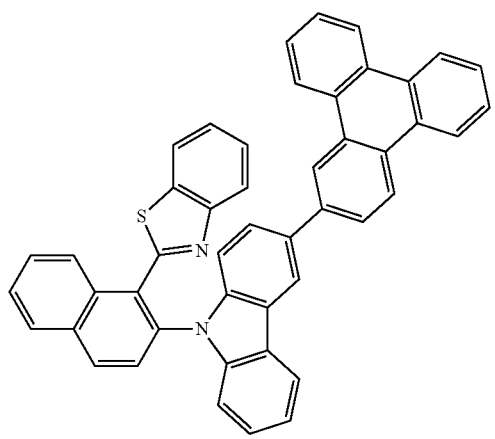

-continued

[Chemical Formula D-7]

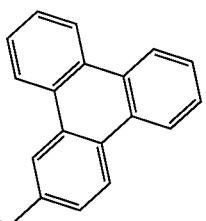

[Chemical Formula D-8]

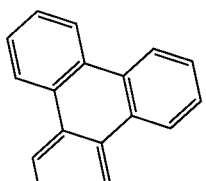

The compound for an organic optoelectronic device may have triplet exciton energy (T1) of greater than or equal to about 2.0 eV.

The organic optoelectronic device may be selected from an organic photoelectric device, an organic light emitting diode, an organic solar cell, an organic transistor, an organic photo-conductor drum, and an organic memory device.

In another embodiment of the present invention, provided is an organic light emitting diode including an anode, a cathode, and at least one organic thin layer interposed between the anode and cathode, wherein at least one of the organic thin layers includes the above compound for an organic optoelectronic device.

The organic thin layer may be selected from an emission layer, a hole transport layer, a hole injection layer, an electron transport layer, an electron injection layer, a hole blocking layer, and a combination thereof.

The compound for an organic optoelectronic device may be included in a hole transport layer (HTL) or a hole injection layer (HIL).

The compound for an organic optoelectronic device may be included in an emission layer.

The compound for an organic optoelectronic device may be used as a phosphorescent or fluorescent host material in an emission layer.

In yet another embodiment of the present invention, a display device including the above organic light emitting diode is provided.

Advantageous Effects

A compound having high hole or electron transport properties, film stability, thermal stability, and high triplet exciton energy may be provided.

Such a compound may be used as a hole injection/transport material, host material, or electron injection/transport material of an emission layer. An organic optoelectronic device using the same has improved life-span characteristics, and high luminous efficiency at a low driving voltage due to excellent electrochemical and thermal stability.

<Description of Symbols>

Figure 1:
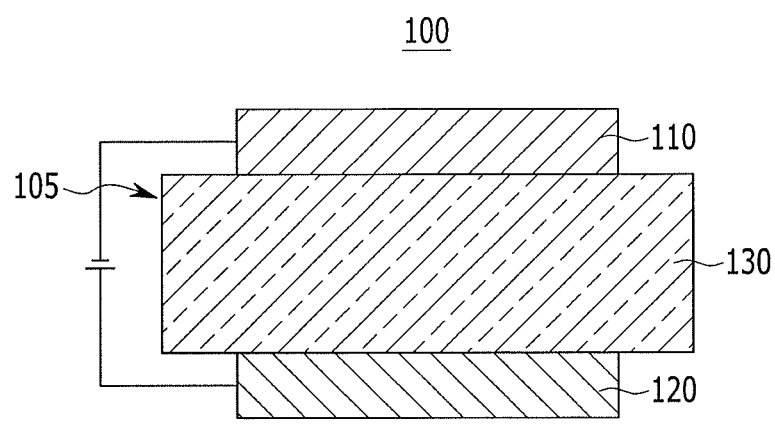
FIGS. 1 to 5 are cross-sectional views showing organic light emitting diodes according to various embodiments of the present invention including the compound for an organic optoelectronic device according to one embodiment of the present invention.

| | |
|---|---|
| 100: organic light emitting diode | 110: cathode |
| 120: anode | 105: organic thin layer |
| 130: emission layer | 140: hole transport layer (HTL) |
| 150: electron transport layer (ETL) | 160: electron injection layer (EIL) |
| 170: hole injection layer (HIL) | 230: emission layer + electron transport layer (ETL) |

BEST MODE

Hereinafter, embodiments of the present invention are described in detail. However, these embodiments are exemplary, and this disclosure is not limited thereto.

As used herein, when a definition is not otherwise provided, the term "substituted" refers to one substituted with a substituent selected from deuterium, a halogen, a hydroxy group, an amino group, a substituted or unsubstituted C1 to C30 amine group, a nitro group, a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group and the like, or a cyano group, instead of at least one hydrogen of a substituent or a compound.

The two adjacent substituent selected from the substituted a halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as trifluoromethyl group and the like, or cyano group may be fused to form a ring.

In the present specification, when specific definition is not otherwise provided, "hetero" refers to one including 1 to 3 hetero atoms selected from N, O, S, and P, and remaining carbons in one compound or substituent.

In the present specification, when a definition is not otherwise provided, the term "combination thereof" refers to at least two substituents bound to each other by a linker, or at least two substituents condensed to each other.

In the present specification, when a definition is not otherwise provided, "alkyl group" refers to an aliphatic hydrocarbon group. The alkyl group may be "a saturated alkyl group" without any double bond or triple bond. The alkyl group may be branched, linear or cyclic.

The "alkenylene group" refers to a functional group of at least one carbon-carbon double bond of at least two carbons, and the "alkynylene group" refers to a functional group of at least one carbon-carbon triple bond of at least two carbons.

The alkyl group may be a C1 to C20 alkyl group. More specifically, the alkyl group may be a C1 to C10 alkyl group or a C1 to C6 alkyl group.

For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

"Aromatic group" refers to a cyclic functional group where all elements have p-orbitals, and these p-orbitals forms conjugation. Specific examples are aryl group and a heteroaryl group.

"Aryl group" includes monocyclic or fused ring polycyclic (i.e., rings sharing adjacent pairs of carbon atoms) groups.

"Heteroaryl group" refers to aryl group including 1 to 3 hetero atoms selected from N, O, S, and P, and remaining carbons. When the heteroaryl group is a fused ring, each ring may include 1 to 3 hetero atoms.

As used herein, the carbazole-based derivative may refer to a substituted structure where a nitrogen atom of a substituted or unsubstituted carbazolyl group is substituted with a hetero atom or carbon except nitrogen. Specific examples may be dibenzofuran (a dibenzofuranyl group), dibenzothiophene (a dibenzothiopheneyl group), fluorine (a fluorenyl group) and the like.

In the present specification, hole characteristics refer to characteristics that holes formed in the anode is easily injected into the emission layer and transported in the emission layer due to conductive characteristics according to HOMO level.

Electron characteristics refer to characteristics that electron formed in the cathode is easily injected into the emission layer and transported in the emission layer due to conductive characteristics according to LUMO level.

According to one embodiment of the present invention, a compound for an organic optoelectronic device may have a core including a substituted or unsubstituted benzthiazole group and a substituted or unsubstituted carbazolyl group.

The substituted or unsubstituted benzthiazole group is a substituent having excellent electron characteristics. The benzthiazole group having excellent electron characteristics may be combined with a carbazolyl group having excellent hole characteristics to adjust electron and hole characteristics of the entire compound.

Accordingly, the core structure may be used as a light emitting material, a hole injection material, or a hole transport material for an organic optoelectronic device. In particular, the core structure may be appropriately used as a light emitting material.

At least one of the substituents combined with the core may have hole characteristics. Accordingly, the compound may satisfy a condition required of an emission layer by complementing hole characteristics to the core structure including benzthiazole having excellent electron characteristics. Specifically, the compound may be used as a host material for the emission layer.

The compound for an organic optoelectronic device includes a core part and various substituents for a substituent for substituting the core part and thus may have various energy bandgaps.

When the compound having an appropriate energy level depending on a substituent is used for an organic optoelectronic device, the compound may reinforce hole transport capability or electron transport capability of the organic optoelectronic device, have excellent effects on efficiency and a driving voltage, and also, have excellent electrochemical and thermal stability and thus, improve life-span characteristics during operation of the organic optoelectronic device.

According to the embodiment of the present invention, the compound for an organic optoelectronic device may be a compound for an organic optoelectronic device represented by the following Chemical Formula 1.

[Chemical Formula 1]

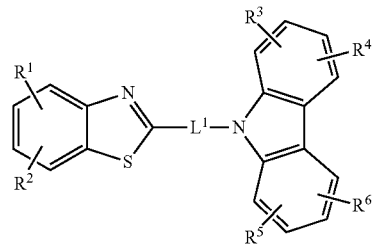

In the above Chemical Formula 1, $L^1$ is a substituted or unsubstituted C6 to C30 arylene group or a substituted or unsubstituted C2 to C30 heteroarylene group, $R^1$ and $R^2$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, $R^3$ to $R^6$ are independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof, or the $R^3$ and $R^4$ are fused to each other to provide a ring.

The compound for an organic optoelectronic device represented by the above Chemical Formula 1 necessarily includes a benzthiazole group, and herein, the substituent may increase relatively lower electron mobility than hole mobility. Accordingly, the compound may have bipolar characteristics.

When the compound having bipolar characteristics is used for an organic optoelectronic device, luminous efficiency of the organic optoelectronic device may be improved due to easy movement of holes and electrons.

The $R^1$ and $R^2$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, the $R^3$ to $R^6$ are independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof, and the compound for an organic optoelectronic device may have light emission, hole or electron characteristics; film stability; thermal stability, and high triplet exciton energy (T1) due to the substituent.

$L^1$ may be a substituted or unsubstituted C6 to C30 arylene group or a substituted or unsubstituted C2 to C30 heteroarylene group. The $L^1$ may be selectively adjusted to determine the entire conjugation length of the compound, and accordingly, a HOMO or LUMO energy level may be variously adjusted by using the $L^1$, and mobility of electrons or holes may be easily adjusted.

Specific examples of the $L^1$ may be a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylene group, a substituted or unsubstituted pyrenylene group, a substituted or unsubstituted fluorenylene group, a substituted or unsubstituted thiophene group, a substituted or unsubstituted furanyl group, and the like.

The $R^3$ to $R^6$ may be independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof. More specifically, one of the $R^3$ to $R^6$ may be a substituent having hole characteristics.

Specific examples of the substituent having hole characteristics may be a carbazolyl-based derivative, a substituted or unsubstituted amine group, and the like.

At least one out of the $R^3$ to $R^6$ may be a substituted or unsubstituted triphenylenyl group. The substituted or unsubstituted triphenylenyl group has a bulky structure and causes a resonance effect and thus, may suppress a side reaction in a solid state and increase performance of an organic light emitting diode.

In addition, the substituted or unsubstituted triphenylenyl group may make the compound bulky and thus, have an effect on lowering crystallinity and increasing life-span.

The triphenylenyl group has a wider bandgap and higher triplet exciton energy than other substituents and thus, may decrease bandgap or triplet exciton energy of the compound when the triphenylenyl group is combined with carbazole.

In addition, the $R^3$ and $R^4$ may be fused to each other to provide a ring. Specific examples of the fused $R^3$ and $R^4$ are post-illustrated.

The compound for an organic optoelectronic device represented by the above Chemical Formula 1 may be represented by the following Chemical Formula 2.

[Chemical Formula 2]

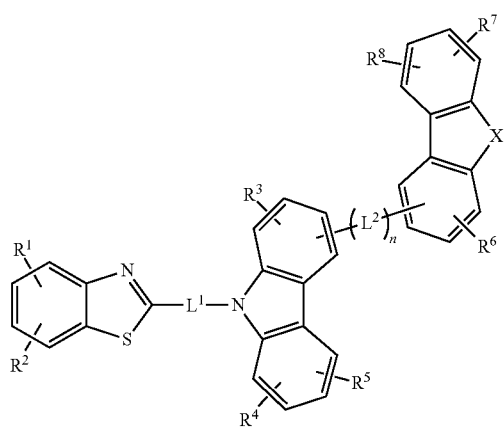

In the above Chemical Formula 2, $L^1$ and $L^2$ are independently a substituted or unsubstituted C6 to C30 arylene group or a substituted or unsubstituted C2 to C30 heteroarylene group, n is an integer ranging from 0 to 3, $R^1$ to $R^9$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, X is —$NR^9$—, —O—, —S— or —$CR^{10}R^{11}$—, wherein the $R^9$ to $R^{11}$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, or the $R^{10}$ and $R^{11}$ are fused to each other to provide a ring.

A compound represented by the above Chemical Formula 2 has a structure that a carbazolyl-based derivative substituent is necessarily combined with the core structure of a compound represented by the above Chemical Formula 1.

Since the carbazolyl-based derivative substituent has hole characteristics as described above, electron and hole characteristic of the entire compound may be appropriately adjusted.

In addition, the carbazolyl group included in the core and the carbazolyl-based derivative substituent may be combined at the 3-position of each carbon. At this position, the synthesis may easily be performed. In addition, the compound may have an appropriate energy level, and various substituents may be easily introduced into the carbazole.

The compound for an organic optoelectronic device represented by the above Chemical Formula 1 may be represented by the following Chemical Formula 3.

[Chemical Formula 3]

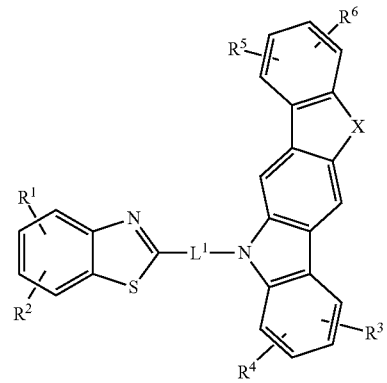

In the above Chemical Formula 3, $L^1$ is a substituted or unsubstituted C6 to C30 arylene group or a substituted or unsubstituted C2 to C30 heteroarylene group, $R^1$ to $R^6$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, X is —$NR^7$—, —O—, —S— or —$CR^8R^9$—, wherein the $R^7$ to $R^9$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, or the $R^8$ and $R^9$ are fused to each other to provide a ring.

The compound represented by the above Chemical Formula 3 for example has a structure that $R^3$ and $R^4$ in the above Chemical Formula 1 are fused to each other and form a ring.

In other words, a compound represented by the above Chemical Formula 3 has a structure that a carbazolyl group derivative having a fused ring shape is combined with a substituted or unsubstituted benzthiazole.

Herein, the entire compound may have a bulky structure, and thus, crystallinity of the compound may be decreased. When the compound has lower crystallinity, a device may have longer life-span.

The compound for an organic optoelectronic device represented by the above Chemical Formula 1 may be represented by the following Chemical Formula 4.

[Chemical Formula 4]

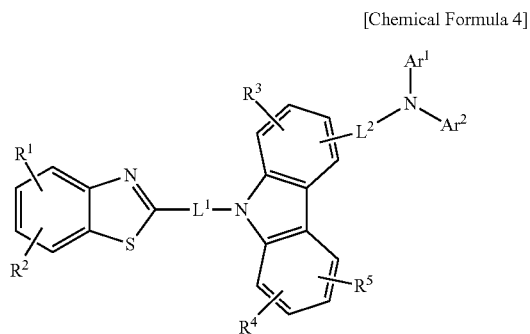

In the above Chemical Formula 4, $L^1$ and $L^2$ are independently a substituted or unsubstituted C6 to C30 arylene group or a substituted or unsubstituted C2 to C30 heteroarylene group, $R^1$ to $R^5$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, and $Ar^1$ and $Ar^2$ are independently a substituted or unsubstituted C1 to C10 alkyl group, a substituted or unsubstituted C6 to C30 aryl group, a substituted or unsubstituted C2 to C30 heteroaryl group, or a combination thereof.

A compound represented by the above Chemical Formula 4 has a structure that a substituted or unsubstituted amine group is combined with a core structure where a substituted or unsubstituted benzthiazole group and a substituted or unsubstituted carbazolyl group are combined.

The amine group is a substituent having excellent hole characteristics. The amine group may reinforce hole characteristics of the compound for an organic optoelectronic device.

The $Ar^1$ and $Ar^2$ may be independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

The $L^1$ may be a substituted or unsubstituted phenylene group or a substituted or unsubstituted naphthylene group.

More specifically, the compound for an organic optoelectronic device represented by the above Chemical Formula 1 may be represented by the following Chemical Formula 5.

[Chemical Formula 5]

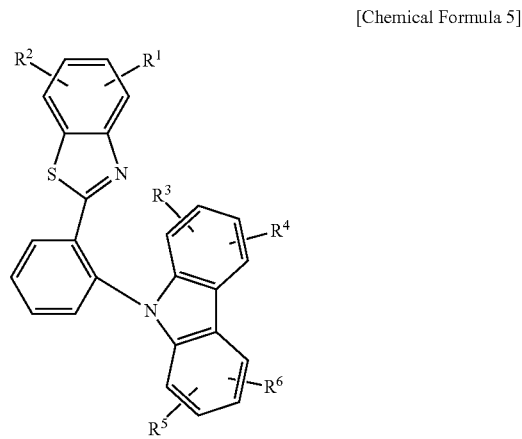

In the above Chemical Formula 5, $R^1$ and $R^2$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, $R^3$ to $R^6$ are independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof, or the $R^3$ and $R^4$ are fused to each other to provide a ring.

The compound represented by the above Chemical Formula 5 may be a compound represented by the above Chemical Formula 1 where $L^1$ is a phenylene. More specifically, in the compound, both substituents are positioned in an ortho position relative to phenylene.

Herein, the compound may have an asymmetric bipolar characteristic structure, and the asymmetric bipolar characteristic structure may improve capability of transporting holes and electrons and thus, luminous efficiency and performance of a device.

Specifically, the compound may have independent HOMO and LUMO energy distributions of carbazole and a substituted material, since conjugation of the carbazole with the substituted material is broken.

In other words, the carbazole unit appears strong in terms of the HOMO, and the substituted structure (ET characteristics) appears strong in terms of the LUMO.

The compound for an organic optoelectronic device represented by the above Chemical Formula 1 may be represented by the following Chemical Formula 6.

[Chemical Formula 6]

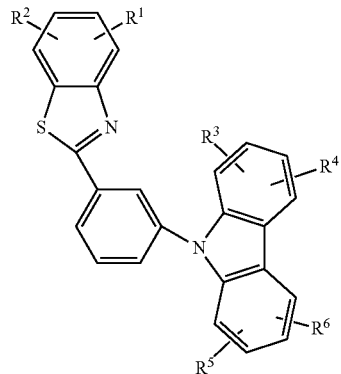

In the above Chemical Formula 6, $R^1$ and $R^2$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, $R^3$ to $R^6$ are independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof, or the $R^3$ and $R^4$ are fused to each other to provide a ring.

The compound represented by the above Chemical Formula 6 is a compound represented by the above Chemical Formula 1 where $L^1$ is phenylene. More specifically, in the compound, both substituents are positioned in a meta position relative to phenylene.

Herein, middle characteristics between para and otho may be shown.

The compound for an organic optoelectronic device represented by the above Chemical Formula 1 may be represented by the following Chemical Formula 7.

[Chemical Formula 7]

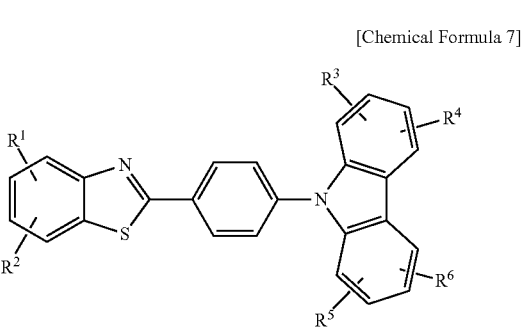

In the above Chemical Formula 7, $R^1$ and $R^2$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, $R^3$ to $R^6$ are independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof, or the $R^3$ and $R^4$ are fused to each other to provide a ring.

The compound represented by the above Chemical Formula 7 may be a compound represented by the above Chemical Formula 1 where $L^1$ is a phenylene. More specifically, in the compound, both substituents are positioned in a para position relative to phenylene.

Herein, bipolar characteristics may be distributed over the compound. In other words, since hole and electron characteristics are not biased toward one side, holes and electrons may be appropriately injected.

The compound for an organic optoelectronic device according to one embodiment of the present invention may be one of compounds represented by the following Chemical Formulae A-1 to A-74.

[Chemical Formula A-1]

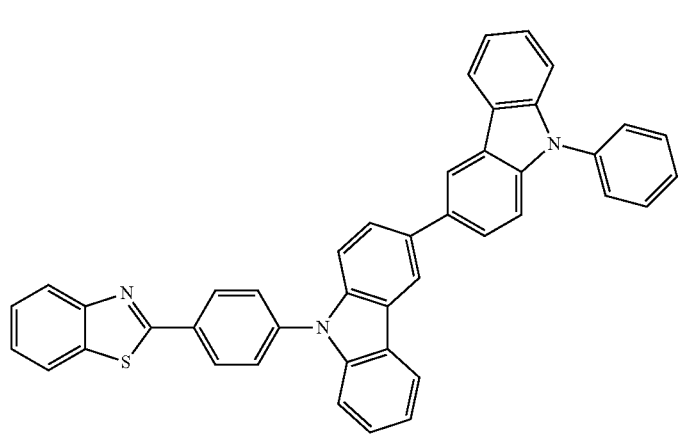

-continued
[Chemical Formula A-2]
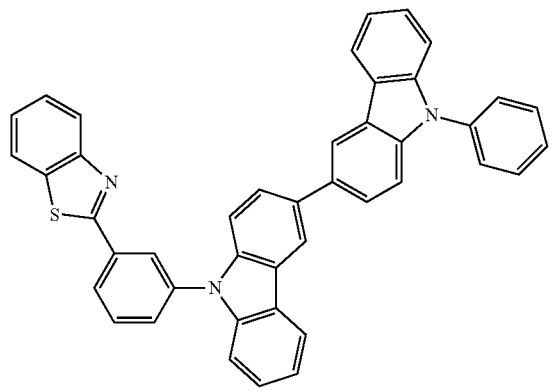
[Chemical Formula A-3]
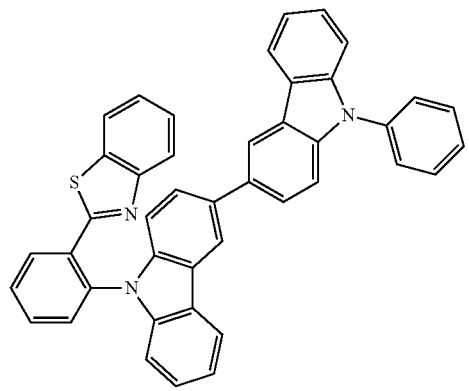
[Chemical Formula A-4]
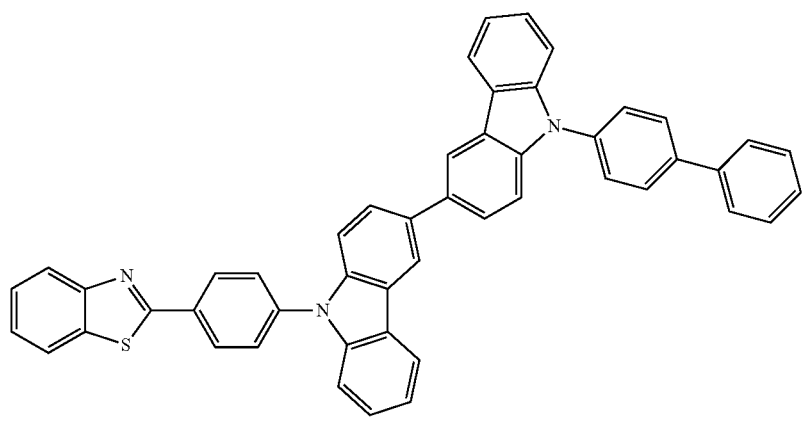
[Chemical Formula A-5]
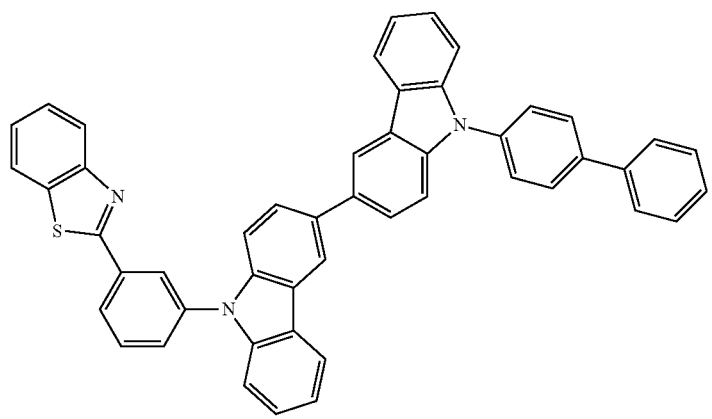
[Chemical Formula A-6]
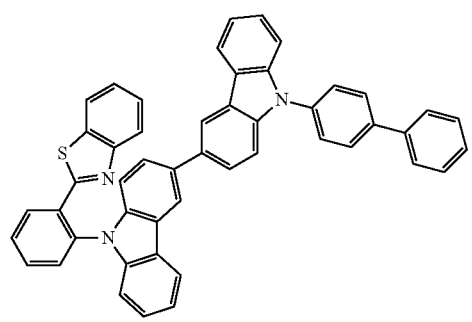
[Chemical Formula A-7]
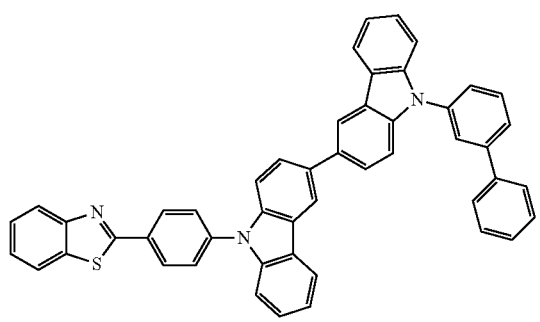

-continued
[Chemical Formula A-8]
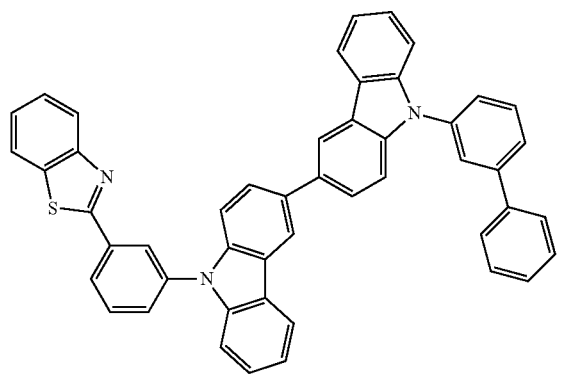
[Chemical Formula A-9]
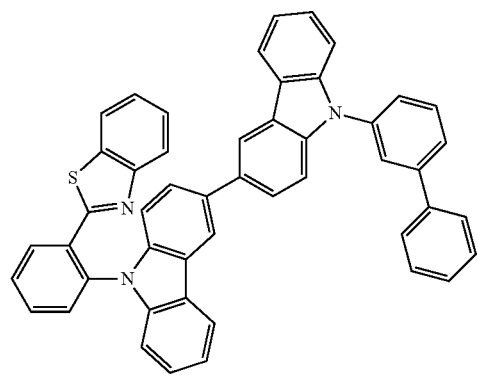
[Chemical Formula A-10]
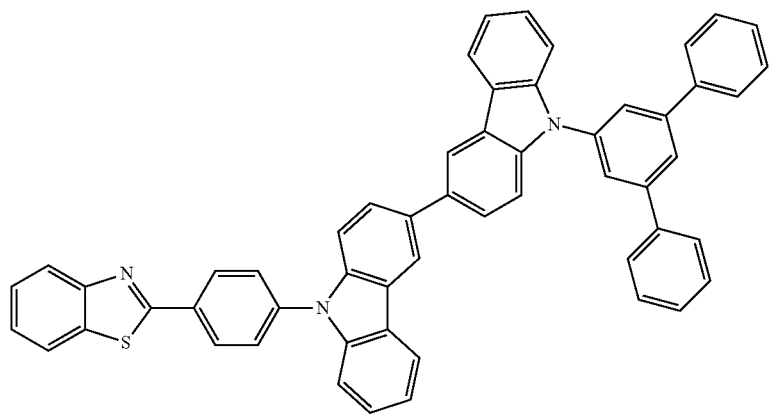
[Chemical Formula A-11]
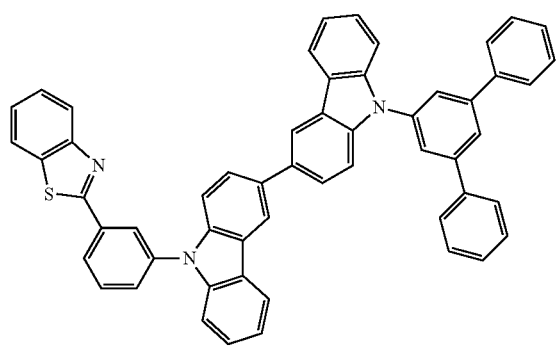
[Chemical Formula A-12]
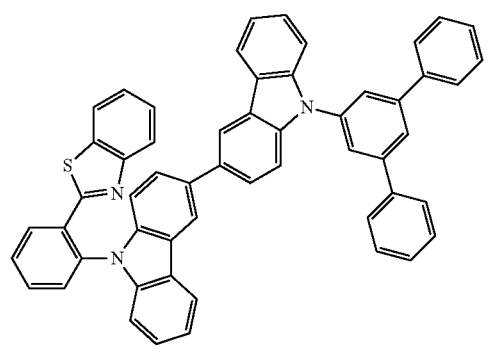
[Chemical Formula A-13]
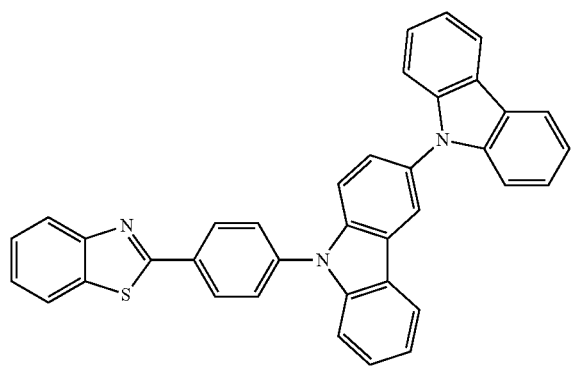
[Chemical Formula A-14]
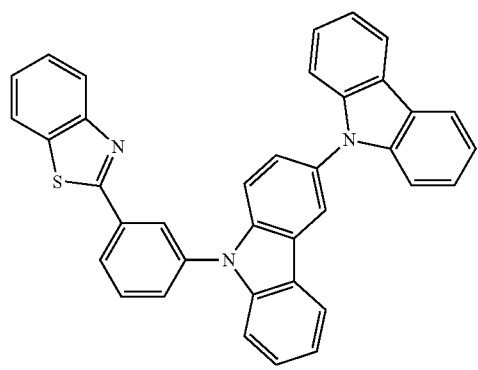

-continued
[Chemical Formula A-15]
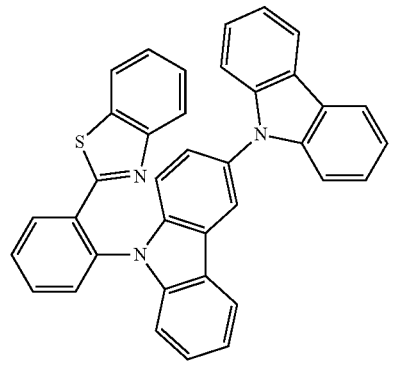
[Chemical Formula A-16]
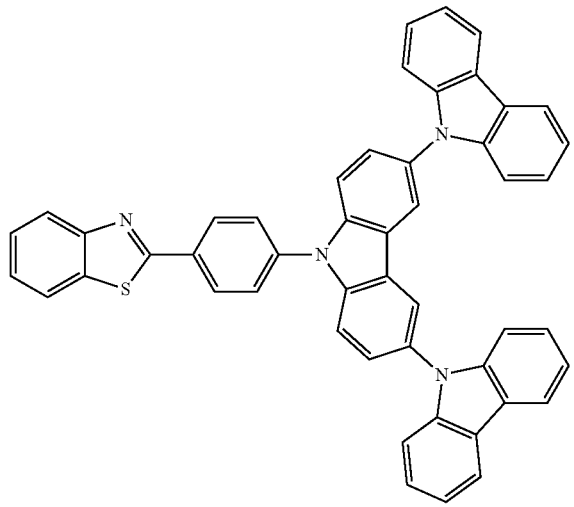
[Chemical Formula A-17]
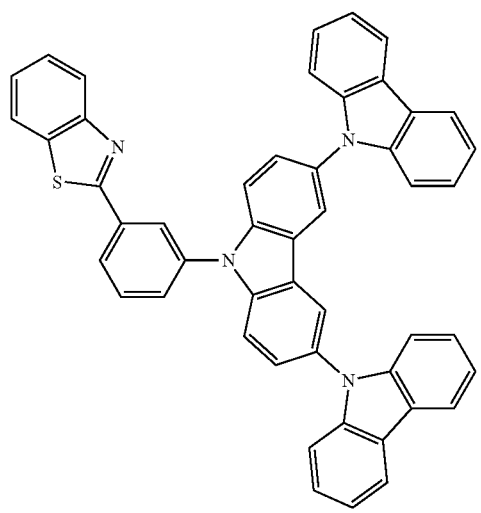
[Chemical Formula A-18]
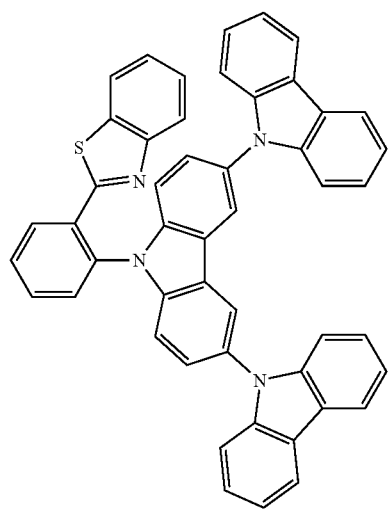
[Chemical Formula A-19]
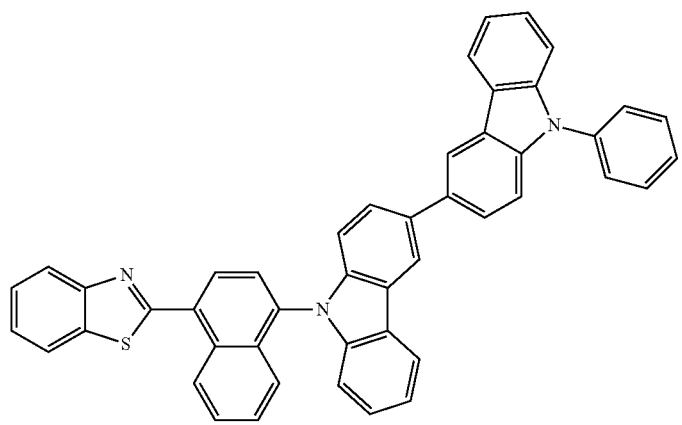

-continued
[Chemical Formula A-20]
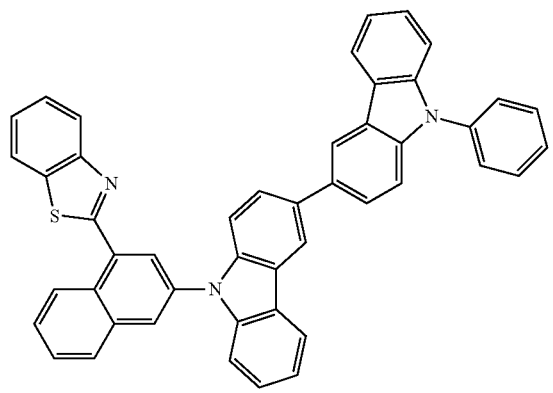
[Chemical Formula A-21]
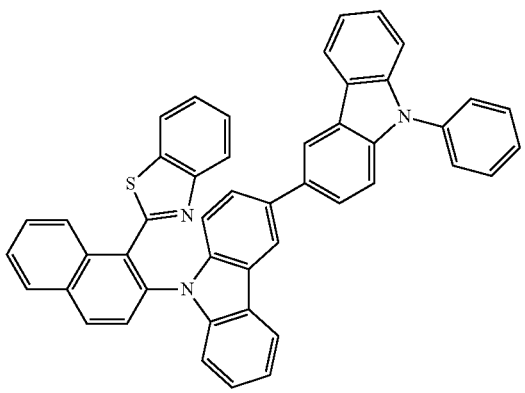
[Chemical Formula A-22]
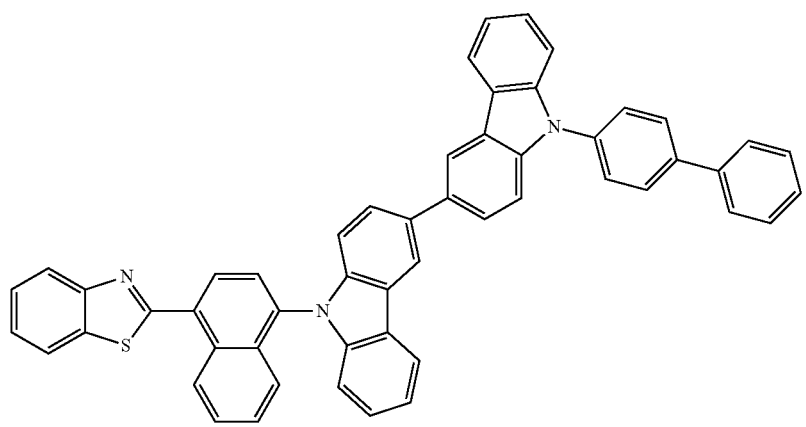
[Chemical Formula A-23]
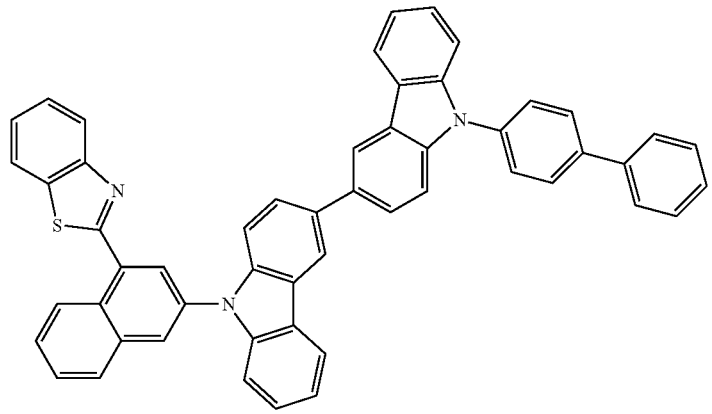
[Chemical Formula A-24]
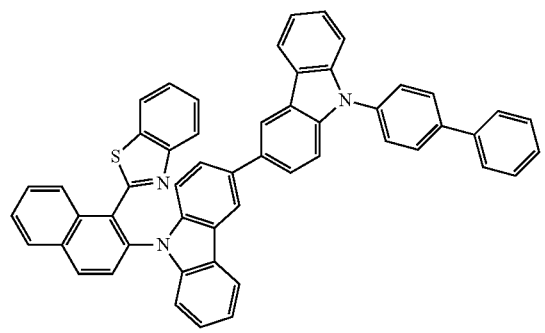
[Chemical Formula A-25]
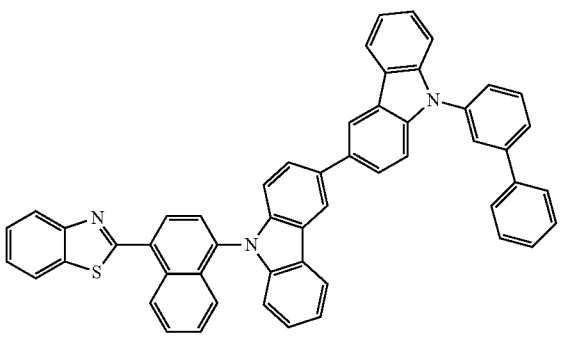

[Chemical Formula A-26]
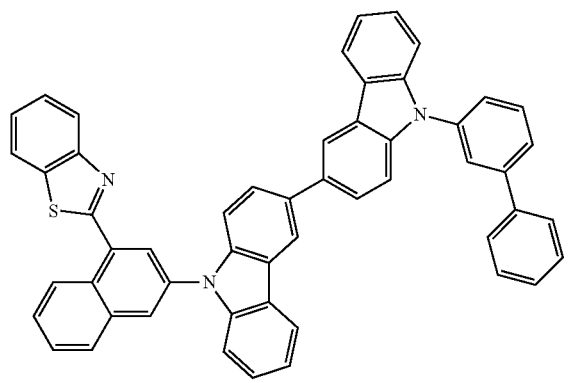
[Chemical Formula A-27]
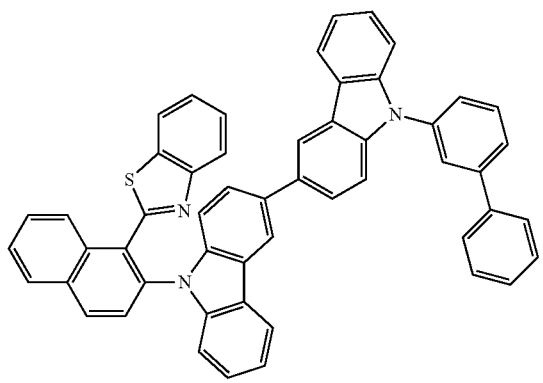
[Chemical Formula A-28]
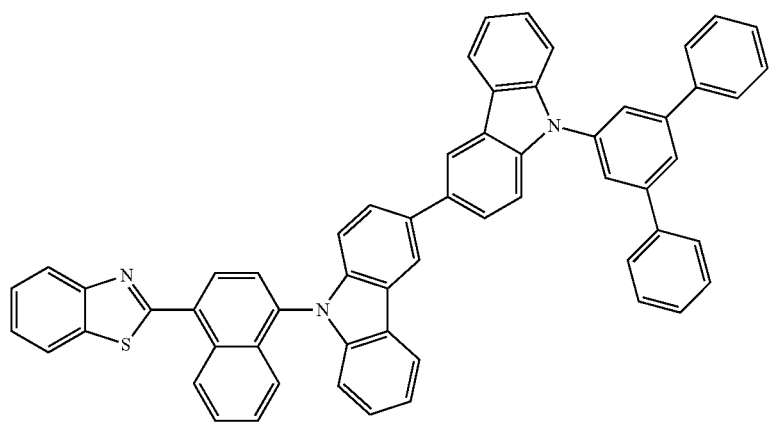
[Chemical Formula A-29]
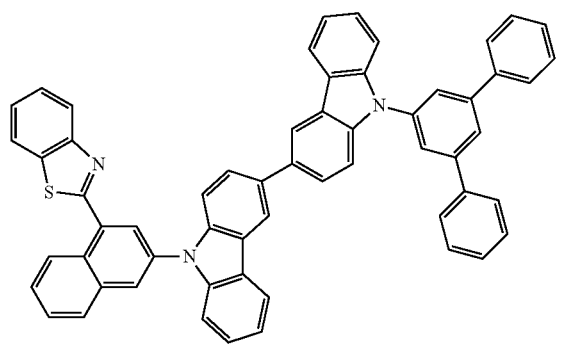
[Chemical Formula A-30]
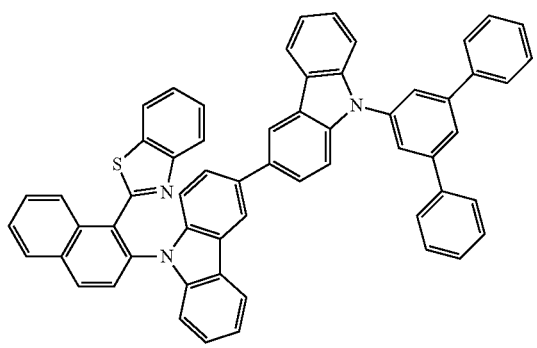
[Chemical Formula A-31]
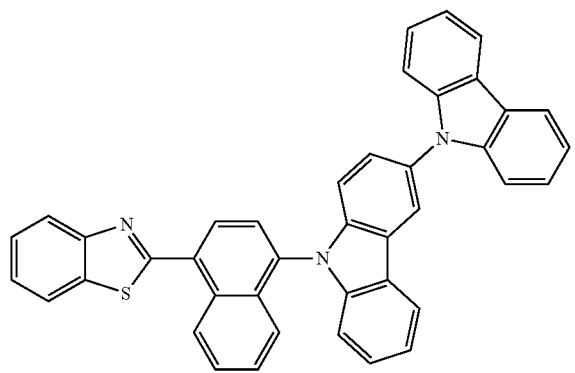
[Chemical Formula A-32]
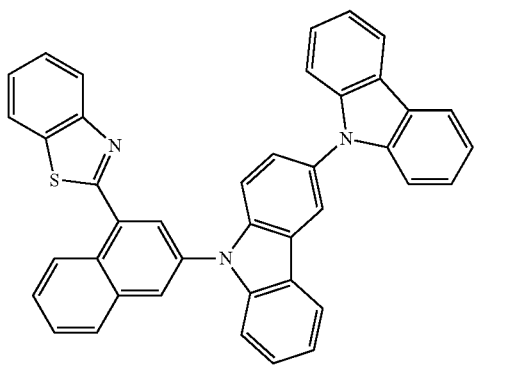

-continued
[Chemical Formula A-33]
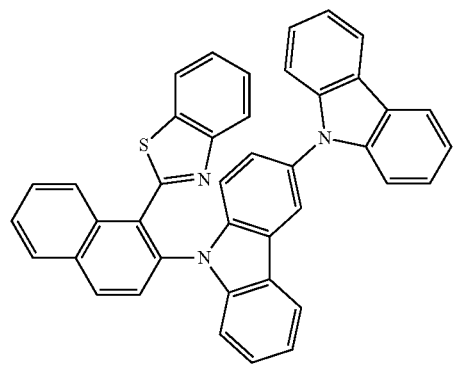
[Chemical Formula A-34]
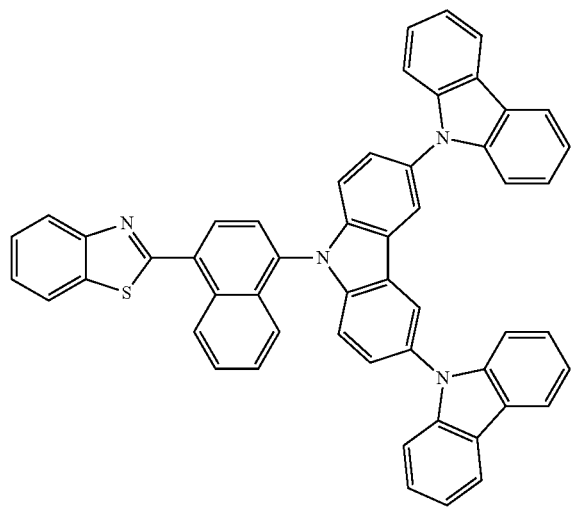
[Chemical Formula A-35]
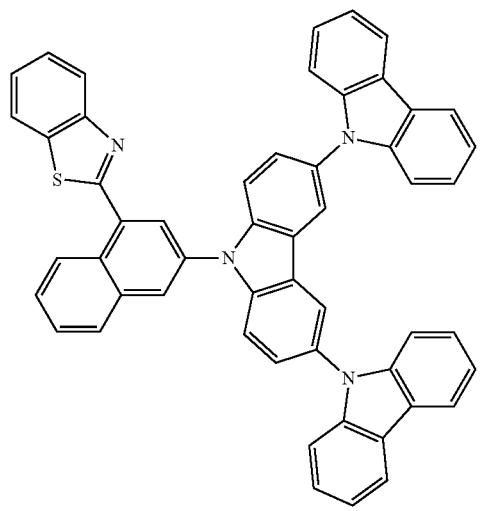
[Chemical Formula A-36]
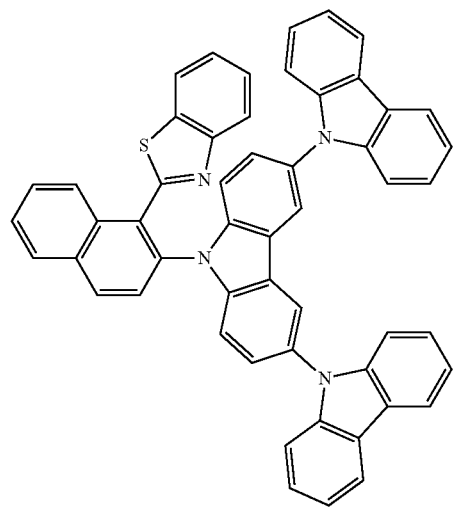
[Chemical Formula A-37]
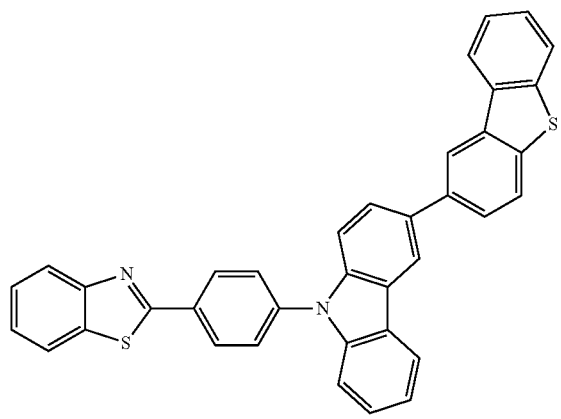
[Chemical Formula A-38]
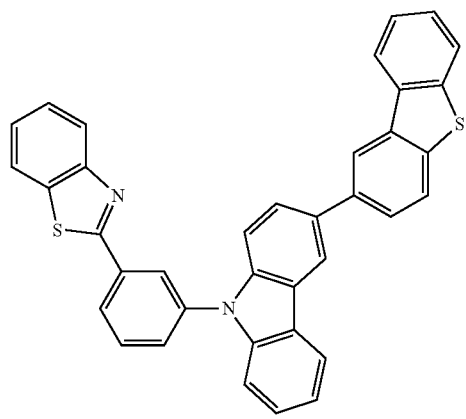

[Chemical Formula A-39]
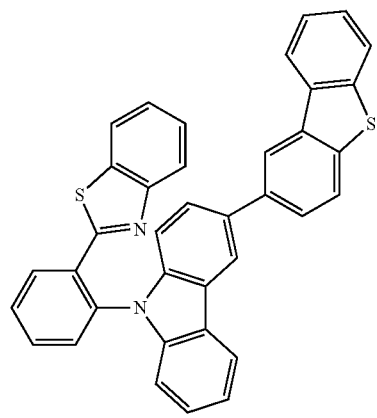
[Chemical Formula A-40]
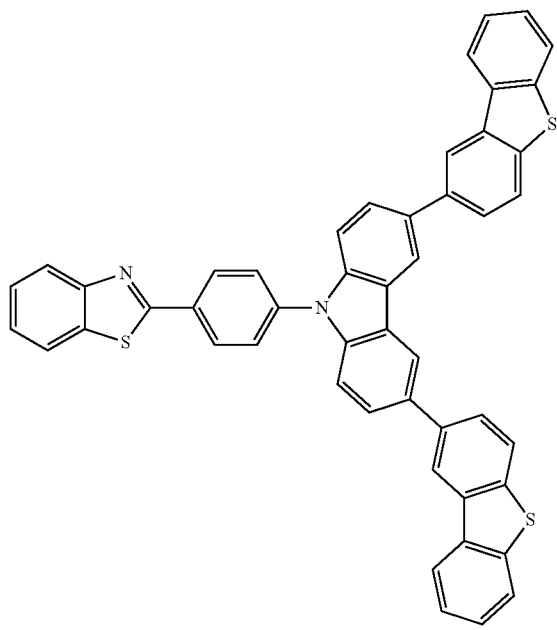
[Chemical Formula A-41]
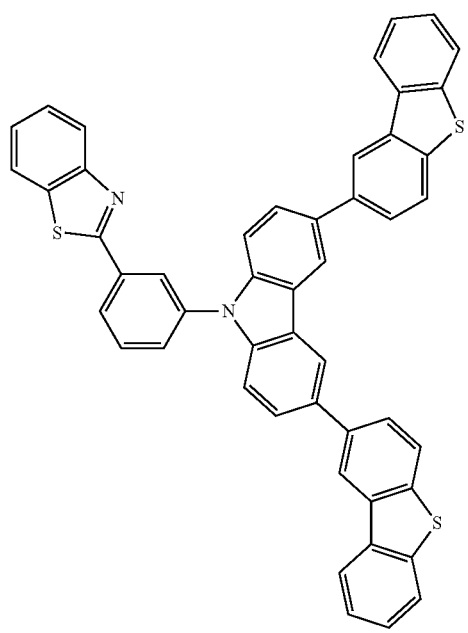
[Chemical Formula A-42]
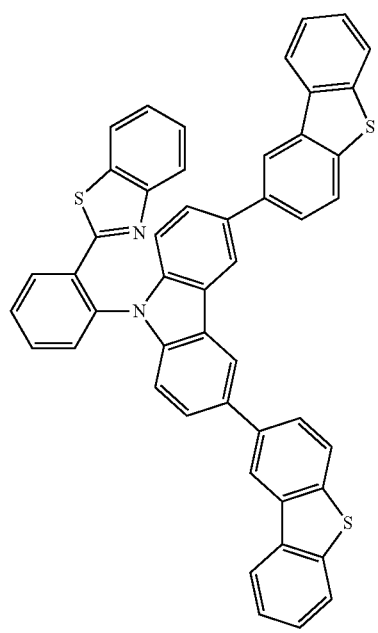

[Chemical Formula A-43]
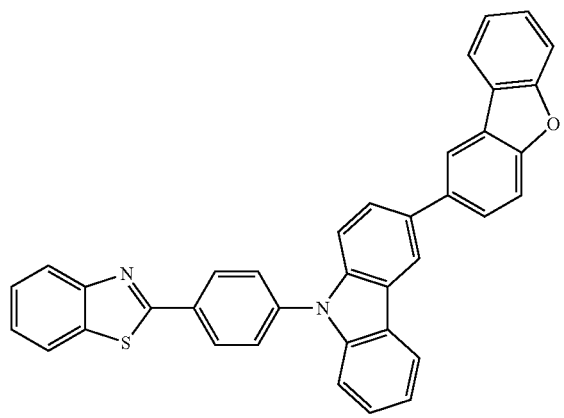
[Chemical Formula A-44]
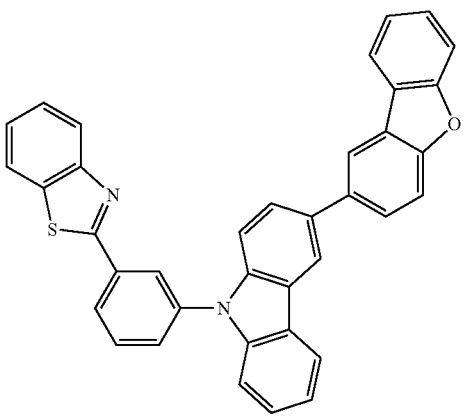
[Chemical Formula A-45]
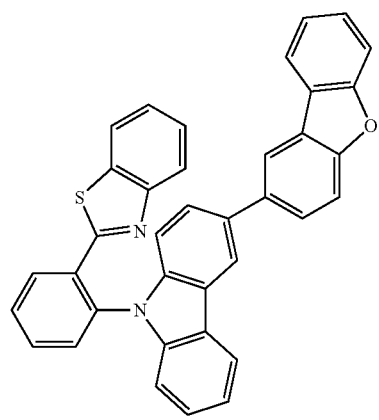
[Chemical Formula A-46]
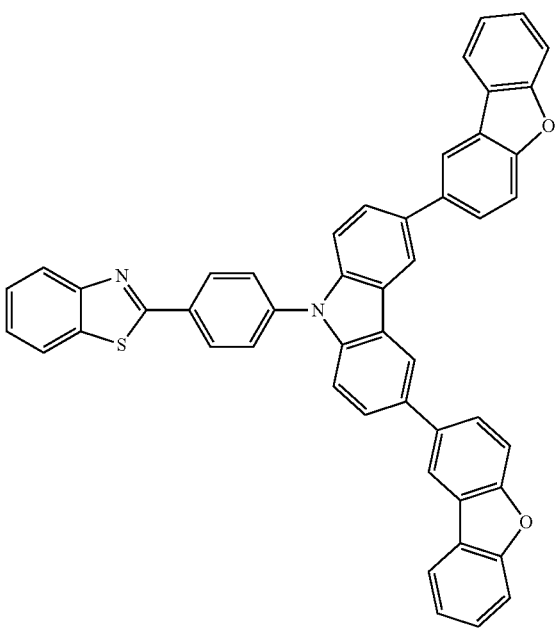

[Chemical Formula A-47]
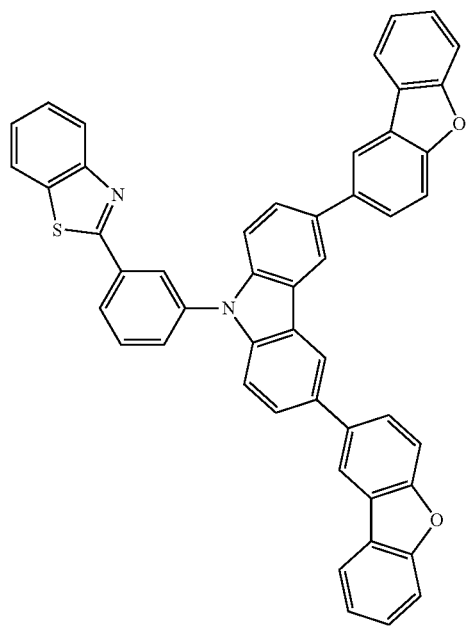
[Chemical Formula A-48]
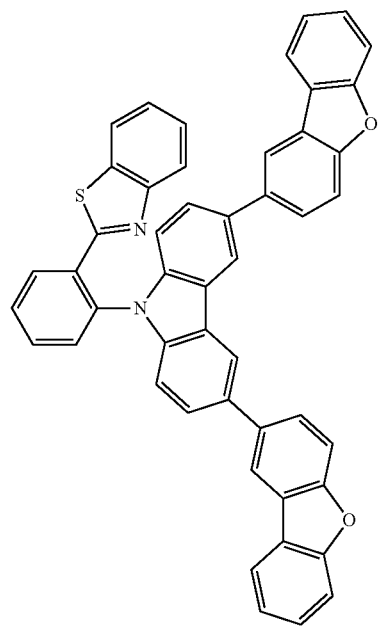
[Chemical Formula A-49]
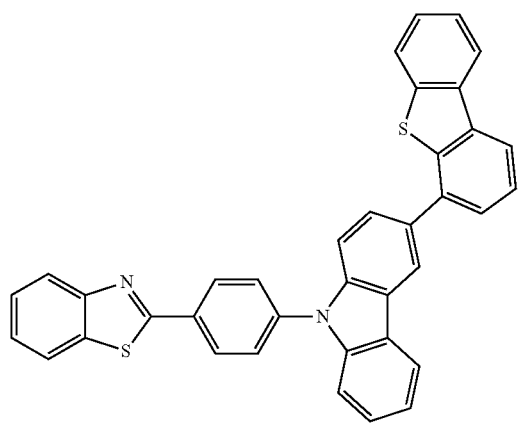
[Chemical Formula A-50]
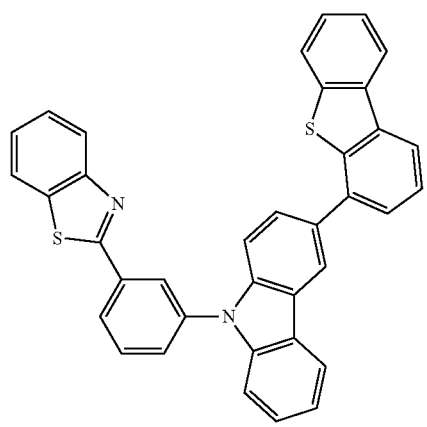

-continued
[Chemical Formula A-51]
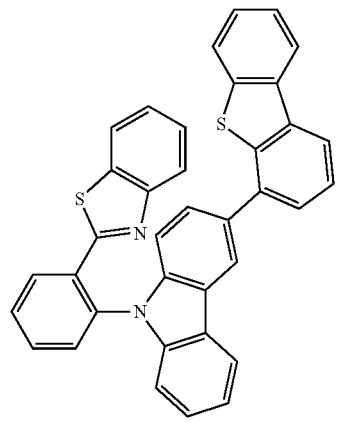
[Chemical Formula A-52]
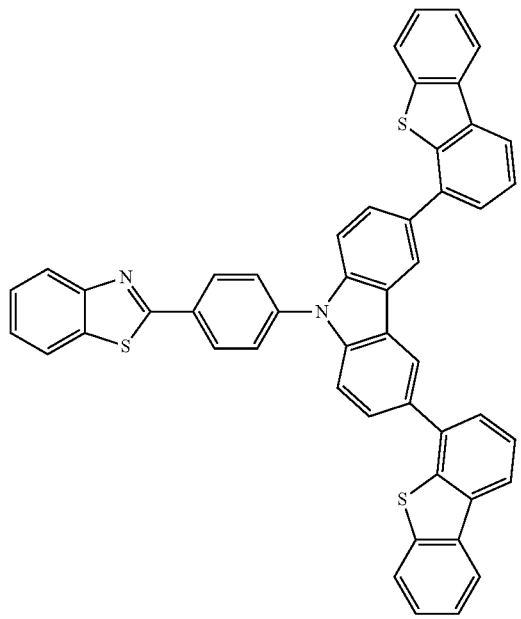
[Chemical Formula A-53]
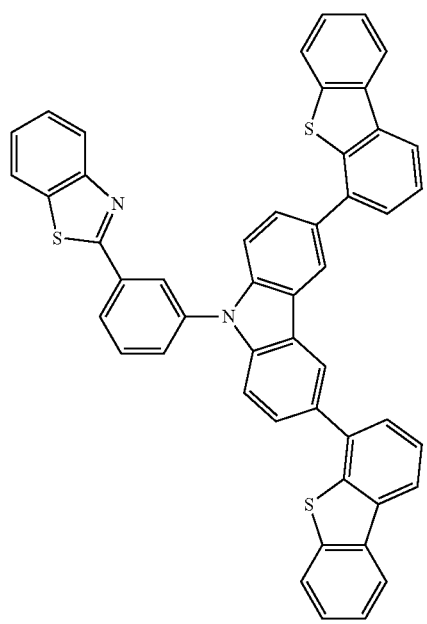
[Chemical Formula A-54]
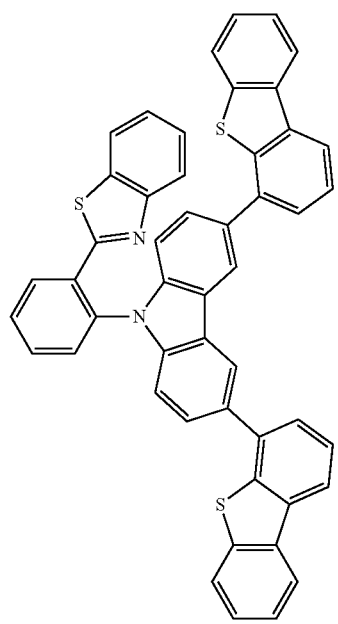

[Chemical Formula A-55]
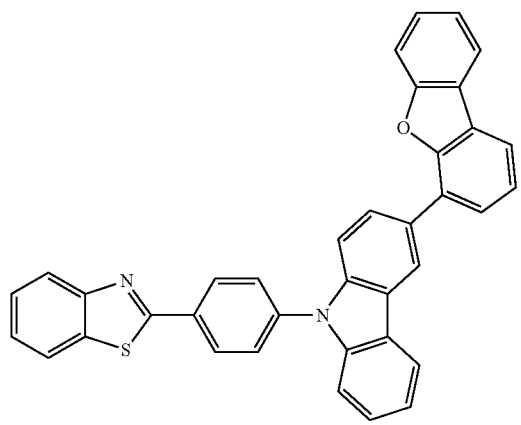
[Chemical Formula A-56]
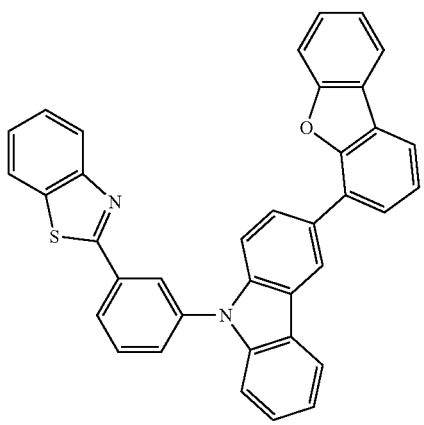
[Chemical Formula A-57]
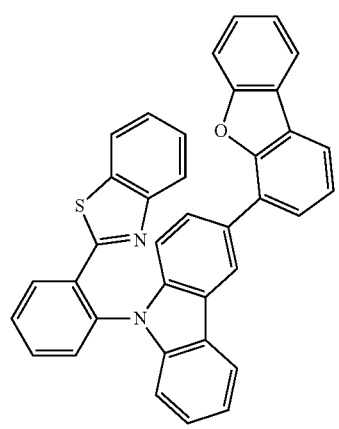
[Chemical Formula A-58]
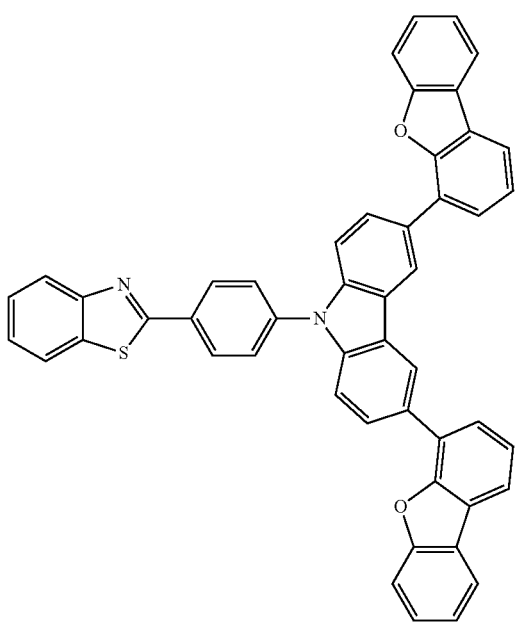

[Chemical Formula A-59]
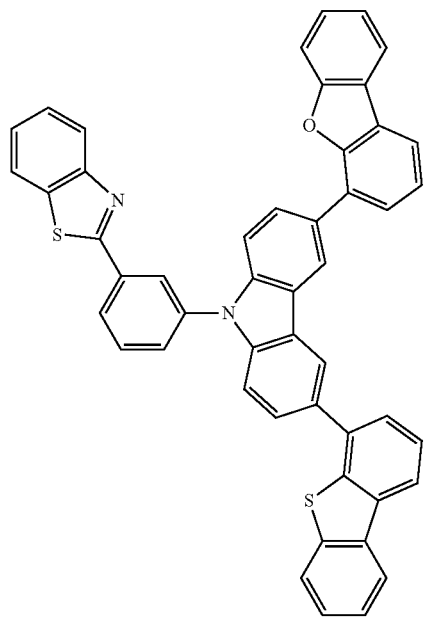
[Chemical Formula A-60]
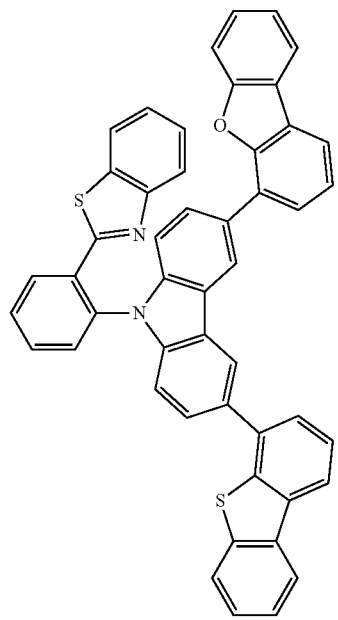
[Chemical Formula A-61]
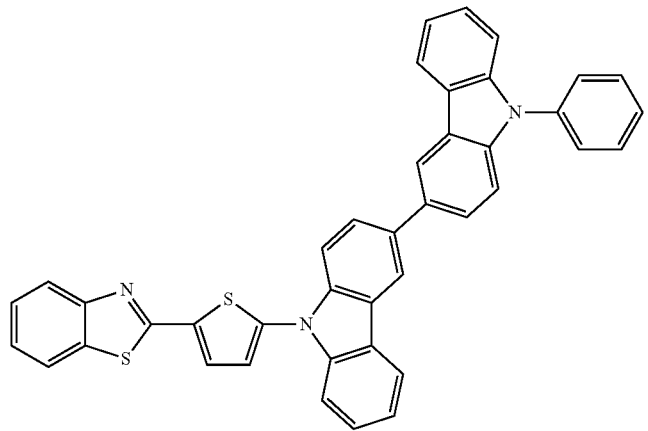
[Chemical Formula A-62]
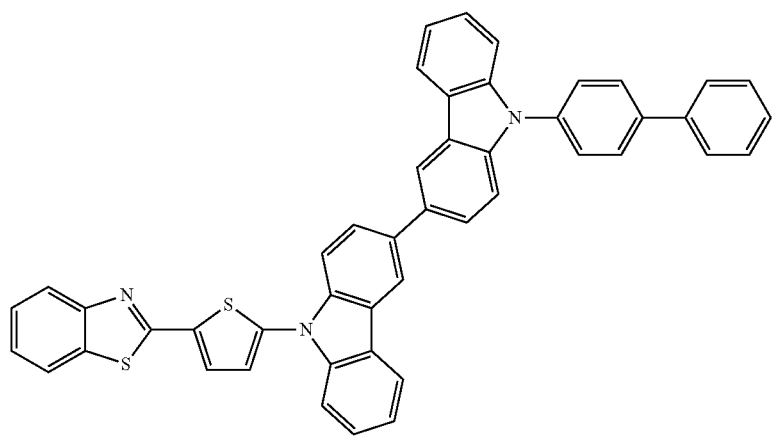

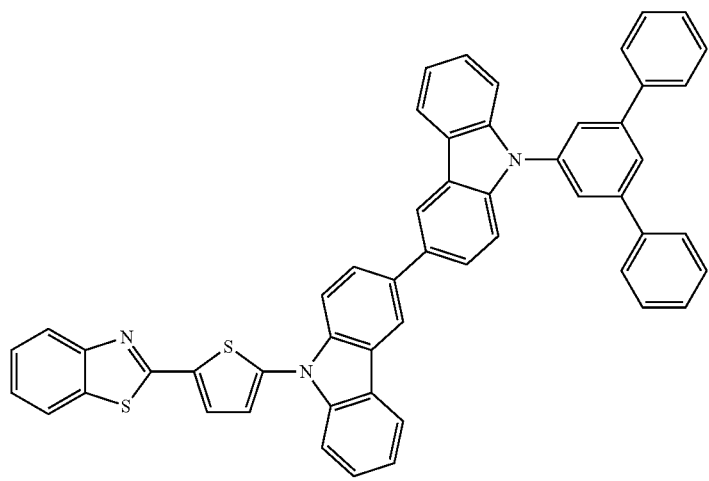
[Chemical Formula A-63]
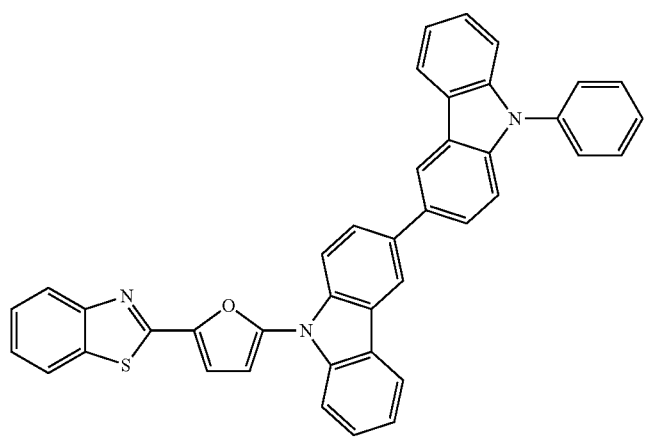
[Chemical Formula A-64]
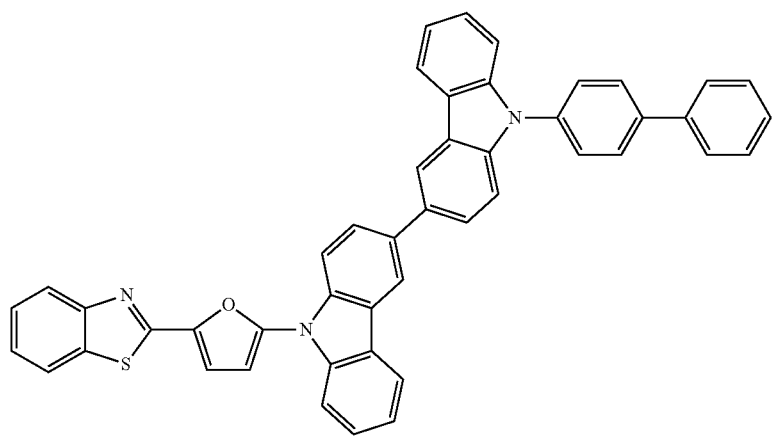
[Chemical Formula A-65]

[Chemical Formula A-66]
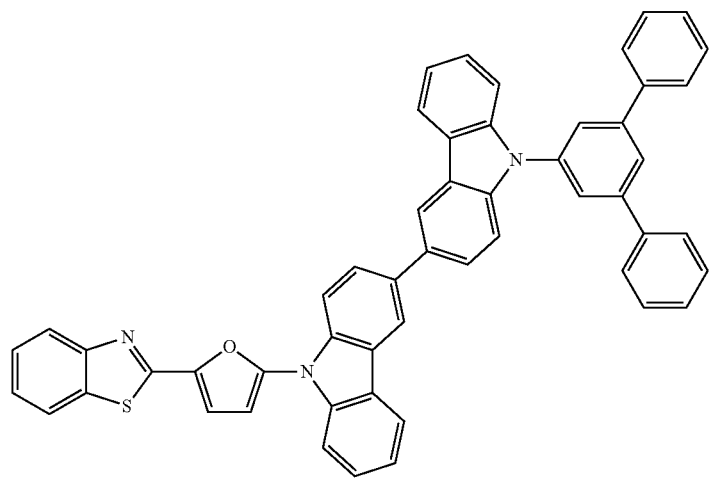
[Chemical Formula A-67]
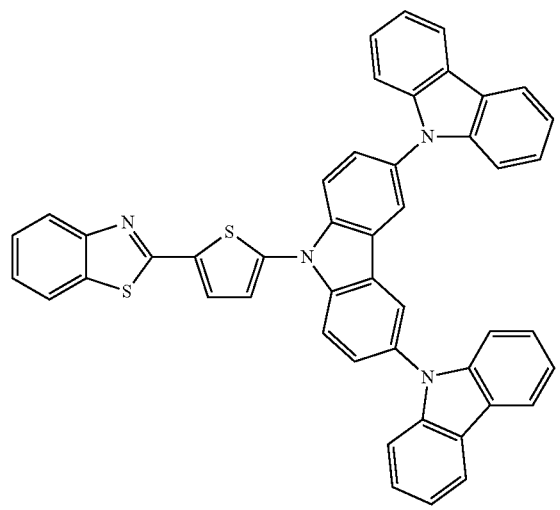
[Chemical Formula A-68]
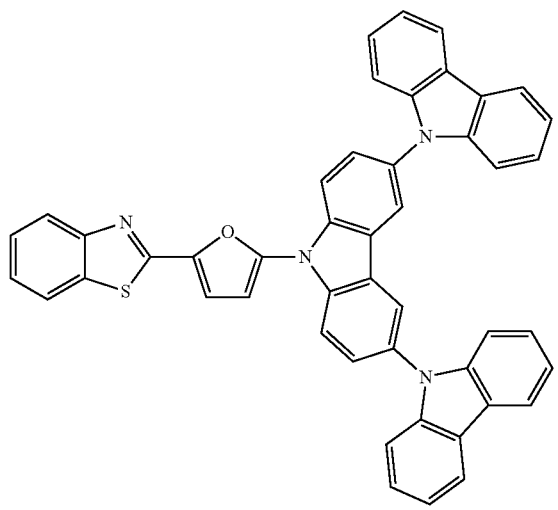
[Chemical Formula A-69]
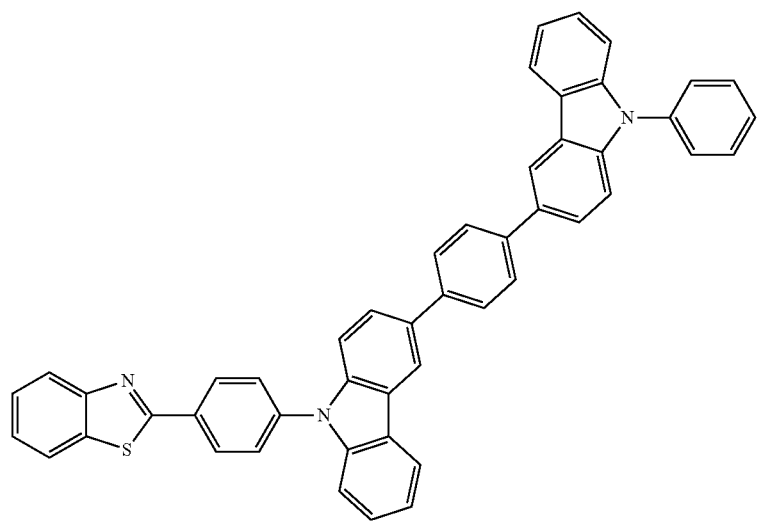

[Chemical Formula A-70]
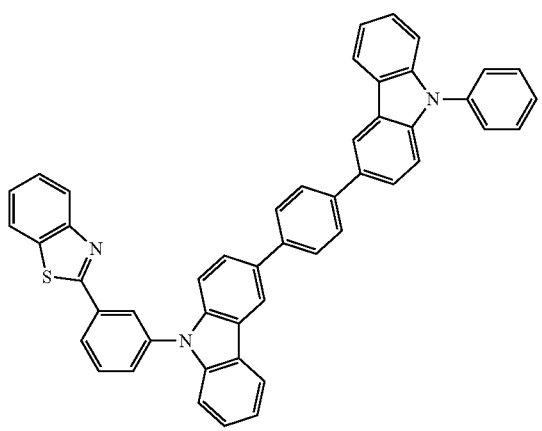
[Chemical Formula A-71]
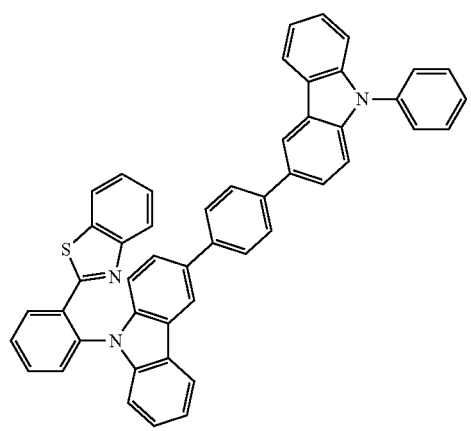
[Chemical Formula A-72]
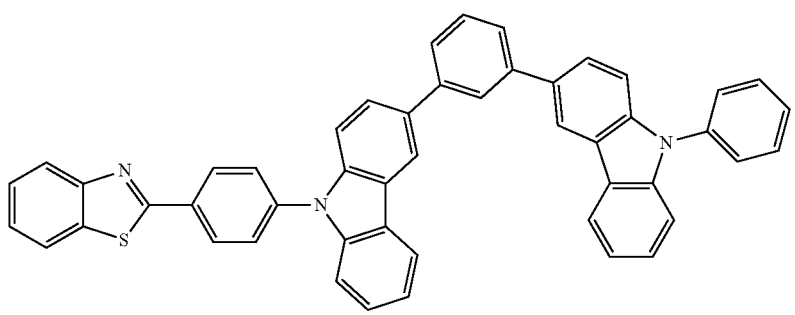
[Chemical Formula A-73]
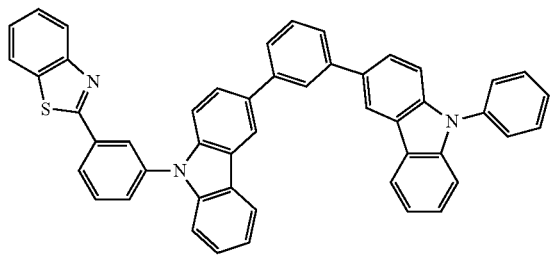
[Chemical Formula A-74]
The compound for an organic optoelectronic device according to one embodiment of the present invention may be one of compounds represented by the following Chemical Formulae B-1 to B-8.
[Chemical Formula B-1]
[Chemical Formula B-2]
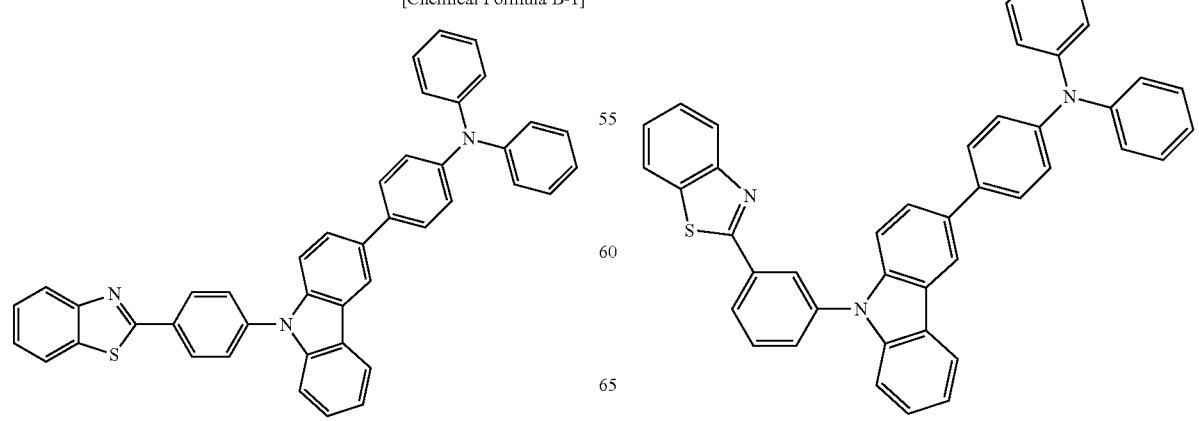

[Chemical Formula B-3]
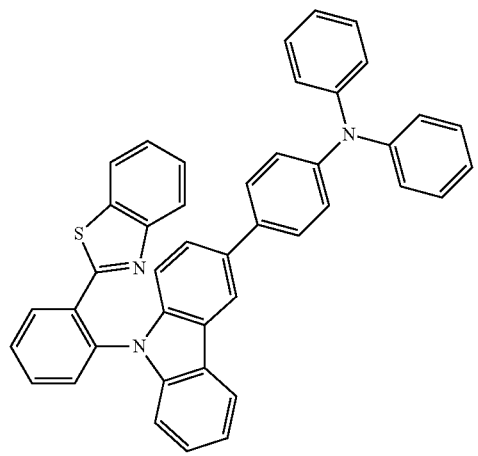
[Chemical Formula B-6]
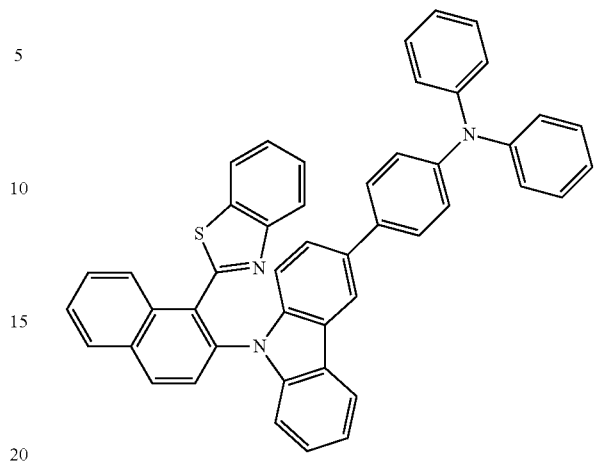
[Chemical Formula B-4]
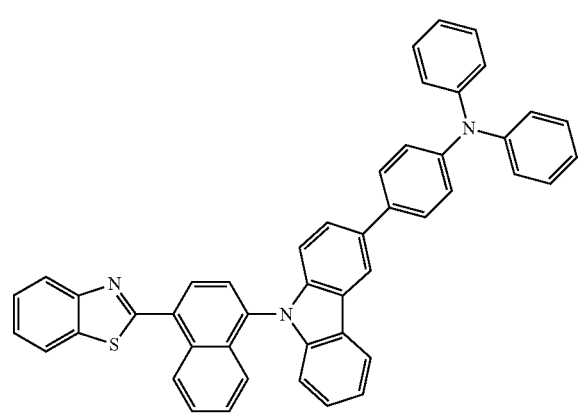
[Chemical Formula B-7]
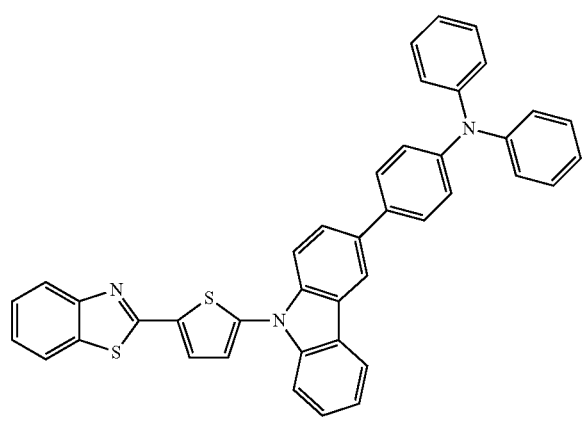
[Chemical Formula B-5]
[Chemical Formula B-8]
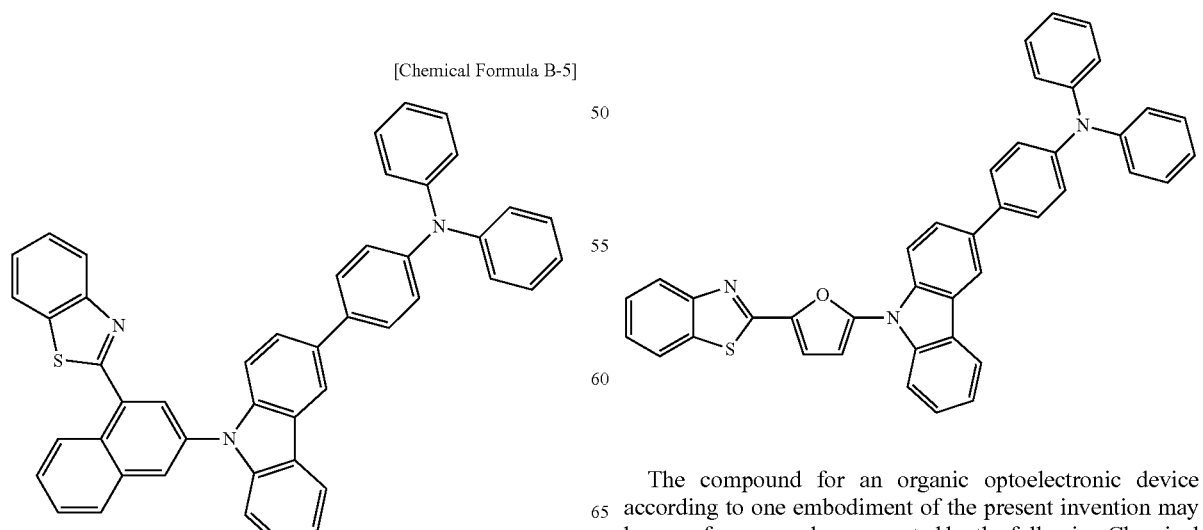
The compound for an organic optoelectronic device according to one embodiment of the present invention may be one of compounds represented by the following Chemical Formulae C-1 to C-45.

[Chemical Formula C-1]
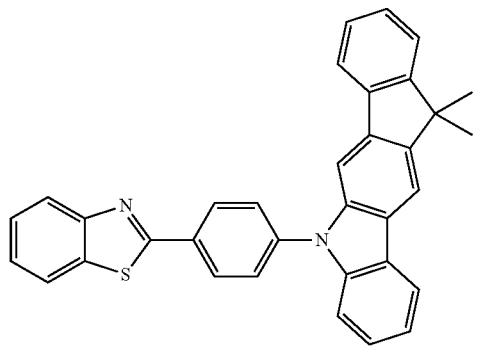
[Chemical Formula C-2]
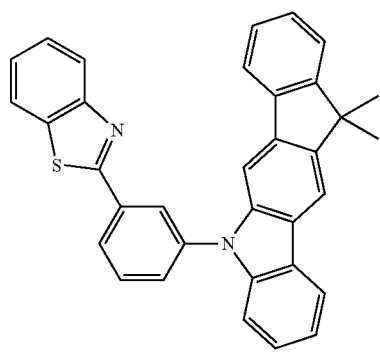
[Chemical Formula C-3]
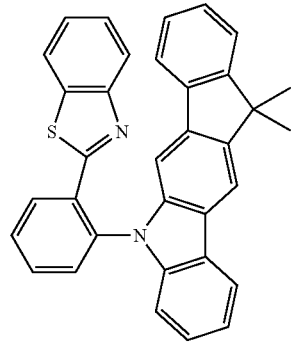
[Chemical Formula C-4]
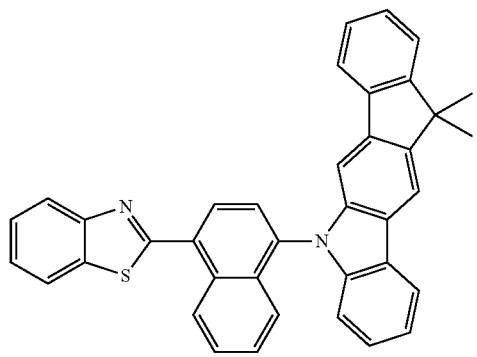
[Chemical Formula C-5]
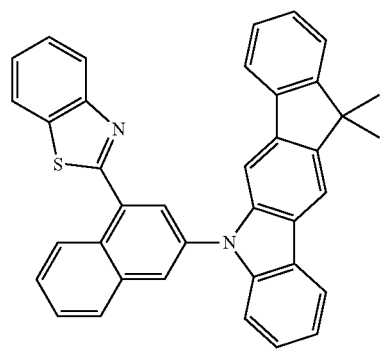
[Chemical Formula C-6]
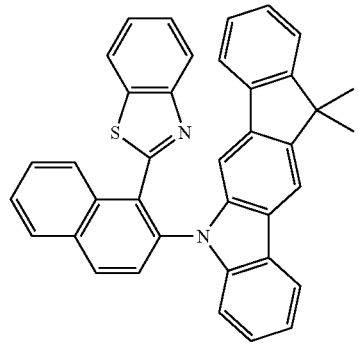
[Chemical Formula C-7]
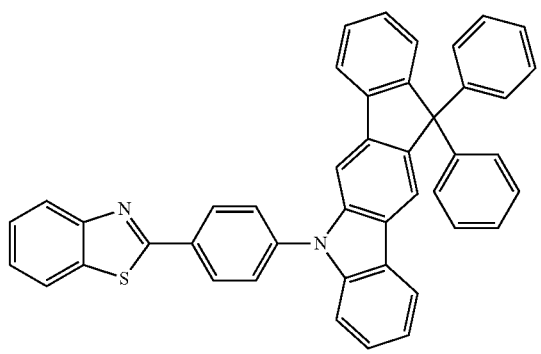
[Chemical Formula C-8]
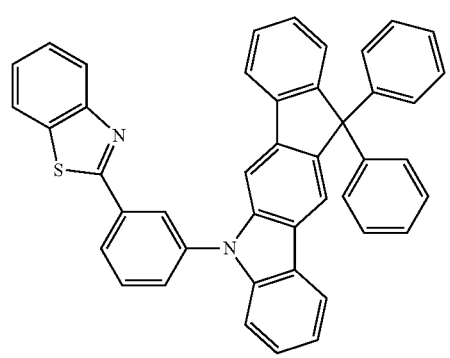

[Chemical Formula C-9]
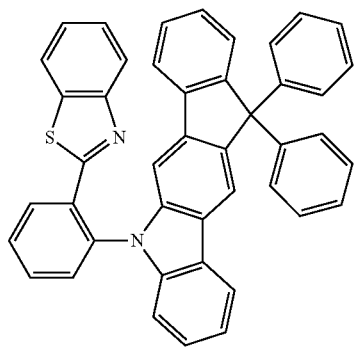
[Chemical Formula C-10]
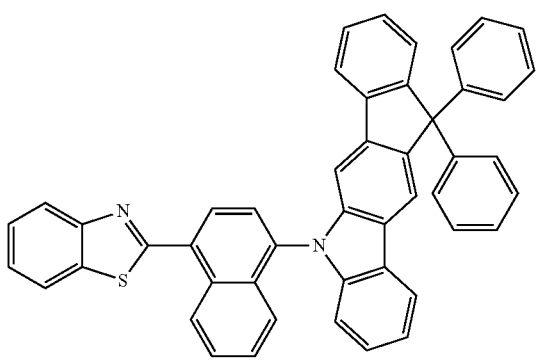
[Chemical Formula C-11]
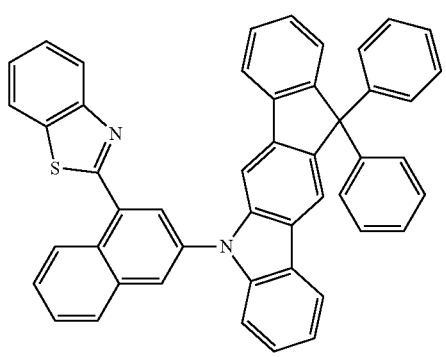
[Chemical Formula C-12]
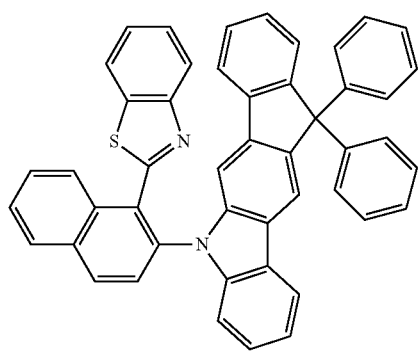
[Chemical Formula C-13]
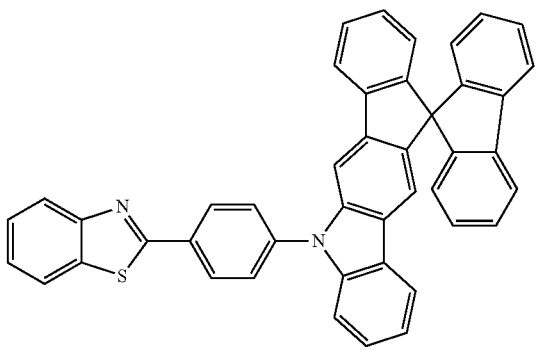
[Chemical Formula C-14]
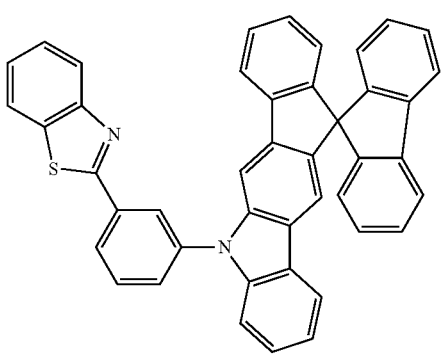
[Chemical Formula C-15]
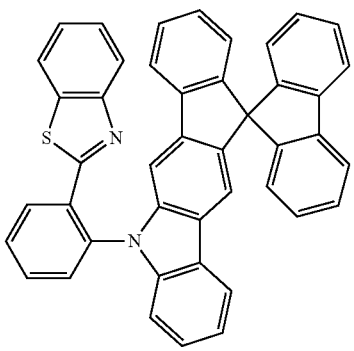
[Chemical Formula C-16]
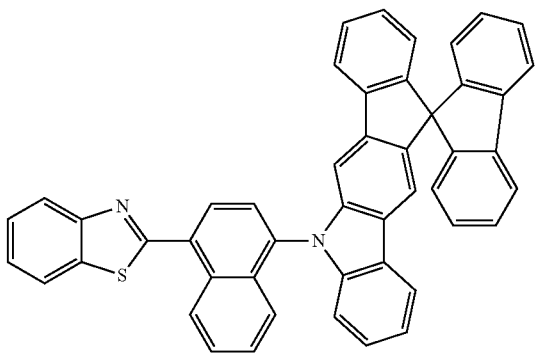

[Chemical Formula C-17]
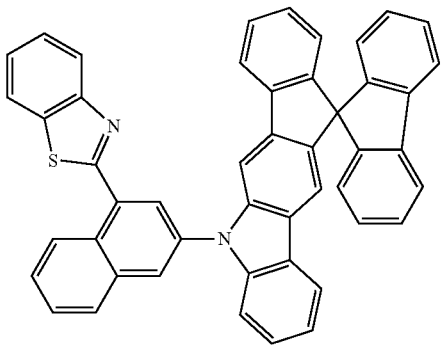
[Chemical Formula C-18]
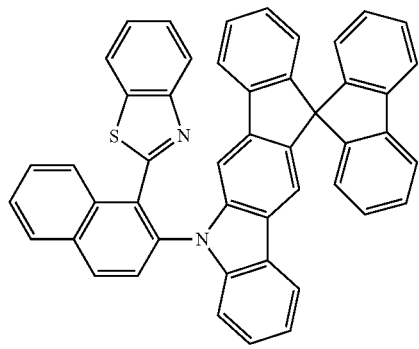
[Chemical Formula C-19]
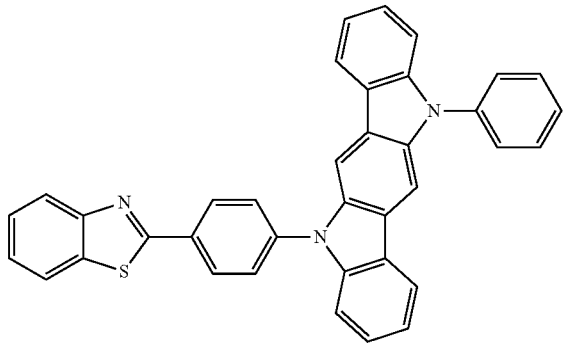
[Chemical Formula C-20]
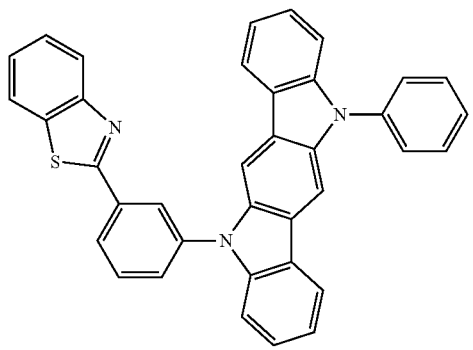
[Chemical Formula C-21]
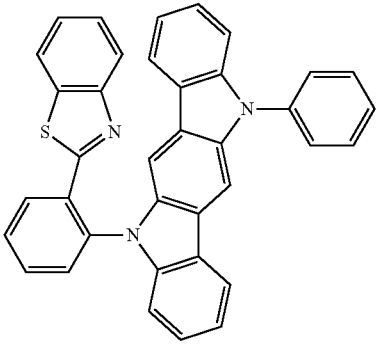
[Chemical Formula C-22]
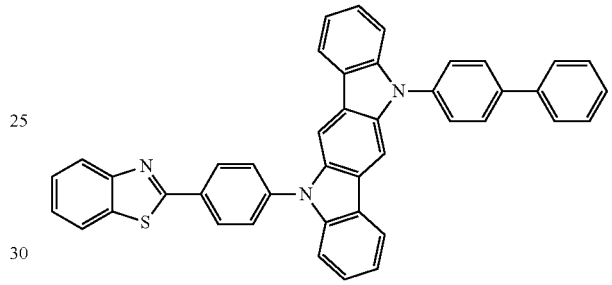
[Chemical Formula C-23]
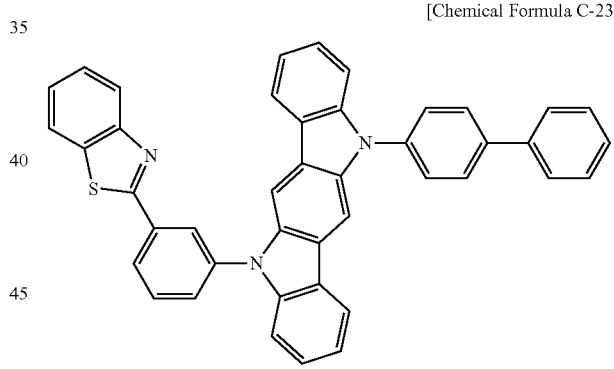
[Chemical Formula C-24]
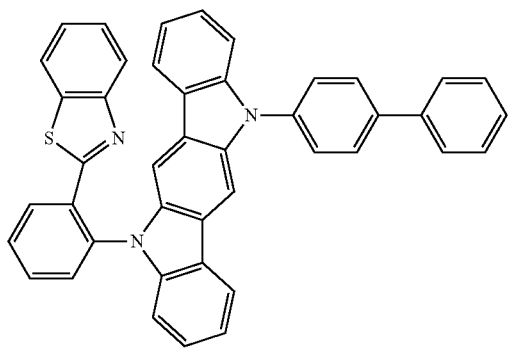

-continued
[Chemical Formula C-25]
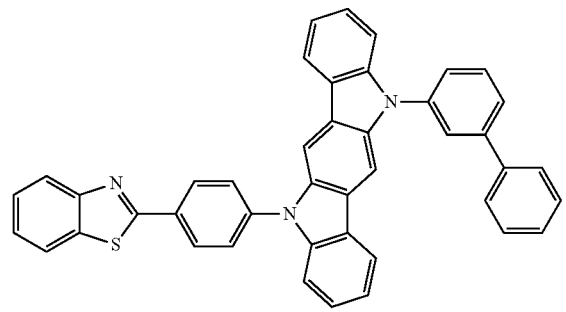
[Chemical Formula C-26]
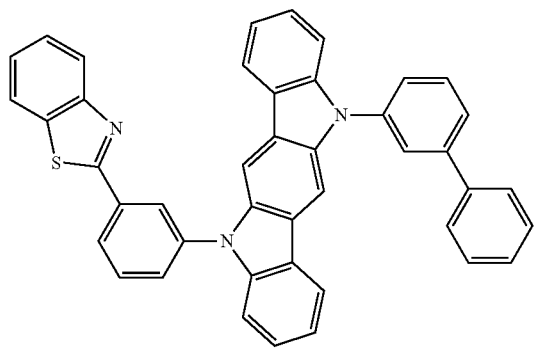
[Chemical Formula C-27]
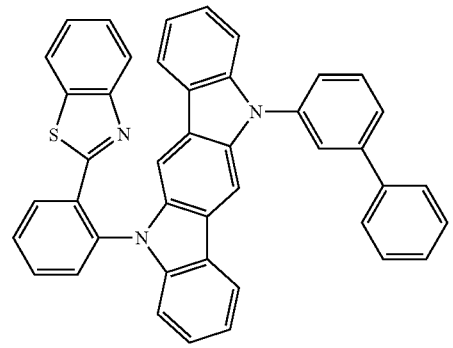
[Chemical Formula C-28]
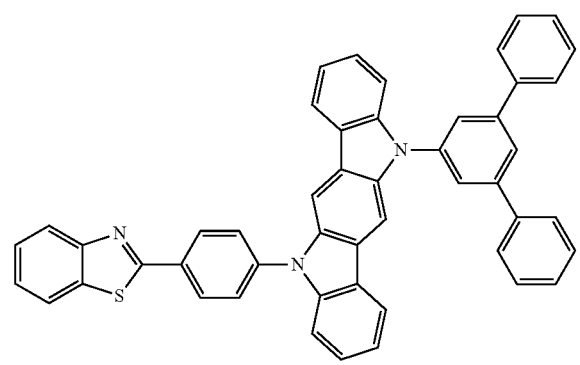
[Chemical Formula C-29]
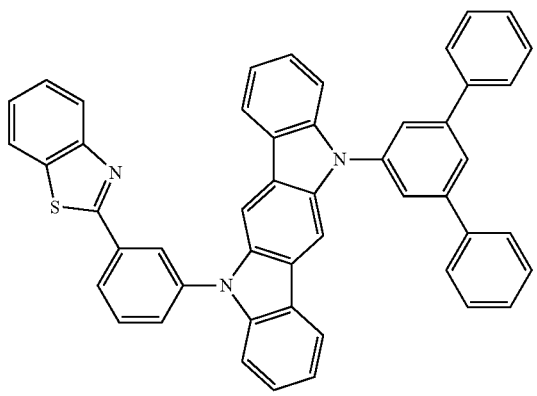
[Chemical Formula C-30]
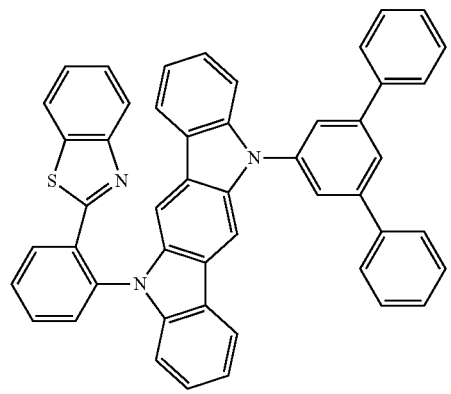
[Chemical Formula C-31]
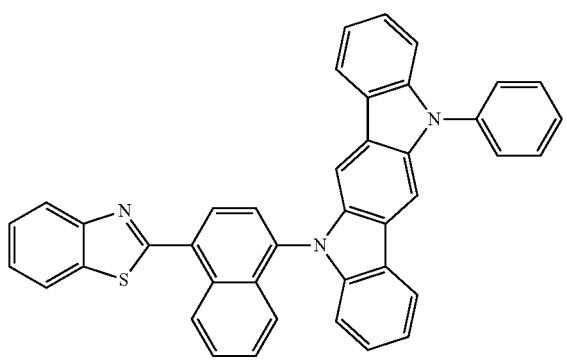
[Chemical Formula C-32]
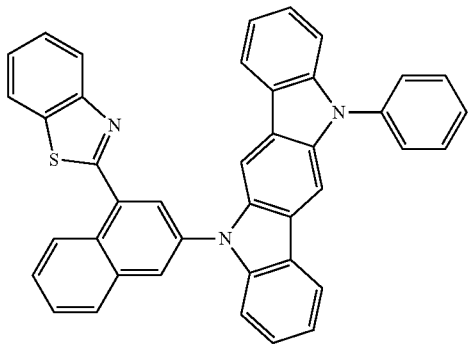

[Chemical Formula C-33]
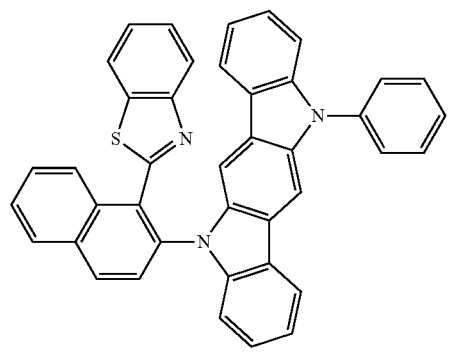
[Chemical Formula C-37]
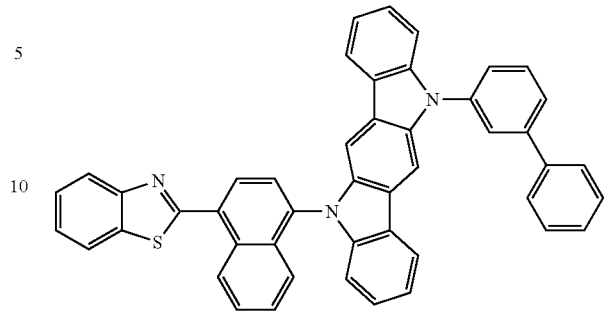
[Chemical Formula C-34]
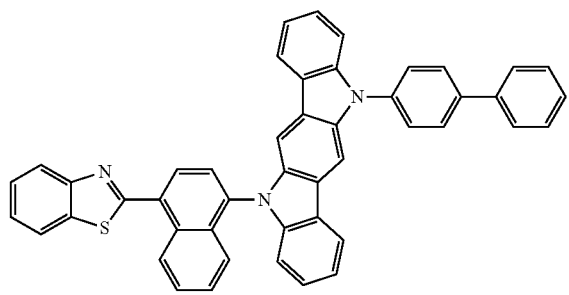
[Chemical Formula C-38]
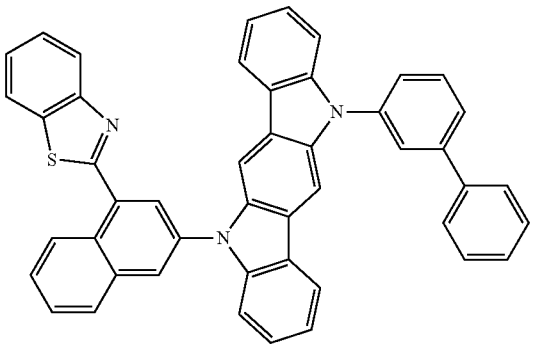
[Chemical Formula C-35]
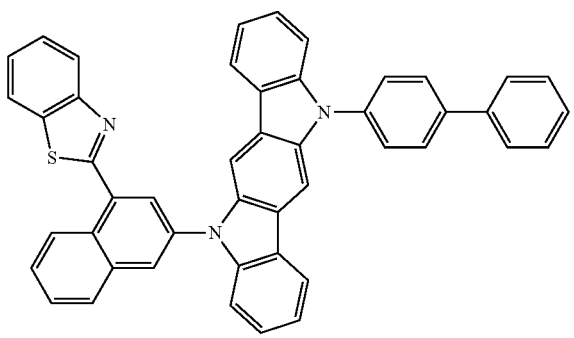
[Chemical Formula C-39]
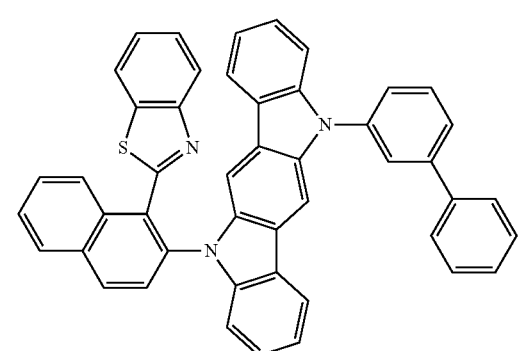
[Chemical Formula C-36]
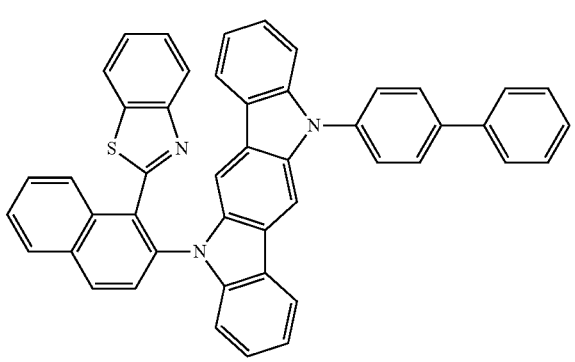
[Chemical Formula C-40]
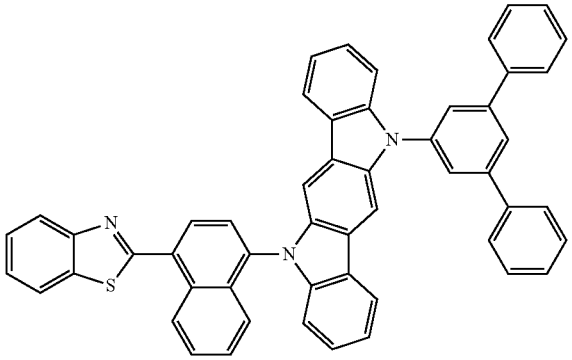

[Chemical Formula C-41]
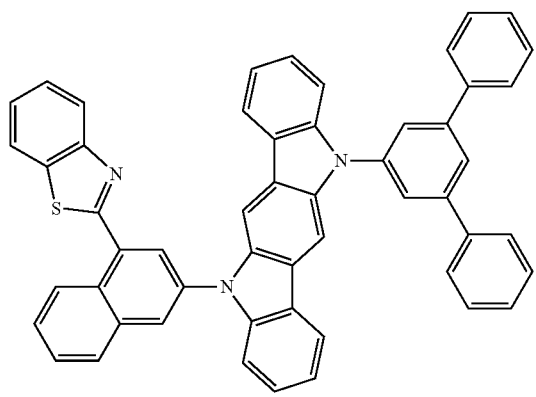
[Chemical Formula C-42]
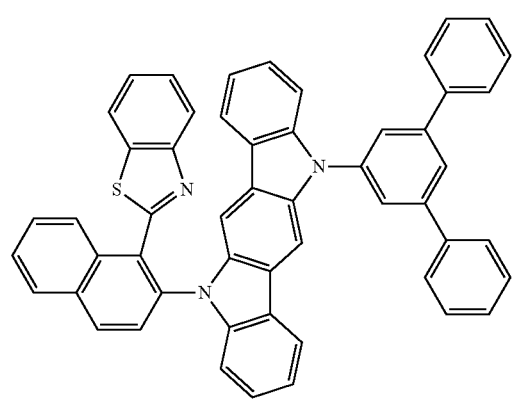
[Chemical Formula C-43]
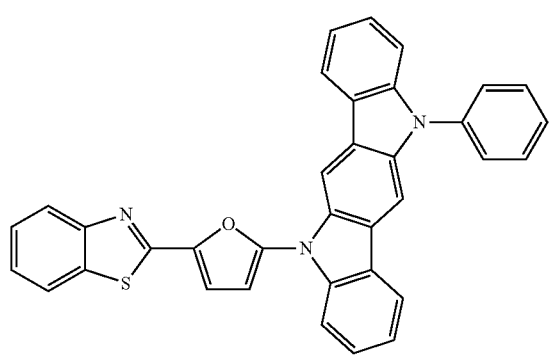
[Chemical Formula C-44]
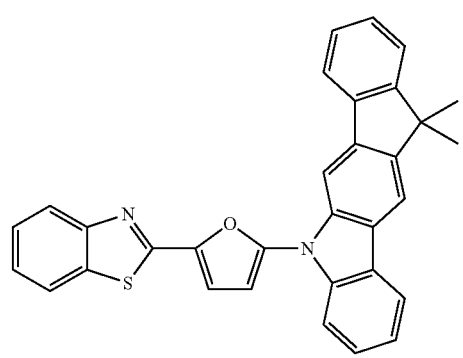
[Chemical Formula C-45]
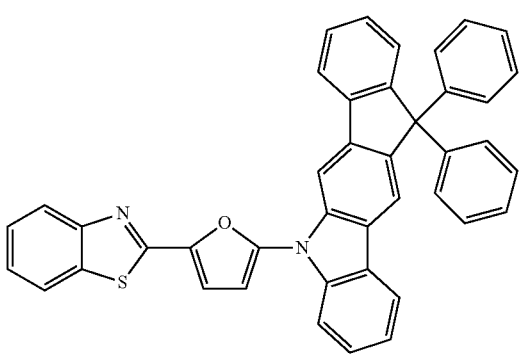
The compound for an organic optoelectronic device according to one embodiment of the present invention may be one of compounds represented by the following Chemical Formulae D-1 to D-8.
[Chemical Formula D-1]
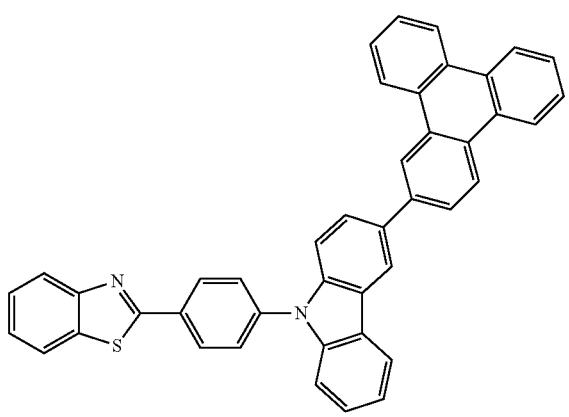
[Chemical Formula D-2]
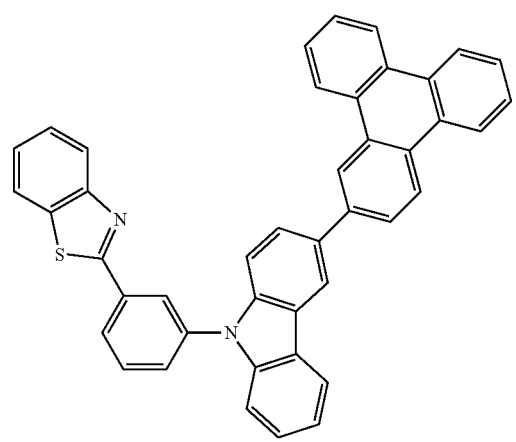

[Chemical Formula D-3]

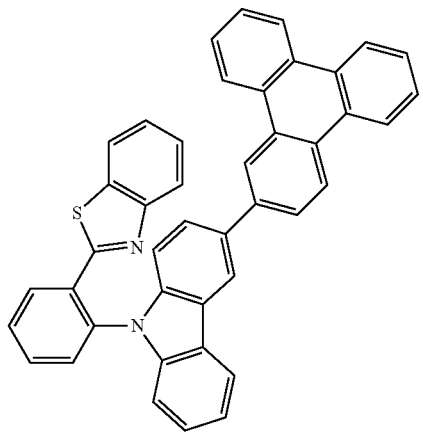

[Chemical Formula D-4]

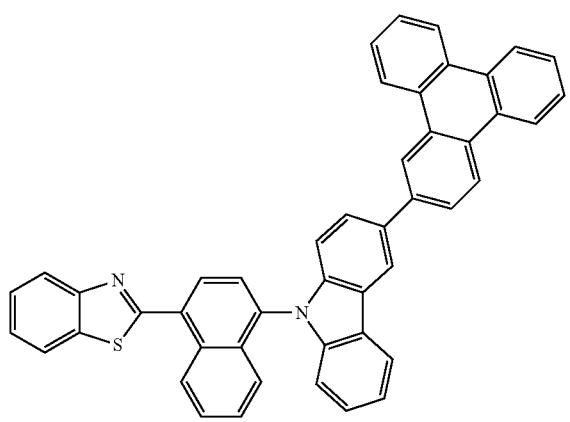

[Chemical Formula D-5]

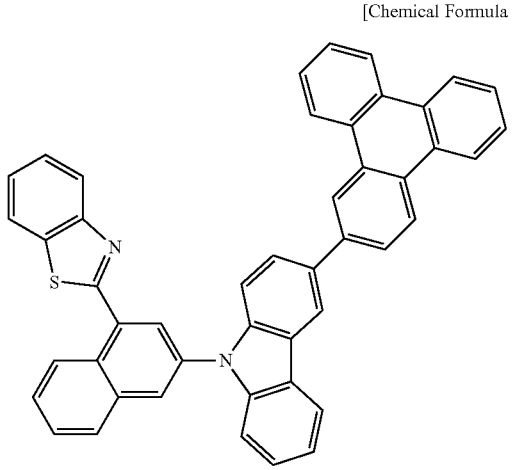

[Chemical Formula D-6]

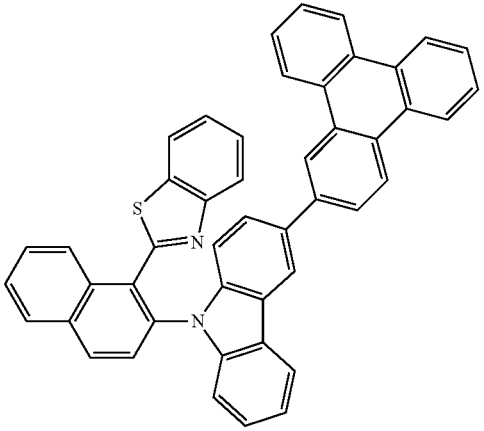

[Chemical Formula D-7]

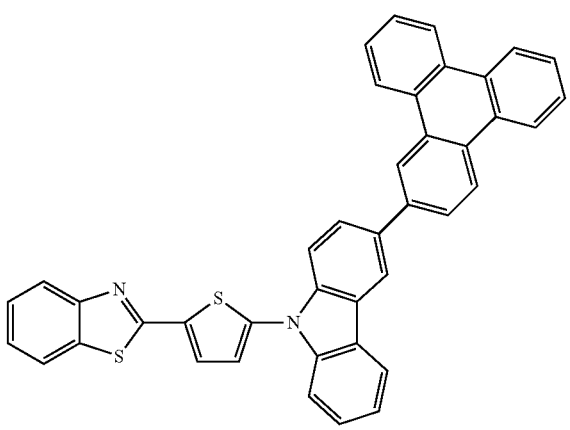

[Chemical Formula D-8]

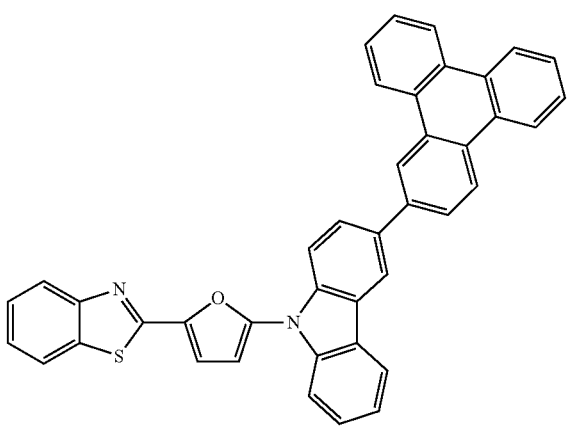

When the above compound according to one embodiment of the present invention requires both electron and hole characteristics, the functional group having electron characteristics may be introduced to effectively improve lifespan of an organic light emitting diode and decreasing its driving voltage.

The above compound for an organic optoelectronic device according to one embodiment of the present invention shows a maximum light emitting wavelength in a range of about 320 to about 500 nm, high triplet exciton energy (T1) of greater than equal to about 2.0 eV and specifically, about 2.0 to about 4.0 eV and thus, has an advantage of increasing luminous efficiency of a to dopant by well transporting charges of a host having high triplet exciton energy to the dopant and decreasing a driving voltage by freely adjusting HOMO and LUMO energy levels of a material and accordingly, may be used as a host material or a charge transport material.

In addition, the compound for an organic optoelectronic device has optical and electrical activity and thus, may be used as a non-linear optical material, an electrode material, an electrochromic material, an optical switch, a sensor, a module, a wave guide, an organic transistor, a laser, an optical absorbing material, a dielectric material, and a material for a separation membrane and the like.

The compound for an organic optoelectronic device including the above compounds has a glass transition temperature of greater than or equal to about 90° C. and a thermal decomposition temperature of greater than or equal to about 400° C., indicating improved thermal stability. Thereby, it is possible to produce an organic optoelectronic device having a high efficiency.

The compound for an organic optoelectronic device including the above compounds may play a role for emitting light or injecting and/or transporting electrons, and also act as a light emitting host with an appropriate dopant. In other words, the compound for an organic optoelectronic device may be used as a phosphorescent or fluorescent host material, a blue light emitting dopant material, or an electron transport material.

The compound for an organic optoelectronic device according to one embodiment of the present invention is used for an organic thin layer, and it may improve the life-span characteristics, efficiency characteristics, electrochemical stability, and thermal stability of an organic optoelectronic device and decrease the driving voltage.

Therefore, according to another embodiment, an organic optoelectronic device that includes the compound for an organic optoelectronic device is provided. The organic optoelectronic device may include an organic photoelectric device, an organic light emitting diode, an organic solar cell, an organic transistor, an organic photo-conductor drum, an organic memory device, and the like. For example, the compound for an organic optoelectronic device according to one embodiment may be included in an electrode or an electrode buffer layer in the organic solar cell to improve the quantum efficiency, and it may be used as an electrode material for a gate, a source-drain electrode, or the like in the organic transistor.

Hereinafter, an organic light emitting diode is specifically described.

An organic light emitting diode according to another embodiment of the present invention includes an anode, a cathode, and at least one or more organic thin layer between the anode and the cathode, and at least one of the organic thin layers may include the compound for an organic optoelectronic device according to one embodiment of the present invention.

The organic thin layer including the compound for an organic optoelectronic device may include a layer selected from an emission layer, a hole transport layer, a hole injection layer, an electron transport layer, an electron injection layer, a hole blocking layer, and a combination thereof. The at least one layer includes the compound for an organic optoelectronic device according to one embodiment. Particularly, the compound for an organic optoelectronic device according to one embodiment may be included in an electron transport layer or electron injection layer. In addition, when the compound for an organic optoelectronic device is included in the emission layer, the compound for an organic optoelectronic device may be included as a phosphorescent or fluorescent host, and particularly, as a fluorescent blue dopant material.

FIGS. 1 to 5 are cross-sectional views showing organic light emitting diodes including the compound for an organic optoelectronic device according to one embodiment of the present invention.

Referring to FIGS. 1 to 5, organic light emitting diodes 100, 200, 300, 400, and 500 according to one embodiment include at least one organic thin layer 105 interposed between an anode 120 and a cathode 110.

The anode 120 includes an anode material having a large work function to help hole injection into an organic thin layer. Specific examples of the anode material include: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combined metal and oxide such as ZnO:Al or $SnO_2$:Sb; or a conductive polymer such as poly(3-methylthiophene), poly[3,4-(ethylene-1,2-dioxy) thiophene] (PEDT), polypyrrole, and polyaniline, but is not limited thereto. It is preferable to include a transparent electrode including indium tin oxide (ITO) as an anode.

The cathode 110 includes a cathode material having a small work function to help electron injection into an organic thin layer. Specific examples of the cathode material include: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2$/Al, LiF/Ca, LiF/Al, and $BaF_2$/Ca, but is not limited thereto. It is preferable to include a metal electrode including aluminum as a cathode.

First, referring to FIG. 1, the organic light emitting diode 100 includes an organic thin layer 105 including only an emission layer 130.

Figure 2:
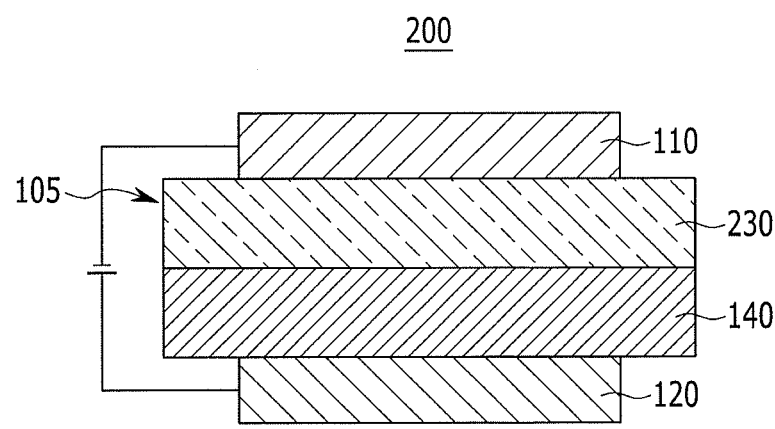

Referring to FIG. 2, a double-layered organic light emitting diode 200 includes an organic thin layer 105 including an emission layer 230 including an electron transport layer (ETL), and a hole transport layer (HTL) 140. As shown in FIG. 2, the organic thin layer 105 includes a double layer of the emission layer 230 and hole transport layer (HTL) 140. The emission layer 130 also functions as an electron transport layer (ETL), and the hole transport layer (HTL) 140 layer has an excellent binding property with a transparent electrode such as ITO or an excellent hole transport capability.

Figure 3:
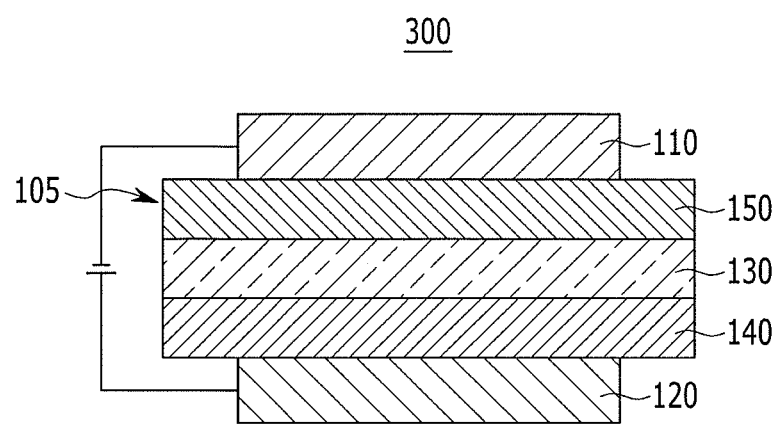

Referring to FIG. 3, a three-layered organic light emitting diode 300 includes an organic thin layer 105 including an electron transport layer (ETL) 150, an emission layer 130, and a hole transport layer (HTL) 140. The emission layer 130 is independently installed, and layers having an excellent electron transport capability or an excellent hole transport capability are separately stacked.

Figure 4:
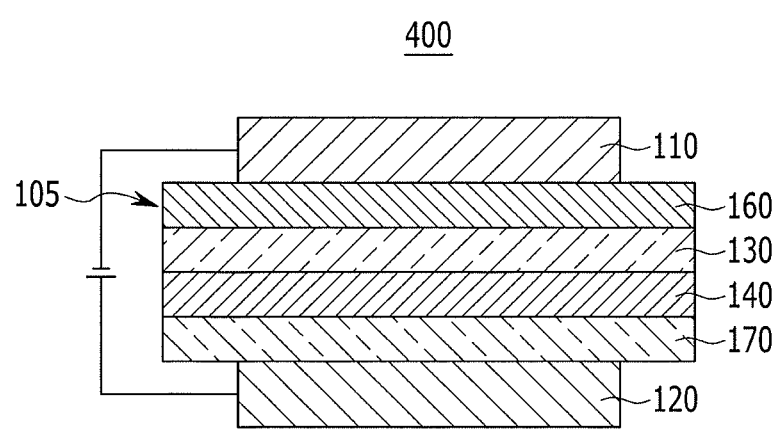

As shown in FIG. 4, a four-layered organic light emitting diode 400 includes an organic thin layer 105 including an electron injection layer (EIL) 160, an emission layer 130, a hole transport layer (HTL) 140, and a hole injection layer (HIL) 170 for adherence with the cathode of ITO.

Figure 5:
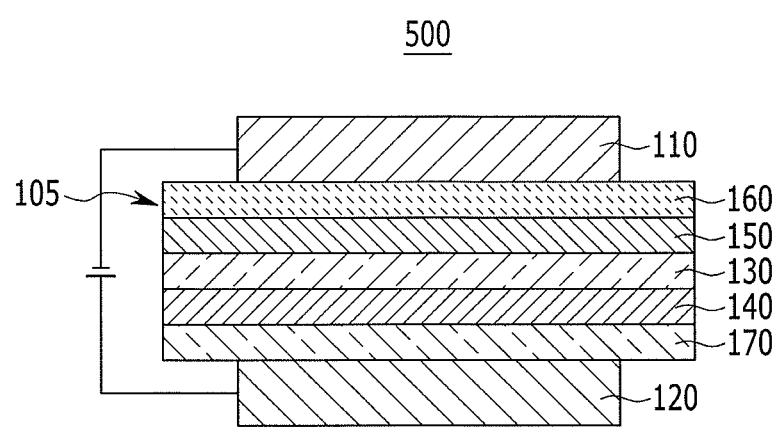

As shown in FIG. 5, a five-layered organic light emitting diode 500 includes an organic thin layer 105 including an electron transport layer (ETL) 150, an emission layer 130, a hole transport layer (HTL) 140, and a hole injection layer (HIL) 170, and further includes an electron injection layer (EIL) 160 to achieve a low voltage.

In FIGS. 1 to 5, the organic thin layer 105 including at least one selected from the group consisting of an electron transport layer (ETL) 150, an electron injection layer (EIL) 160, emission layers 130 and 230, a hole transport layer (HTL) 140, a hole injection layer (HIL) 170, and combinations thereof includes the compound for an organic optoelectronic device. The compound for an organic optoelectronic device may be used for an electron transport layer (ETL) 150 including the electron transport layer (ETL) 150 or electron injection layer (EIL) 160. When it is used for the electron transport layer (ETL), it is possible to provide an organic light emitting diode having a more simple structure because it does not require an additional hole blocking layer (not shown).

Furthermore, when the compound for an organic optoelectronic device is included in the emission layers 130 and 230, the compound for an organic optoelectronic device may be included as a phosphorescent or fluorescent host or a fluorescent blue dopant.

The organic light emitting diode may be manufactured by: forming an anode on a substrate; forming an organic thin layer in accordance with a dry coating method such as evaporation, sputtering, plasma plating, and ion plating or a wet coating method such as spin coating, dipping, and flow coating; and providing a cathode thereon.

Another embodiment of the present invention provides a display device including the light emitting diode according to the above embodiment.

MODE FOR INVENTION

Hereinafter, the embodiments are illustrated in more detail with reference to examples. These examples, however, should not in any sense be interpreted as limiting the scope of the present invention.

Preparation of Compound for Organic Optoelectronic Device

Example 1: Synthesis of Compound Represented by Chemical Formula A-1

A compound represented by the above formula A-1 as specific examples of a compound for an organic optoelectronic device according to the present invention was synthesized in a method of the following reaction scheme 1.

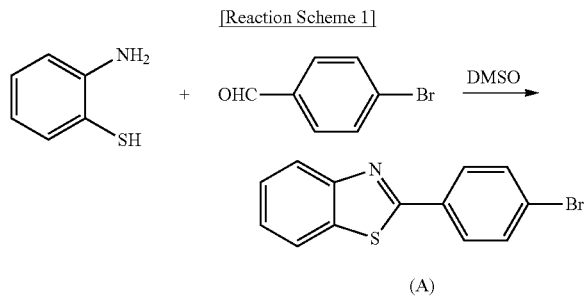

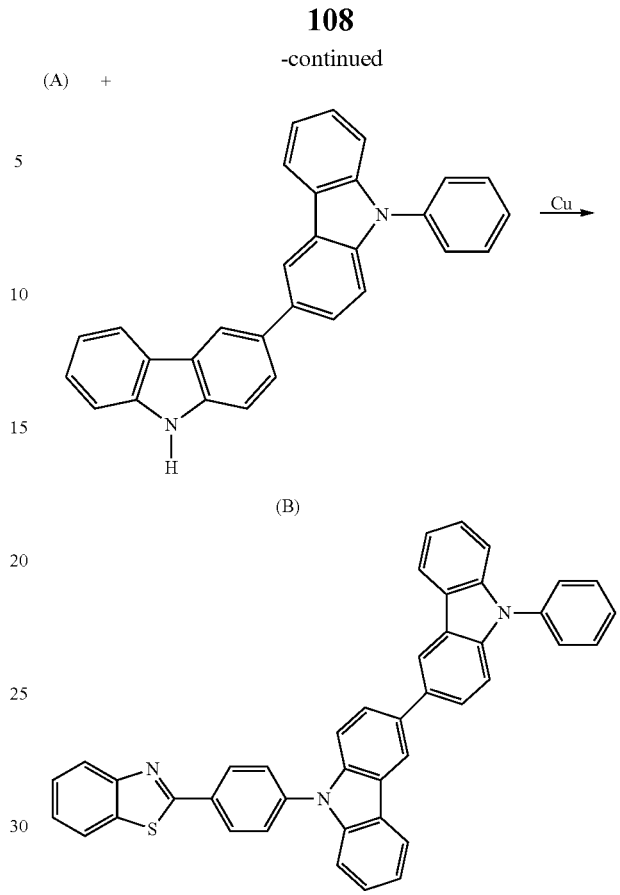

First Step: Synthesis of Compound (A)

37 g (0.3 mol) of 2-amino thiophenol, 50 g (0.27 mol) of 4-bromo benzaldehyde were agitated with 400 mL of dimethyl sulfoxide in a 1000 mL round flask, while the flask was heated up to a reflux temperature, and then, the mixture was agitated for 25 hours. The reaction solution was treated with water to produce a solid, the solid was dissolved in methylene chloride again, and then, moisture therein was removed by using anhydrous magnesium sulfate. After removing a solvent therein, 50 g of a compound (A) was obtained by holding a precipitate in methanol (a yield: 65%).

The obtained compound (A) was element-analyzed, and the result is provided as follows.
  calcd. $C_{13}H_8BrNS$: C, 53.81; H, 2.78; N, 4.83; S, 11.05.
  found: C, 53.51; H, 2.82; N, 4.75; S, 11.10.

Second Step: Synthesis of Compound A-1

13.8 g (50 mmol) of the compound (A), 17 g (40 mmol) of 9-phenyl-9H,9'H-[3,3']bicarbazol-yl (B), and 7.6 g (55 mmol) of potassium carbonate were suspended in 250 ml of DMSO, 1 g (7 mmol) of 1,10-phenanthroline and 1 g (7 mmol) of copper chloride were added thereto, and the mixture was heated and refluxed under a nitrogen stream for 12 hours. The reaction solution was added to 1000 ml of MeOH, a solid crystallized therein was filtered and dissolved in monochlorobenzene and then, filtered with silica gel/Celite. After removing an organic solvent in an appropriate amount therefrom, a product was recrystallized in MeOH, obtaining 15 g of a compound A1 (a yield: 56%).

The obtained compound A-1 was element-analyzed, and the result is provided as follows.
  calcd. $C_{43}H_{27}N_3S$: C, 83.60; H, 4.41; N, 6.80; S, 5.19.
  found: C, 83.35; H, 4.30; N, 6.78; S, 5.08.

Example 2: Synthesis of Compound Represented by Chemical Formula A-4

A compound represented by the above formula A-4 as specific examples of a compound for an organic optoelectronic device according to the present invention was synthesized in a method according to the following reaction scheme 2.

[Reaction Scheme 2]

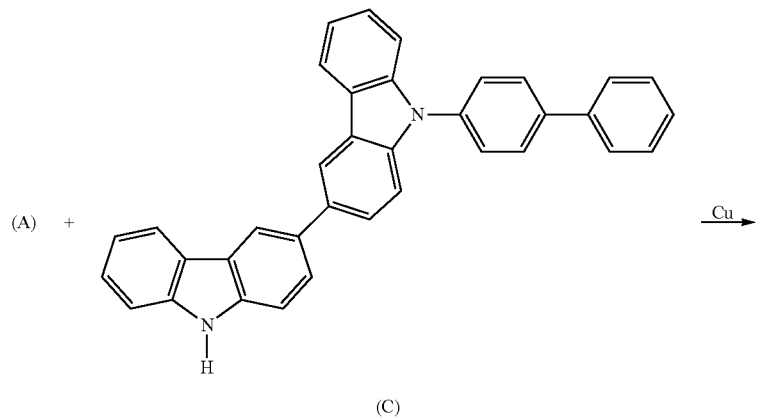

(A) +

(C)

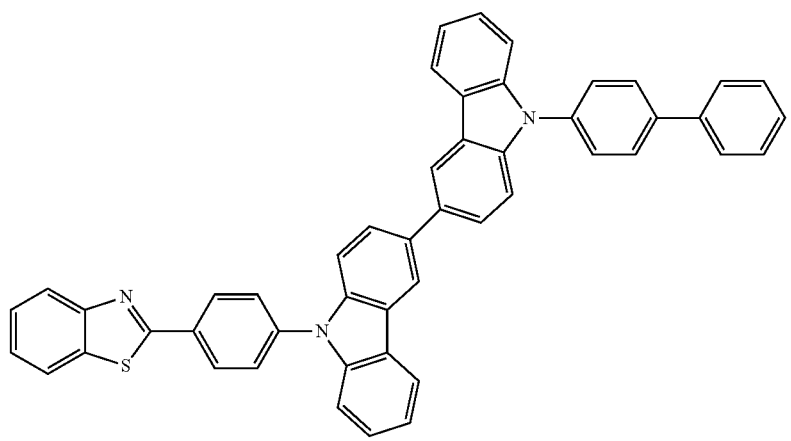

First Step: Synthesis of Compound A-4

10.3 g (40 mmol) of the compound (A), 15 g (40 mmol) of 9-phenyl-9H,9'H-[3,3']bicarbazol-yl (C), and 7.5 g (53 mmol) of potassium carbonate were suspended in 250 ml of DMSO, 1 g (7 mmol) of 1,10-phenanthroline and 1 g (7 mmol) of copper chloride were added thereto, and the mixture was heated and refluxed under a nitrogen stream for 12 hours. The reaction solution was added to 1000 ml of MeOH, a solid crystallized therein was filtered, dissolved in monochlorobenzene, and then, filtered through silica gel/Celite. After removing an organic solvent in an appropriate amount therefrom, a product was recrystallized in MeOH, obtaining 16.5 g of a compound A7 (a yield: 65%).

The obtained compound A-4 was element-analyzed, and the result is provided as follows.

calcd. C49H31N3S: C, 84.82; H, 4.50; N, 6.06; S, 4.62.

found: C, 84.79; H, 4.48; N, 6.01; S, 4.59.

Example 3: Synthesis of Compound Represented by Chemical Formula A-43

A compound represented by the above formula A-43 as specific examples of a compound for an organic optoelectronic device according to the present invention was synthesized in a method of the following reaction scheme 3.

[Reaction Scheme 3]

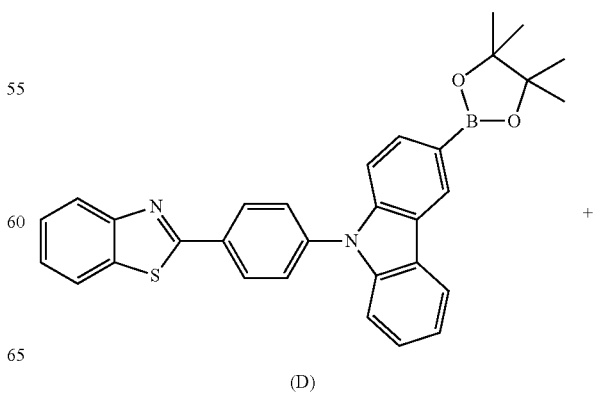

(D)

+

-continued

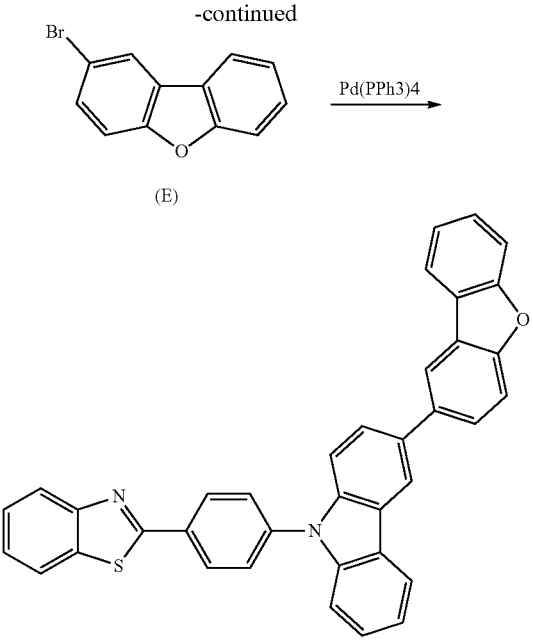

(E)

First Step: Synthesis of Compound A-43

12 g (23.8 mmol) of the compound (D), 6 g (24.8 mmol) of 2-bromo dibenzo furan, and 1.5 g (1 mmol) of tetrakis triphenyl phosphine were suspended in 250 ml of toluene/tetrahydrofuran, 250 ml of a 2M potassium carbonate aqueous solution was added thereto, and the mixture was heated and refluxed under a nitrogen stream for 24 hours. The reaction solution was added to 1000 ml of MeOH, a solid crystallized therein was filtered, dissolved in monochlorobenzene, and then, filtered through silica gel/Celite. After removing an organic solvent in an appropriate amount therefrom, a product therein was recrystallized in MeOH, obtaining 8 g of a compound A-43 (a yield: 62%).

The obtained compound A-43 was element-analyzed, and the result is provided as follows.

calcd. C37H22N2OS: C, 81.89; H, 4.09; N, 5.16; S, 5.91.
found: C, 81.89; H, 4.11; N, 5.15; S, 5.86.

Example 4: Synthesis of Compound Represented by Chemical Formula A-72

A compound represented by the above formula A-72 as specific examples of a compound for an organic optoelectronic device according to the present invention was synthesized in a method of the following reaction scheme 4.

[Reaction Scheme 4]

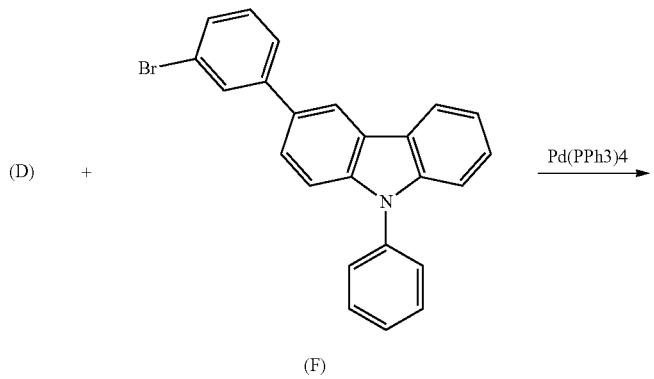

(F)

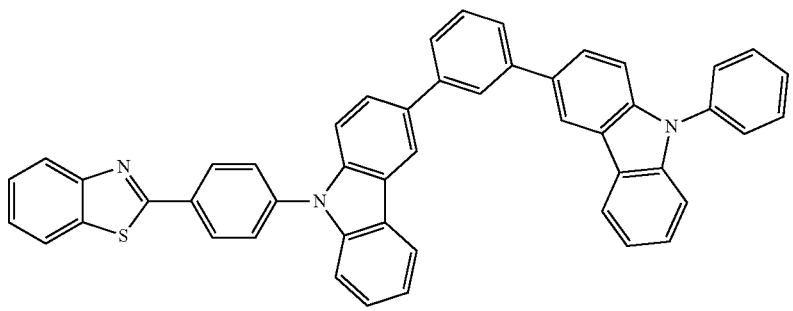

First Step: Synthesis of Compound A-72

12 g (23.8 mmol) of the compound (D), 9.4 g (23.8 mmol) of the compound (F), and 1.3 g (1 mmol) of tetrakis triphenyl phosphine were suspended in 250 ml of toluene/tetrahydrofuran, 250 ml of a 2M potassium carbonate aqueous solution was added thereto, and the mixture was heated and refluxed under a nitrogen stream for 24 hours. The reaction solution was added to 1000 ml of MeOH, and a solid crystallized therein was filtered, dissolved in monochlorobenzene, and then, filtered through silica gel/Celite. After removing an organic solvent in an appropriate amount therefrom, a product was recrystallized in MeOH, obtaining 10 g of a compound A-72 (a yield: 60%).

The obtained compound A-72 was element-analyzed, and the result is provided as follows.

calcd. C49H31N3S: C, 84.82; H, 4.50; N, 6.06; S, 4.62.
found: C, 84.80; H, 4.52; N, 6.15; S, 4.59.

Example 5: Synthesis of Compound Represented by Chemical Formula B-1

A compound of the above formula B-1 as specific examples of compound for an organic optoelectronic device according to the present invention was synthesized in a method of the following reaction scheme 5.

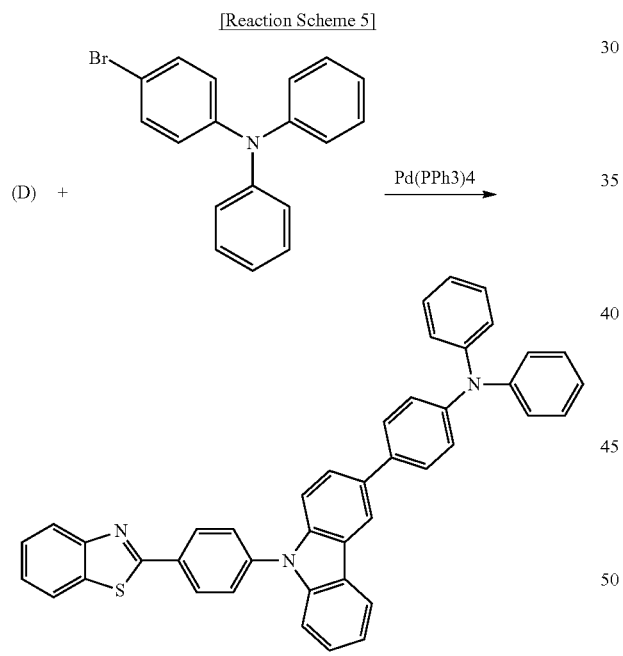

[Reaction Scheme 5]

First Step: Synthesis of Compound B-1

12 g (23.8 mmol) of the compound (D), 7.7 g (23.8 mmol) of a 4-bromo triphenyl amine compound, and 1.3 g (1 mmol) of tetrakis triphenyl phosphine were suspended in 250 ml of toluene/tetrahydrofuran, 250 ml of a 2M potassium carbonate aqueous solution was added thereto, and the mixture was heated and refluxed under a nitrogen stream for 24 hours. The reaction solution was added to 1000 ml of MeOH, and a solid crystallized therein was filtered, dissolved in monochlorobenzene, and then, filtered through silica gel/Celite. After removing an organic solvent in an appropriate amount therefrom, a product was recrystallized in MeOH, obtaining 8.8 g of a compound B-1 (a yield: 60%).

The obtained compound B-1 was element-analyzed, and the result is provided as follows.

calcd. C43H29N3S: C, 83.33; H, 4.72; N, 6.78; S, 5.17.
found: C, 83.37; H, 4.69; N, 6.71; S, 5.12.

Example 6: Synthesis of Compound Represented by Chemical Formula D-1

A compound of the above formula D-1 was synthesized as specific examples of a compound for an organic optoelectronic device according to the present invention in a method of the following reaction scheme 6.

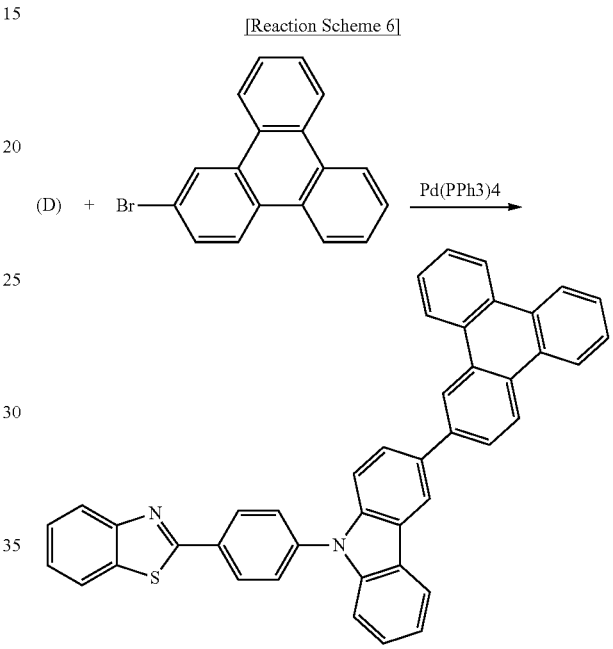

[Reaction Scheme 6]

First Step: Synthesis of Compound D-1

12 g (23.8 mmol) of the compound (D), 7.3 g (23.8 mmol) of a 2-bromo triphenylene compound, and 1.3 g (1 mmol) of tetrakis triphenyl phosphine were suspended in 250 ml of toluene/tetrahydrofuran, 250 ml of a 2M potassium carbonate aqueous solution was added thereto, and the mixture was heated and refluxed under a nitrogen stream for 24 hours. The reaction solution was added to 1000 ml of MeOH, and a solid crystallized thereon was filtered, dissolved in monochlorobenzene, and then, filtered through silica gel/Celite. After removing an organic solvent in an appropriate amount therefrom, a product was recrystallized in MeOH, obtaining 8.5 g of a compound D-1 (a yield: 60%).

The obtained compound D-1 was element-analyzed, and the result is provided as follows.

calcd. C43H26N2S: C, 85.68; H, 4.35; N, 4.65; S, 5.32.
found: C, 85.67; H, 4.35; N, 4.65; S, 5.30.

Comparative Example 1: Synthesis of Compound Represented by Chemical Formula R1

A compound represented by the above formula R-1 as specific Comparative Examples of a compound for an organic optoelectronic device according to the present invention was synthesized in a method of the following reaction scheme 7.

[Reaction Scheme 7]

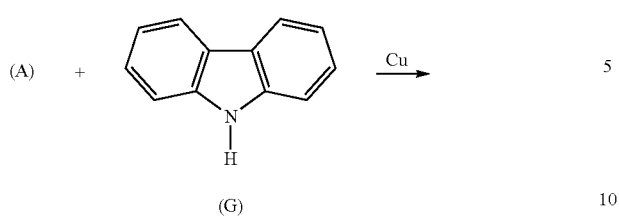

(G)

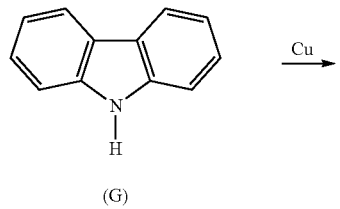

(G)

-continued

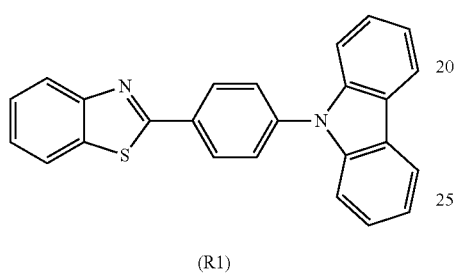

(R1)

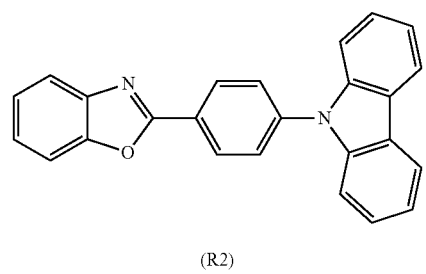

(R2)

First Step: Synthesis of Compound R-1

31.2 g (110 mmol) of the compound (A), 15 g (90 mmol) of N—H-carbazole (G), and 7.5 g (53 mmol) of potassium carbonate were suspended in 250 ml of DMSO, 1 g (7 mmol) of 1,10-phenanthroline and 1 g (7 mmol) of copper chloride were added thereto, and the mixture was heated and refluxed under a nitrogen stream for 24 hours. The reaction solution was added to 1000 ml of MeOH, and a solid crystallized therein was filtered, dissolved in monochlorobenzene, and then, filtered through silica gel/Celite. After removing an organic solvent in an appropriate amount therefrom, a product was recrystallized in MeOH, obtaining 20 g of a compound R-1 (a yield: 60%).

The obtained compound R-1 was element-analyzed, and the result is provided as follows.

calcd. C25H16N2S: C, 79.76; H, 4.28; N, 7.44; S, 8.52.

found: C, 79.69; H, 4.28; N, 7.39; S, 8.55.

Comparative Example 2: Synthesis of Compound Represented by Chemical Formula R-2

A compound represented by the above formula R-2 as specific Comparative Examples of a compound for an organic optoelectronic device according to the present invention was synthesized in a method of the following reaction scheme 8.

[Reaction Scheme 8]

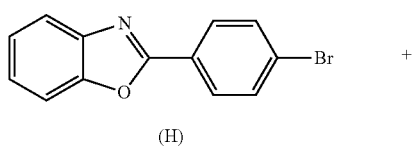

(H)

First Step: Synthesis of Compound R-2

31.2 g (110 mmol) of the compound (A), 15 g (90 mmol) of N—H-carbazole (G), and 7.5 g (53 mmol) of potassium carbonate were suspended in 250 ml of DMSO, 1 g (7 mmol) of 1,10-phenanthroline and 1 g (7 mmol) of copper chloride were added thereto, and the mixture was heated and refluxed under a nitrogen stream for 24 hours. The reaction solution was added to 1000 ml of MeOH, and a solid crystallized therein was filtered, dissolved in monochlorobenzene, and then, filtered through silica gel/Celite. After removing an organic solvent in an appropriate amount therefrom, a product was recrystallized in MeOH, obtaining 23 g of a compound R-2 (a yield: 63%).

The obtained compound R-2 was element-analyzed, and the result is provided as follows.

calcd. C25H16N2O: C, 83.31; H, 4.47; N, 7.77.

found: C, 83.33; H, 4.48; N, 7.73.

Manufacture of Organic Light Emitting Diode

Example 7

Specifically illustrating a method of manufacturing an organic light-emitting device, a anode is manufactured by cutting an ITO glass substrate having sheet resistance of 15 $\Omega/cm^2$ into a size of 50 mm×50 mm×0.7 mm, respectively washing the cut substrate with an ultrasonic wave in acetone, isopropylalcohol, and pure water for 15 minutes, and then, cleaning it with an UV ozone for 30 minutes.

Subsequently, the following HTM compound was vacuum-deposited to form a 1200 Å-thick hole injection layer on this ITO transparent electrode as a anode.

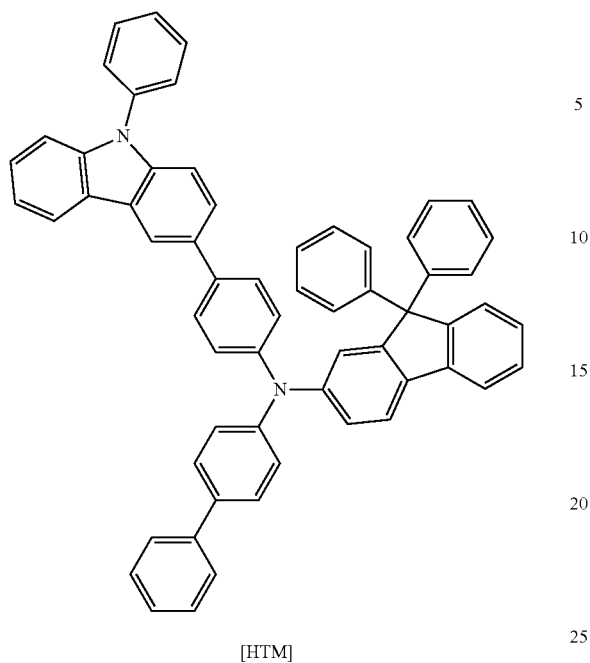

[HTM]

The compound synthesized according to Example 1 was used as a host and doped with 7 wt % of the following PhGD compound as a green phosphorescence dopant and then, vacuum-deposited to form a 300 Å-thick emission layer. Herein, a 1000 Å-thick ITO was used as for the anode, and a 1000 Å-thick aluminum (Al) was used as for a negative electrode.

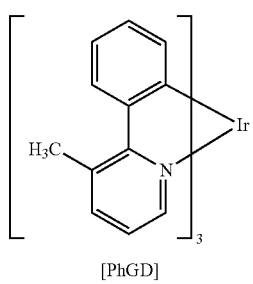

[PhGD]

Subsequently, BAlq [Bis(2-methyl-8-quinolinolato-N1, O8)-(1,1'-Biphenyl-4-olato)aluminum] was laminated to be 50 Å-thick, and Alq3 [Tris(8-hydroxyquinolinato)aluminum] was sequentially laminated to be 250 Å thick to form an electron transport layer on the emission layer. On the electron-transport layer, LiF and Al were sequentially vacuum-deposition to respectively be 5 Å thick and 1000 Å thick to form a cathode, manufacturing an organic light-emitting device.

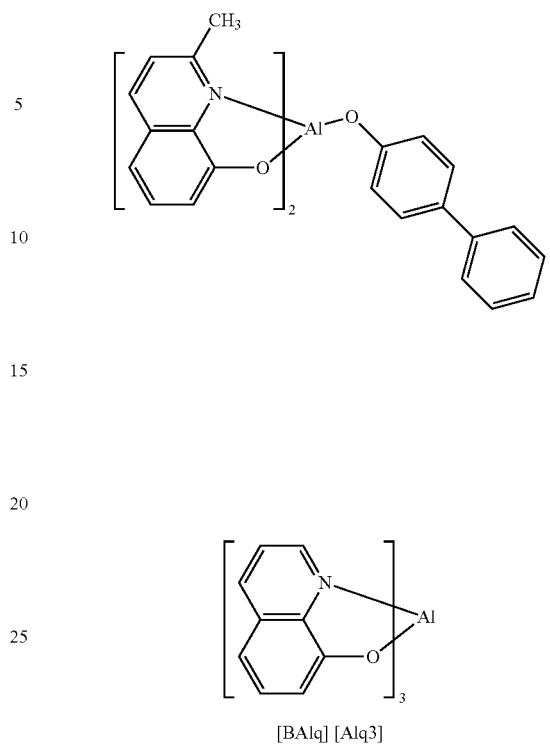

[BAlq] [Alq3]

Example 8

An organic light-emitting device was manufactured according to the same method as Example 7 except for using the compound according to Example 2 instead of the compound according to Example 1 in Example 7.

Example 9

An organic light-emitting device was manufactured according to the same method as Example 7 except for using the compound according to Example 4 instead of the compound according to Example 1 in Example 7.

Example 10

Specifically, an organic light-emitting device was manufactured by cutting an ITO glass substrate having sheet resistance of 15 Ω/cm$^2$ into a size of 50 mm×50 mm×0.7 mm, washing the cut substrate with an ultrasonic wave in acetone, isopropylalcohol, and pure water for 15 minutes respectively and then, cleaning it with an UV ozone for 30 minutes.

This ITO transparent electrode was used as a anode, and a hole injection layer was formed to be 1200 Å thick thereon by vacuum-depositing the following HTM compound and the compound according to Example 1 on the ITO substrate.

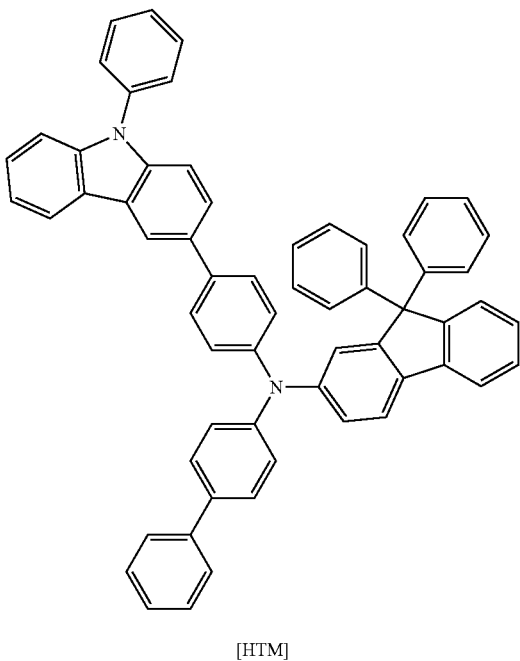

[HTM]

On the hole injection layer, a 300 Å-thick emission layer was formed by using 4,4-N,N-dicarbazolebiphenyl (CBP) as a host and doping it with 7 wt % of the following PhGD compound as a green phosphorescence dopant. Herein, a 1000 Å-thick ITO was used as for an anode, and a 1000 Å-thick aluminum (Al) was used as for a negative electrode.

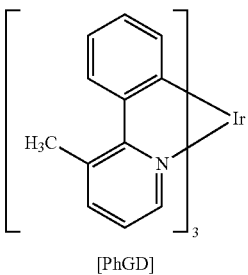

[PhGD]

Subsequently, 50 Å-thick BAlq [bis(2-methyl-8-quinolinolato-N1,O8)-(1,1'-biphenyl-4-olato)aluminum] and 250 Å-thick Alq3 [tris(8-hydroxyquinolinato)aluminium] were sequentially laminated to form an electron-transport layer on the emission layer. On the electron transport layer, 5 Å-thick LiF and 1000 Å-thick Al were sequentially vacuum-deposited to form a cathode, manufacturing an organic light-emitting device.

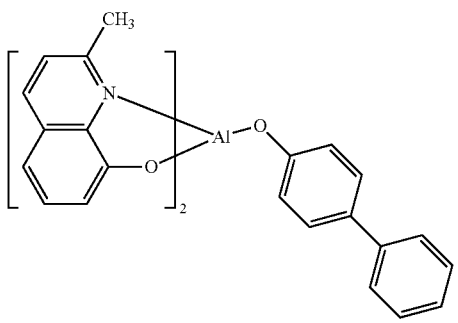

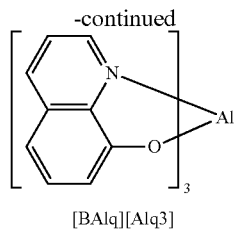

[BAlq][Alq3]

Example 11

An organic light-emitting device was manufactured according to the same method as Example 10 except for using the compound of Example 2 instead of the compound of Example 1 in Example 10.

Example 12

An organic light-emitting device was manufactured according to the same method as Example 10 except for using the compound of Example 4 instead of the compound of Example 1 in Example 10.

Comparative Example 3

An organic light-emitting device was manufactured according to the same method as Example 7 except for using 4,4-N,N-dicarbazolebiphenyl (CBP) instead of the compound synthesized according to Example 1 as a host for an emission layer in Example 1.

Comparative Example 4

An organic light-emitting device was manufactured according to the same method as Example 7 except for using the compound R1 synthesized according to Comparative Example 1 as a host for an emission layer instead of 4,4-N,N-dicarbazolebiphenyl (CBP) in Comparative Example 3.

Comparative Example 5

An organic light-emitting device was manufactured according to the same method as Example 7 except for using the compound $R^2$ synthesized according to Comparative Example 2 as a host for an emission layer instead of 4,4-N,N-dicarbazolebiphenyl (CBP) in Comparative Example 3.

Performance Measurement of Organic Light Emitting Diode

Current density change, luminance change, and luminous efficiency of each organic light emitting diode according to Examples 8 to 12 and Comparative Examples 3 to 5 depending on a voltage were measured. Specific measurement methods are as follows, and the results are shown in the following Tables 1 and 2.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), and the measured current value was divided by area to provide the result.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

The luminance, current density, and voltage obtained from the (1) and (2) were used to calculate current efficiency (cd/A) and power efficiency (lm/W).

TABLE 1

|  | Driving voltage (Vd, V) | Current efficiency (cd/A) | Power efficiency (lm/W) | Luminance (cd/m$^2$) | Color coordinate (CIEx) | Color coordinate (CIEy) |
| --- | --- | --- | --- | --- | --- | --- |
| Comparative Example 3 | 3.37 | 37.2 | 36 | 3000 | 0.341 | 0.625 |
| Comparative Example 4 | 3.30 | 40.2 | 39.1 | 3000 | 0.350 | 0.620 |
| Comparative Example 5 | 3.28 | 38.2 | 34.4 | 3000 | 0.341 | 0.645 |
| Example 8 | 3.28 | 41.8 | 40.5 | 3000 | 0.350 | 0.620 |
| Example 9 | 3.46 | 48.9 | 46.1 | 3000 | 0.350 | 0.619 |

The devices according to Examples 8 and 9 showed excellent characteristics compared with the devices according to Comparative Examples 3 to 5.

In addition, current density change, luminance change, and emission efficiency of the organic light-emitting devices respectively including an interlayer according to Examples 10 to 12 depending on voltage change were measured, and the results are provided in the following Table 2.

TABLE 2

|  | Driving voltage (Vd, V) | Current efficiency (cd/A) | Power efficiency (lm/W) | Luminance (cd/m$^2$) | Color coordinate (CIEx) | Color coordinate (CIEy) |
| --- | --- | --- | --- | --- | --- | --- |
| Comparative Example 3 | 3.37 | 37.2 | 36 | 3000 | 0.341 | 0.625 |
| Example 10 | 4.31 | 51.1 | 37.2 | 3000 | 0.323 | 0.674 |
| Example 11 | 4.14 | 52.5 | 39.8 | 3000 | 0.322 | 0.654 |
| Example 12 | 4.13 | 49.8 | 37.8 | 3000 | 0.319 | 0.649 |

The devices including an interlayer according to Examples 10 to 12 showed improved efficiency compared with a device manufactured by applying CBP as a single host for an emission layer according to Comparative Example 3.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound for an organic optoelectronic device represented by the following Chemical Formula 1:

[Chemical Formula 1]

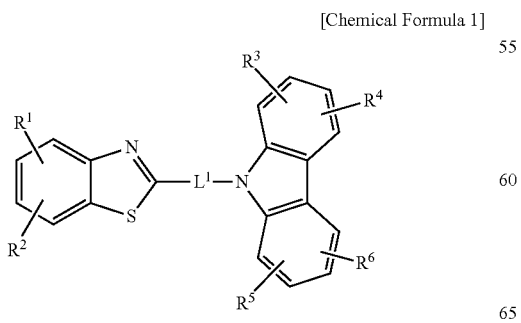

wherein, in the above Chemical Formula 1, $L^1$ is a substituted or unsubstituted C6 to C30 arylene group or a substituted or unsubstituted C2 to C30 heteroarylene group, $R^1$ and $R^2$ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, $R^3$ to $R^6$ are independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof, at least one of $R^3$ to $R^6$ is a substituted or unsubstituted carbazolyl group, a substituted or unsubstituted dibenzofuranyl group, a substituted or unsubstituted dibenzothiophenyl group, a substituted or unsubstituted fluorenyl group, a substituted or unsubstituted amine group, or a substituted or unsubstituted triphenylenyl group or $R^3$ and $R^4$ are fused to each other to provide a ring, and when $R^3$ and $R^4$ are fused to each other to provide a ring, the compound represented by Chemical Formula 1 is represented by the following Chemical Formula 3,

[Chemical Formula 3]

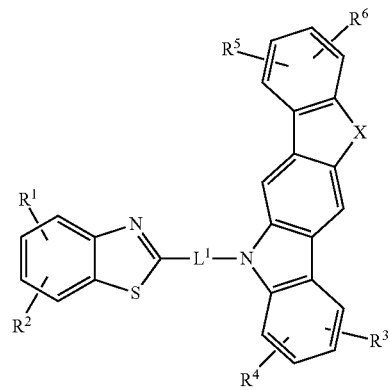

wherein, in the above Chemical Formula 3,

L¹ is a substituted or unsubstituted C6 to C30 arylene group or a substituted or unsubstituted C2 to C30 heteroarylene group, R¹ to R⁶ are each independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, X is —NR⁷—, wherein R⁷ is hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof.

2. The compound for an organic optoelectronic device of claim 1, wherein the compound for an organic optoelectronic device represented by the above Chemical Formula 1 is represented by the following Chemical Formula 2:

[Chemical Formula 2]

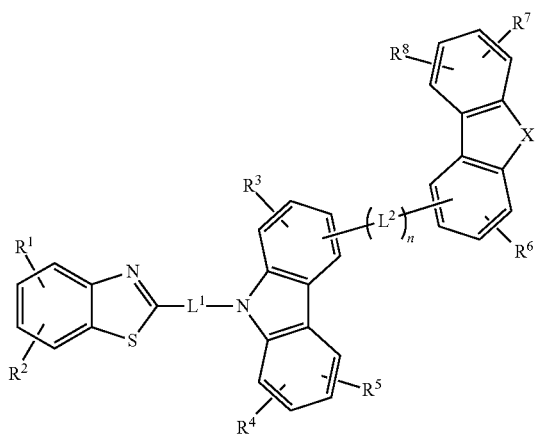

wherein, in the above Chemical Formula 2,

L¹ and L² are independently a substituted or unsubstituted C6 to C30 arylene group or a substituted or unsubstituted C2 to C30 heteroarylene group, n is an integer ranging from 0 to 3, R¹ to R⁸ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, X is —NR⁹—, —O—, —S— or —CR¹⁰R¹¹—, wherein the R⁹ to R¹¹ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, or the R¹⁰ and R¹¹ are fused to each other to provide a ring.

3. The compound for an organic optoelectronic device of claim 1, wherein the compound for an organic optoelectronic device represented by the above Chemical Formula 1 is represented by the following Chemical Formula 4:

[Chemical Formula 4]

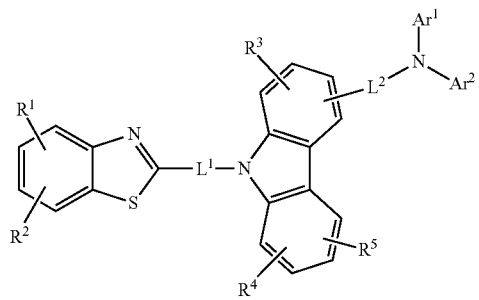

wherein, in the above Chemical Formula 4,

L¹ and L² are independently a substituted or unsubstituted C6 to C30 arylene group or a substituted or unsubstituted C2 to C30 heteroarylene group, R¹ to R⁵ are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, and Ar¹ and Ar² are independently a substituted or unsubstituted C1 to C10 alkyl group, a substituted or unsubstituted C6 to C30 aryl group, a substituted or unsubstituted C2 to C30 heteroaryl group, or a combination thereof.

4. The compound for an organic optoelectronic device of claim 1, wherein the compound for an organic optoelectronic device represented by the above Chemical Formula 1 is represented by the following Chemical Formula 5:

[Chemical Formula 5]

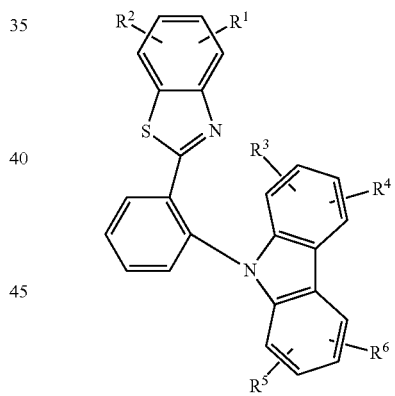

wherein, in the above Chemical Formula 5,

R¹ and R² are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, R³ to R⁶ are independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof, at least one of R³ to R⁶ is a substituted or unsubstituted carbazolyl group, a substituted or unsubstituted dibenzofuranyl group, a substituted or unsubstituted dibenzothiophenyl group, a substituted or unsubstituted fluorenyl group, a substituted or unsubstituted amine group, or a substituted or unsubstituted triphenylenyl group or R³ and R⁴ are fused to each other to provide a ring, and when R³ and R⁴ are fused to each other to provide a ring, the compound represented by Chemical Formula 1 is represented by the following Chemical Formula 3,

[Chemical Formula 3]

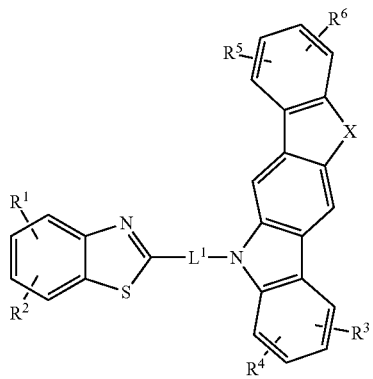

wherein, in the above Chemical Formula 3,
L¹ is a substituted or unsubstituted C6 to C30 arylene group or a substituted or unsubstituted C2 to C30 heteroarylene group,
R¹ to R⁶ are each independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof,
X is —NR⁷—, wherein R⁷ is hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof.

5. The compound for an organic optoelectronic device of claim 1, wherein the compound for an organic optoelectronic device represented by the above Chemical Formula 1 is represented by the following Chemical Formula 6:

[Chemical Formula 6]

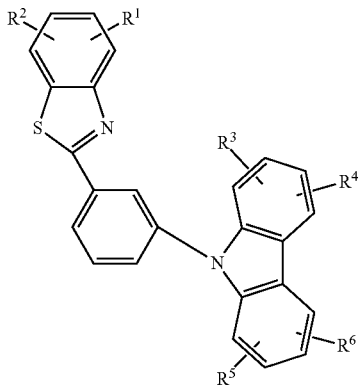

wherein, in the above Chemical Formula 6,
R¹ and R² are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof,
R³ to R⁶ are independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof,
at least one of R³ to R⁶ is a substituted or unsubstituted carbazolyl group, a substituted or unsubstituted dibenzofuranyl group, a substituted or unsubstituted dibenzothiophenyl group, a substituted or unsubstituted fluorenyl group, a substituted or unsubstituted amine group, or a substituted or unsubstituted triphenylenyl group or R³ and R⁴ are fused to each other to provide a ring, and when R³ and R⁴ are fused to each other to provide a ring, the compound represented by Chemical Formula 1 is represented by the following Chemical Formula 3,

[Chemical Formula 3]

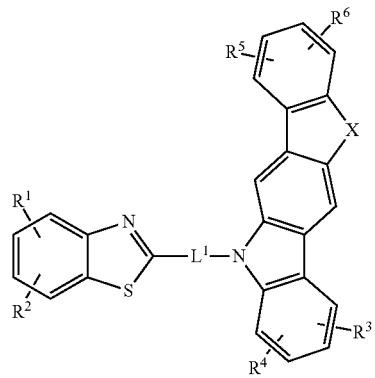

wherein, in the above Chemical Formula 3,
L¹ is a substituted or unsubstituted C6 to C30 arylene group or a substituted or unsubstituted C2 to C30 heteroarylene group,
R¹ to R⁶ are each independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof,
X is —NR⁷—, wherein R⁷ is hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof.

6. The compound for an organic optoelectronic device of claim 1, wherein the compound for an organic optoelectronic device represented by the above Chemical Formula 1 is represented by the following Chemical Formula 7:

[Chemical Formula 7]

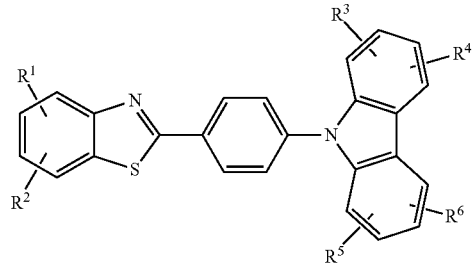

wherein, in the above Chemical Formula 7,
R¹ and R² are independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof,
R³ to R⁶ are independently hydrogen, deuterium, a substituted or unsubstituted amine group, a substituted or unsubstituted C1 to C10 alkyl group, a substituted or unsubstituted C6 to C30 aryl group, a substituted or unsubstituted C2 to C30 heteroaryl group, or a combination thereof, at least one of R³ to R⁶ is a substituted or unsubstituted carbazolyl group, a substituted or unsubstituted dibenzofuranyl group, a substituted or unsubstituted dibenzothiophenyl group, a substituted or unsubstituted fluorenyl group, a substituted or unsubstituted amine group, or a substituted or unsubstituted triphenylenyl group or R³ and R⁴ are fused to each other to provide a ring, and when R³ and R⁴ are fused to each other to provide a ring, the compound represented by Chemical Formula 1 is represented by the following Chemical Formula 3,

[Chemical Formula 3]

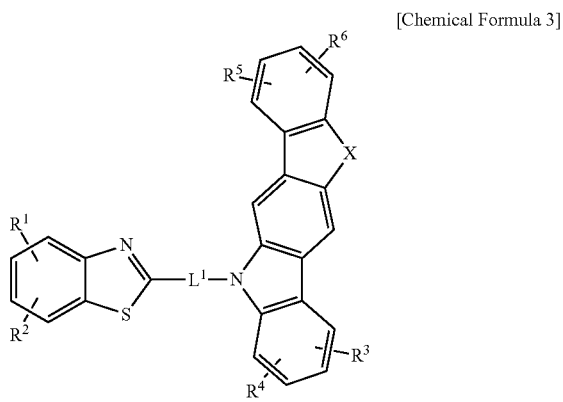

wherein, in the above Chemical Formula 3, $L^1$ is a substituted or unsubstituted C6 to C30 arylene group or a substituted or unsubstituted C2 to C30 heteroarylene group, $R^1$ to $R^6$ are each independently hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof, X is —NR⁷—, wherein $R^7$ is hydrogen, deuterium, a substituted or unsubstituted C1 to C10 alkyl group, a substituted or unsubstituted C6 to C30 aryl group, a substituted or unsubstituted C2 to C30 heteroaryl group, or a combination thereof.

7. The compound for an organic optoelectronic device of claim 1, wherein the $L^1$ is a substituted or unsubstituted phenylene group or a substituted or unsubstituted naphthylene group.

8. The compound for an organic optoelectronic device of claim 1, wherein the compound for an organic optoelectronic device is one of compounds represented by the following Chemical Formulae A-1 to A-74:

[Chemical Formula A-1]

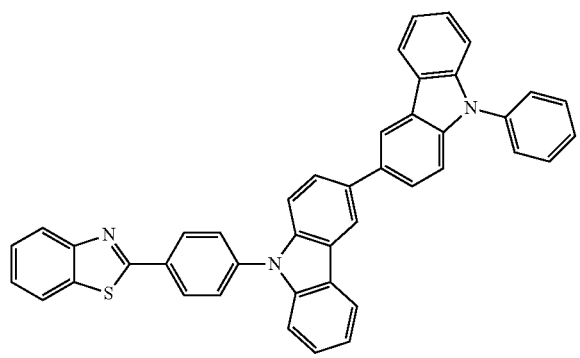

[Chemical Formula A-2]

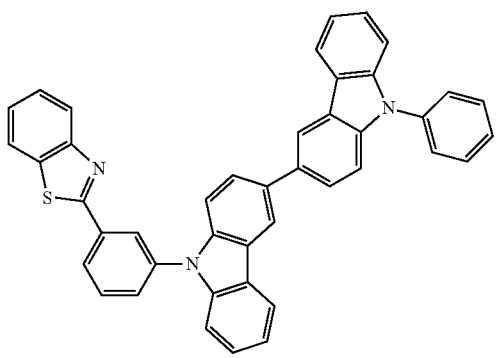

[Chemical Formula A-3]

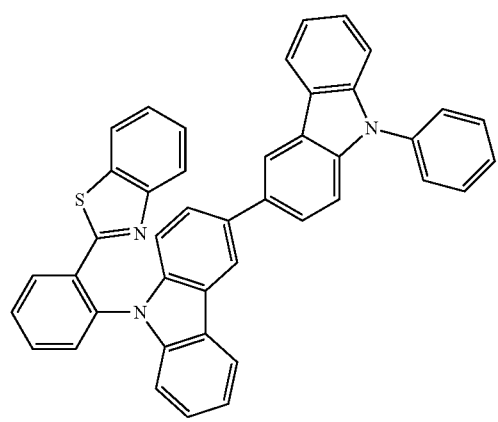

[Chemical Formula A-4]
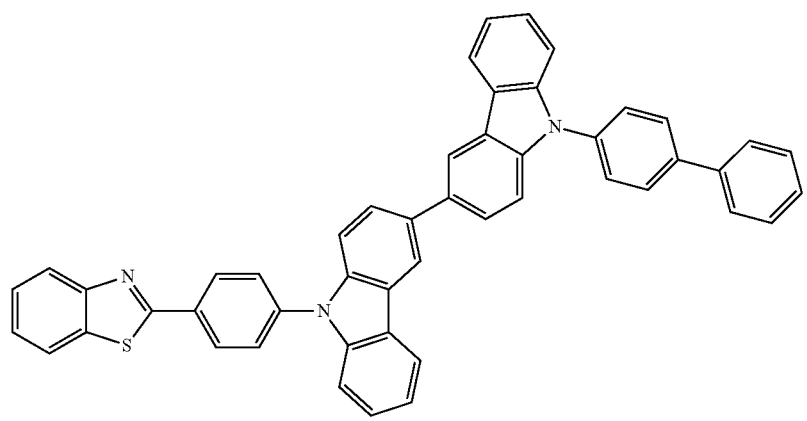
[Chemical Formula A-5]
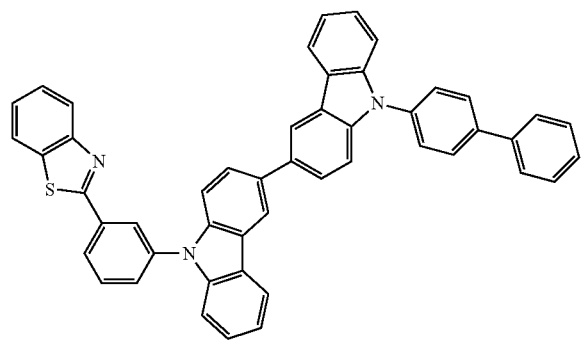
[Chemical Formula A-6]
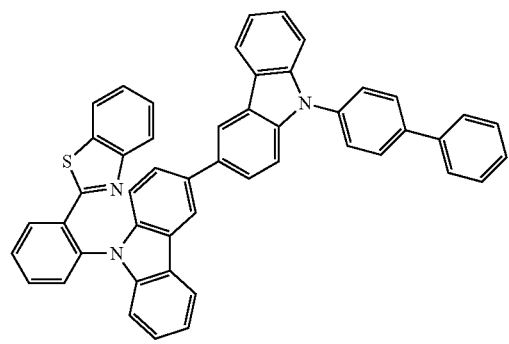
[Chemical Formula A-7]
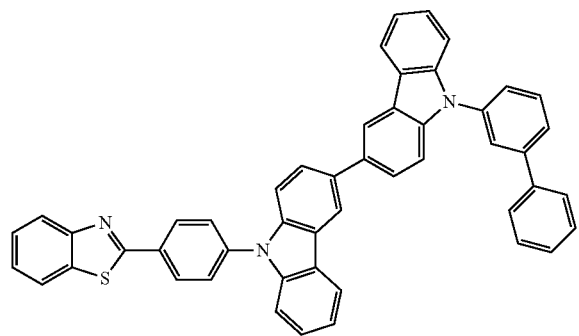
[Chemical Formula A-8]
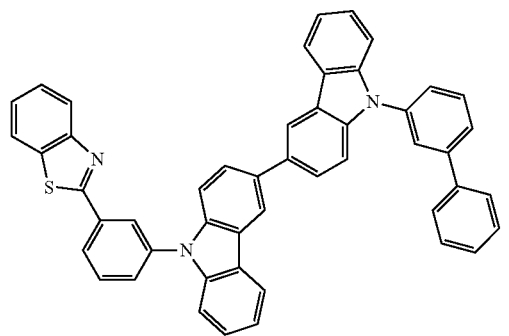
[Chemical Formula A-9]
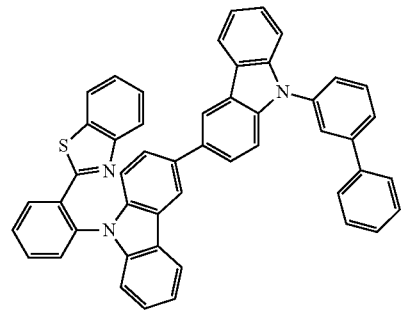
[Chemical Formula A-10]
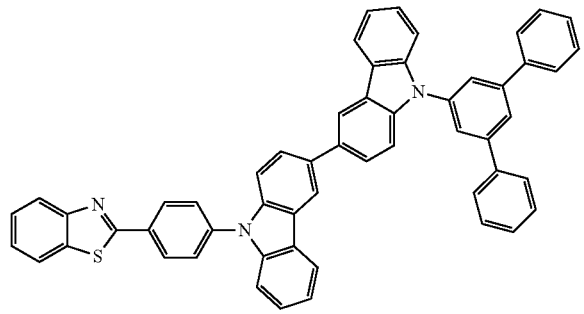

-continued
[Chemical Formula A-11]
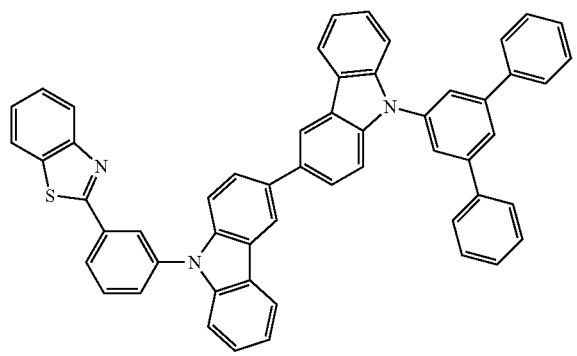
[Chemical Formula A-12]
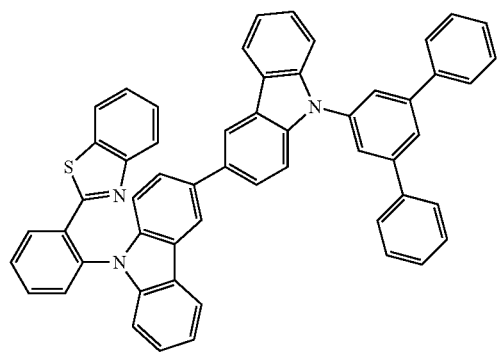
[Chemical Formula A-13]
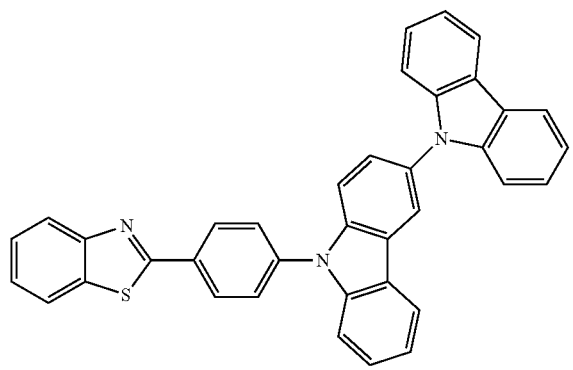
[Chemical Formula A-14]
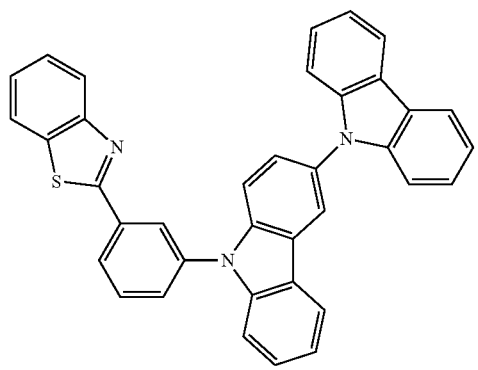
[Chemical Formula A-15]
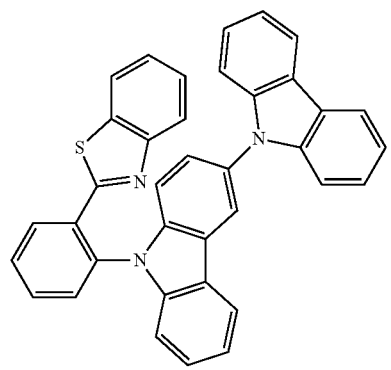
[Chemical Formula A-16]
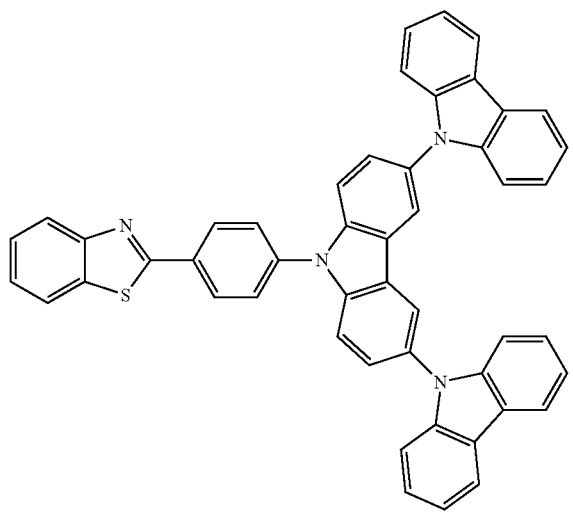

-continued
[Chemical Formula A-17]
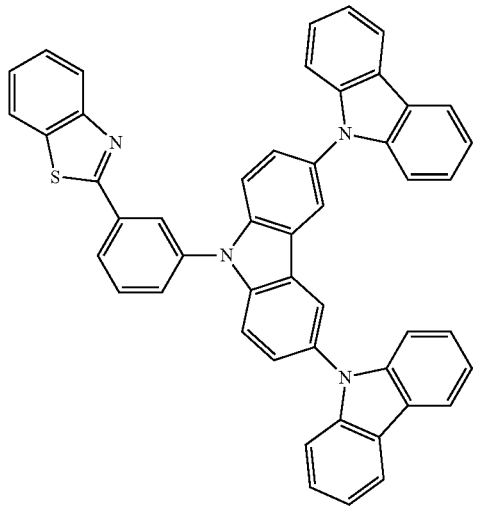
[Chemical Formula A-18]
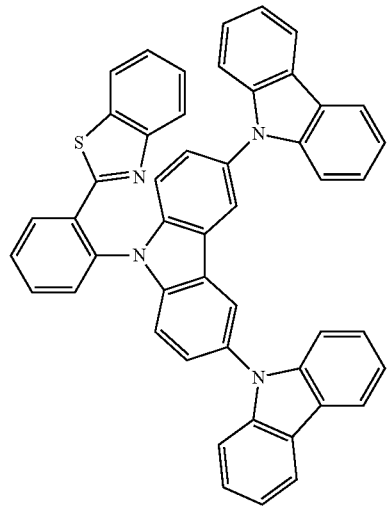
[Chemical Formula A-19]
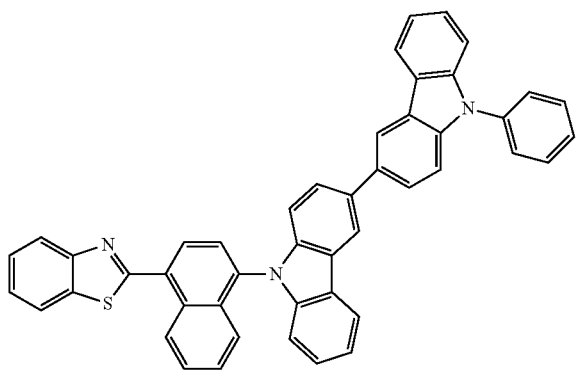
[Chemical Formula A-20]
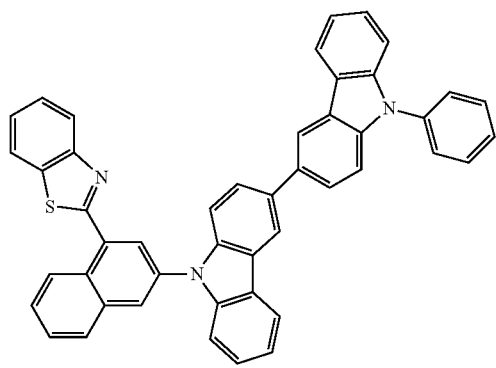
[Chemical Formula A-21]
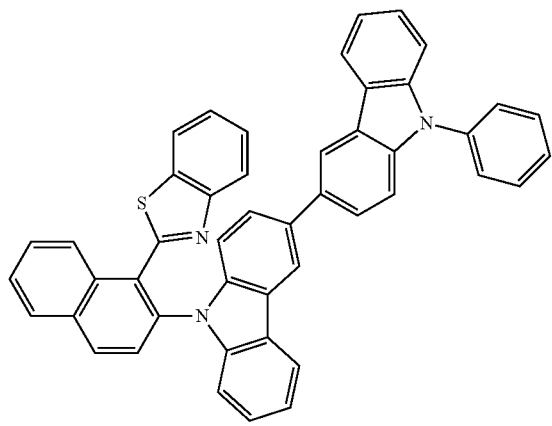

[Chemical Formula A-22]
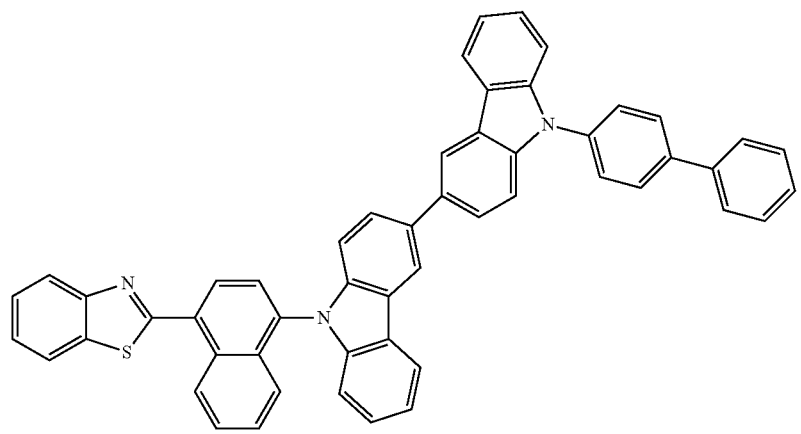
[Chemical Formula A-23]
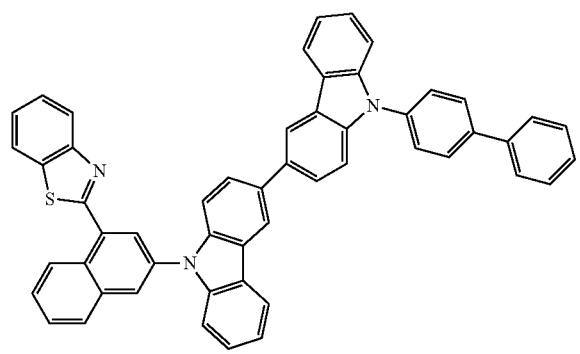
[Chemical Formula A-24]
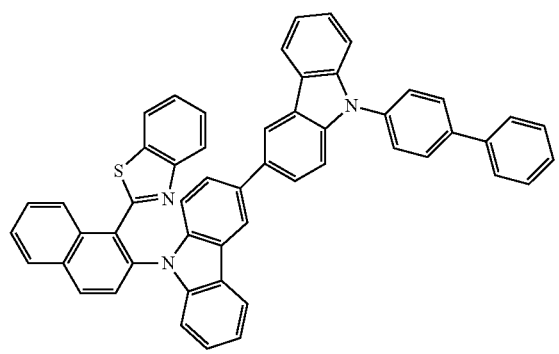
[Chemical Formula A-25]
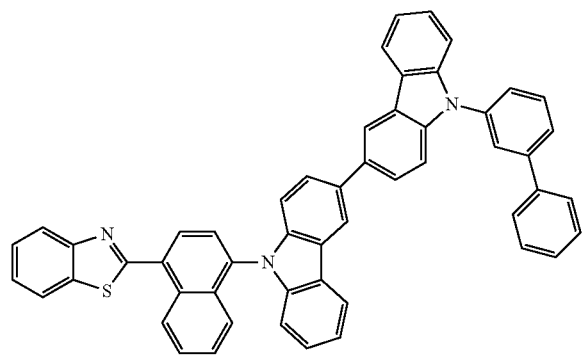
[Chemical Formula A-26]
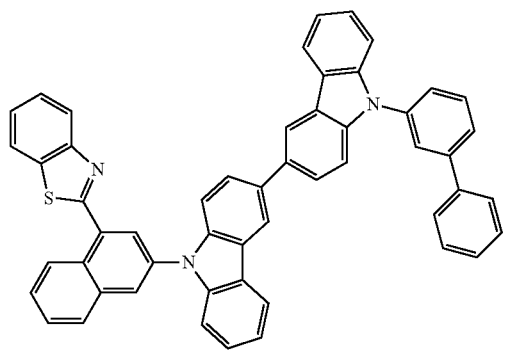
[Chemical Formula A-27]
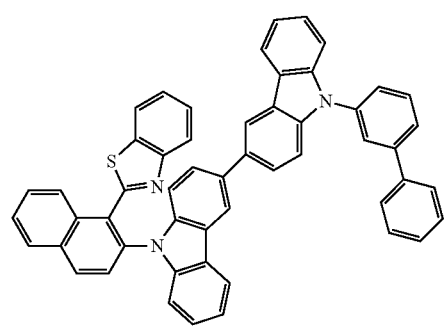
[Chemical Formula A-28]
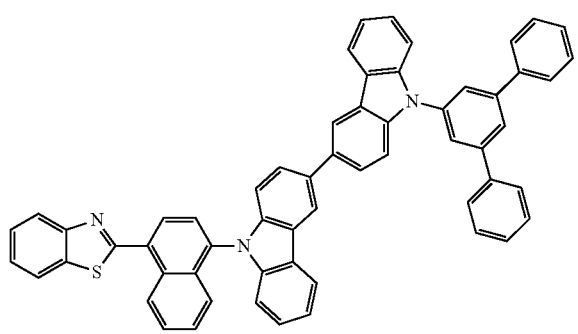

[Chemical Formula A-29]
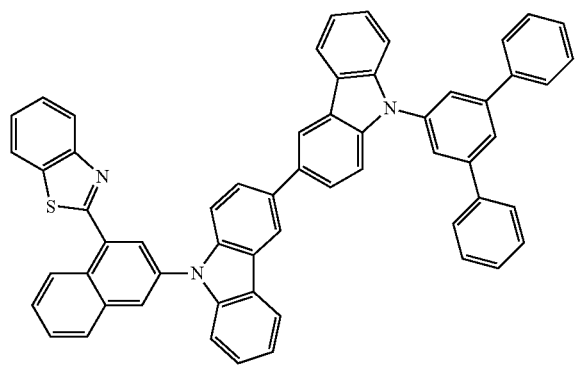
[Chemical Formula A-30]
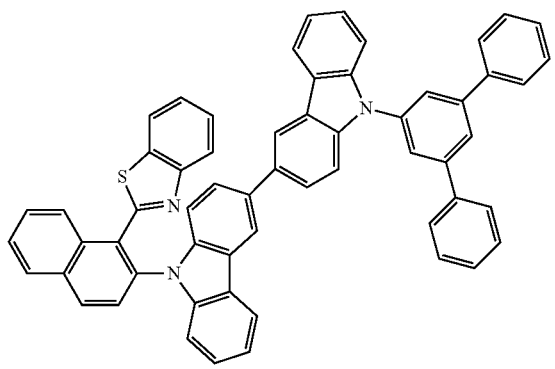
[Chemical Formula A-31]
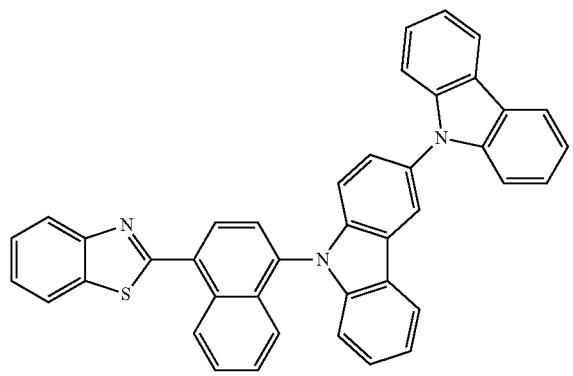
[Chemical Formula A-32]
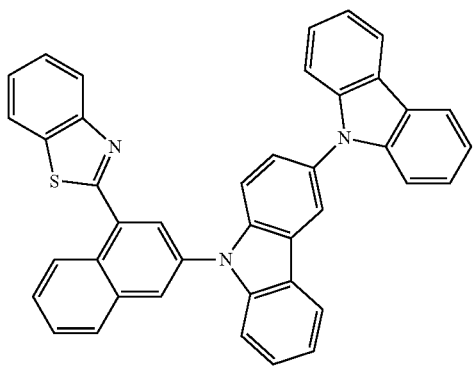
[Chemical Formula A-33]
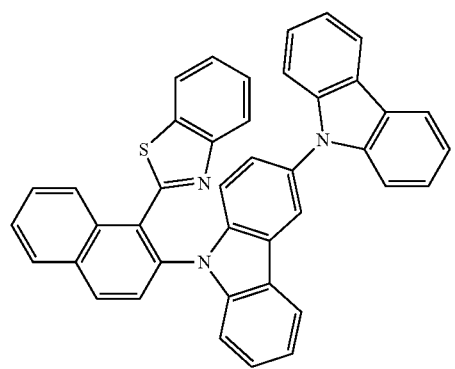
[Chemical Formula A-34]
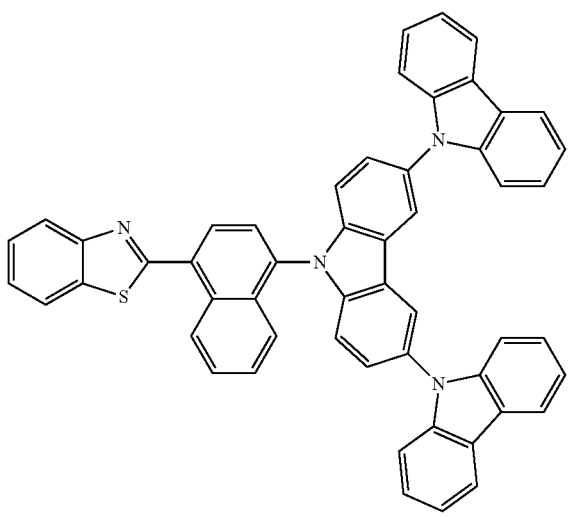

[Chemical Formula A-35]
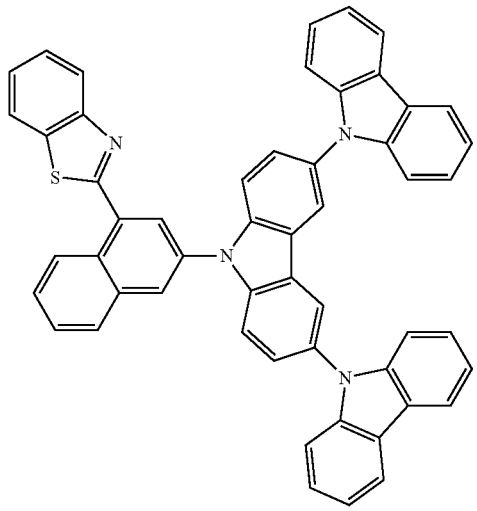
[Chemical Formula A-36]
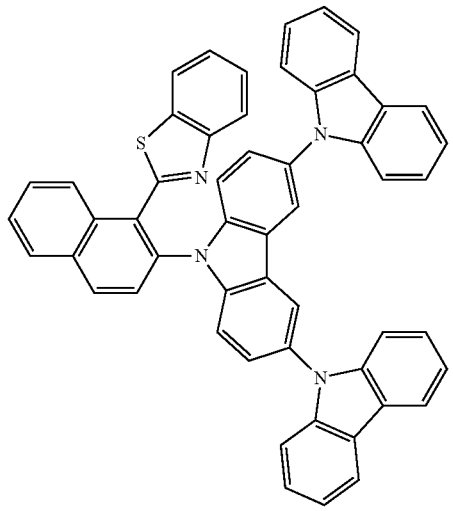
[Chemical Formula A-37]
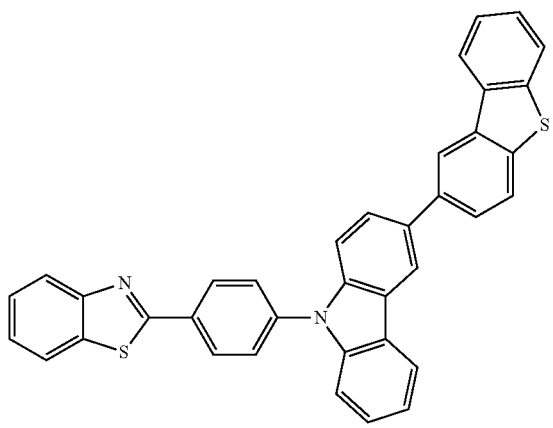
[Chemical Formula A-38]
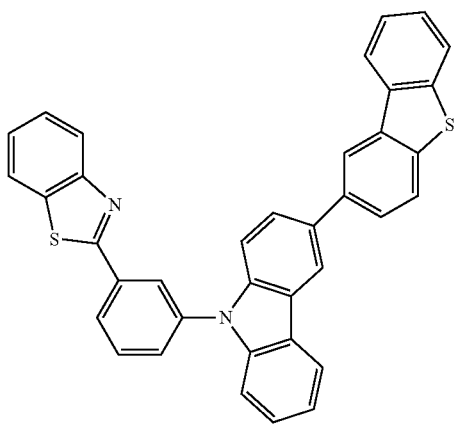
[Chemical Formula A-39]
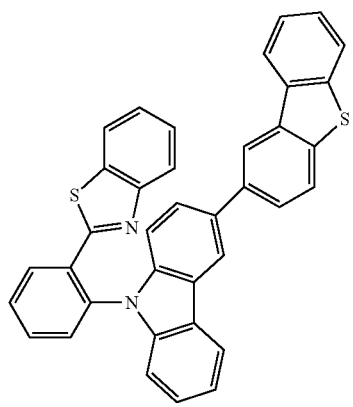
[Chemical Formula A-40]
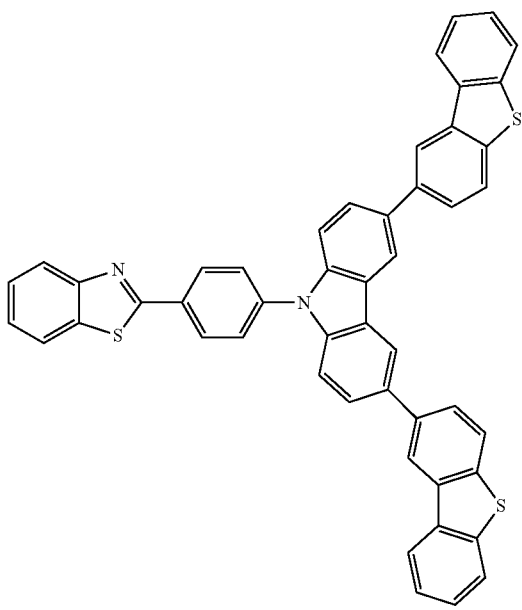

-continued
[Chemical Formula A-41]
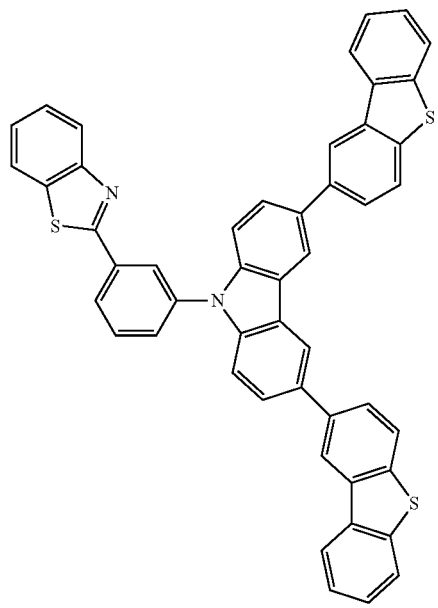
[Chemical Formula A-42]
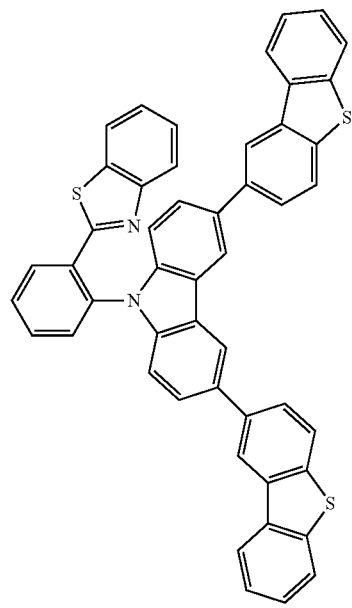
[Chemical Formula A-43]
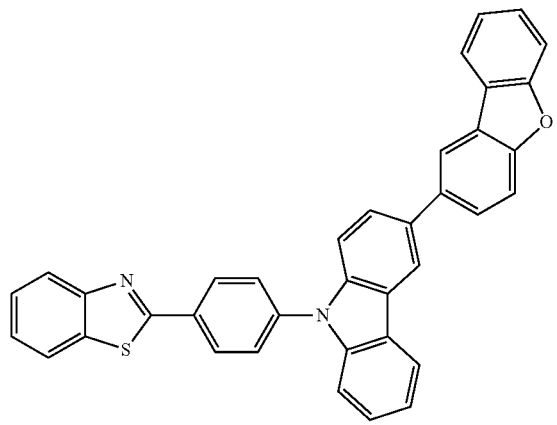
[Chemical Formula A-44]
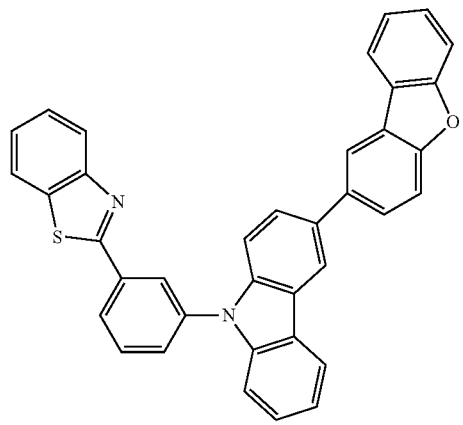

-continued
[Chemical Formula A-45]
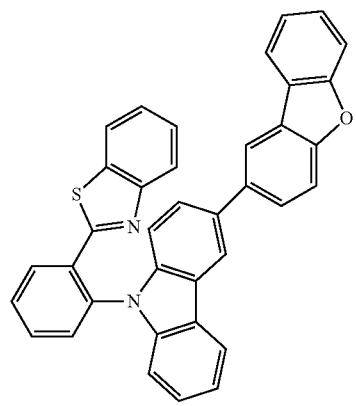
[Chemical Formula A-46]
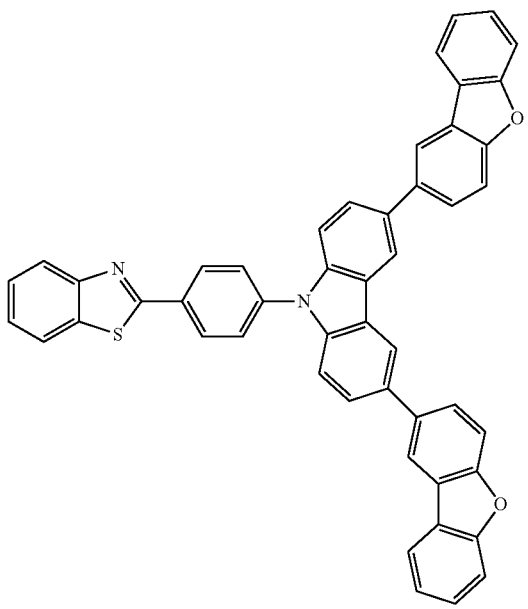
[Chemical Formula A-47]
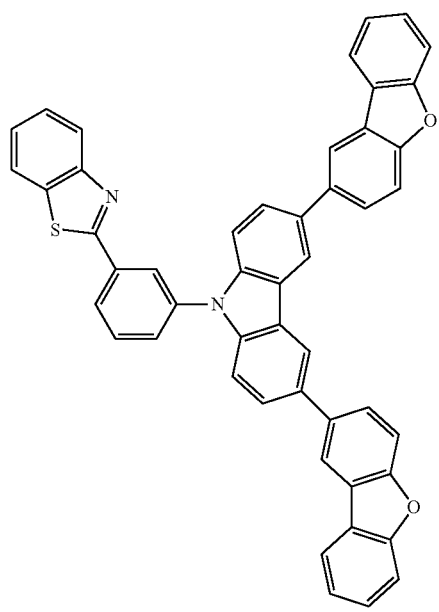
[Chemical Formula A-48]
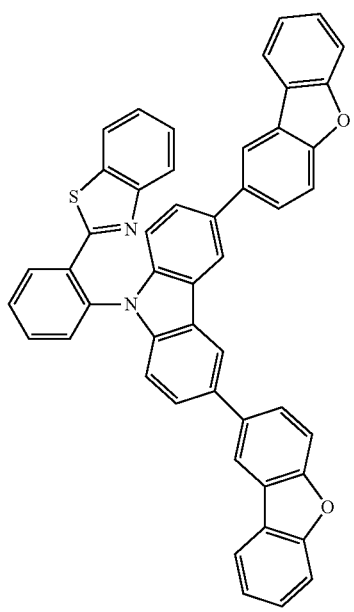

[Chemical Formula A-49]
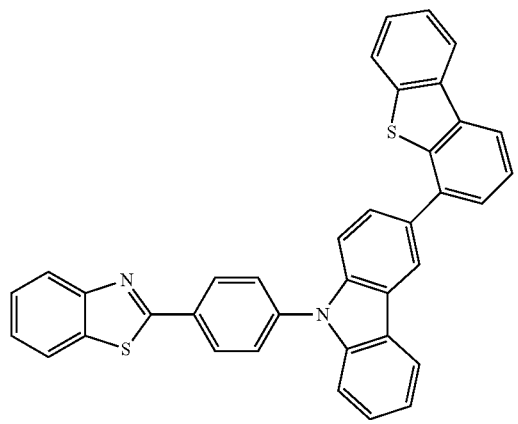
[Chemical Formula A-50]
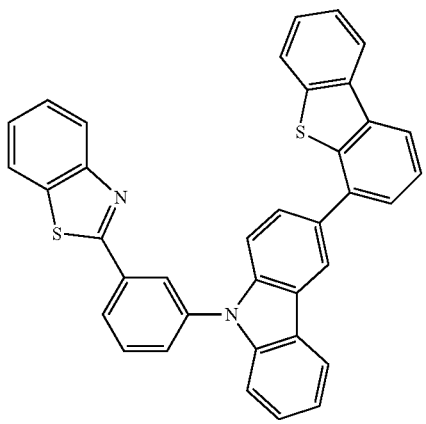
[Chemical Formula A-51]
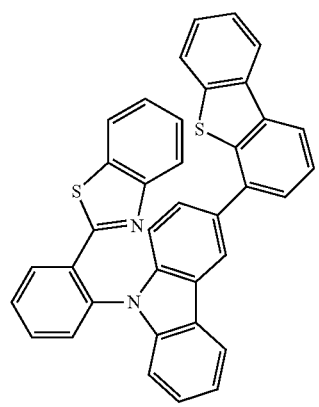
[Chemical Formula A-52]
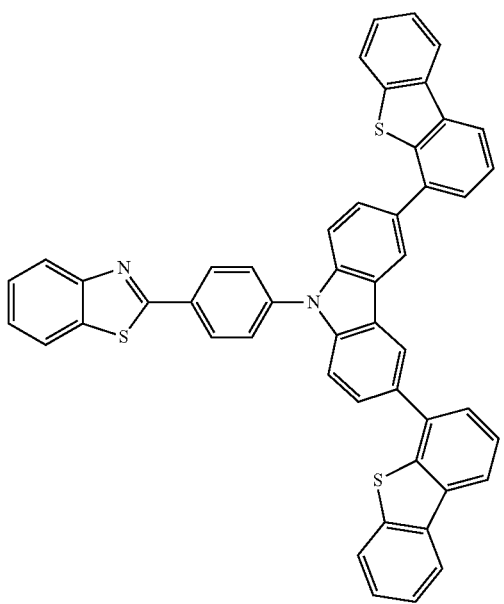

[Chemical Formula A-53]
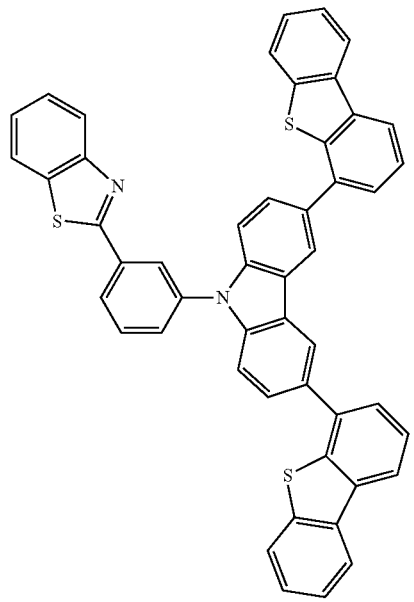
[Chemical Formula A-54]
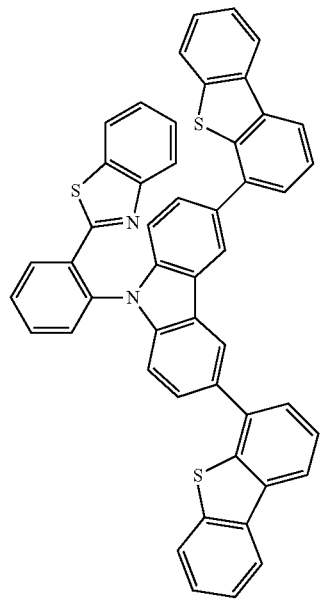
[Chemical Formula A-55]
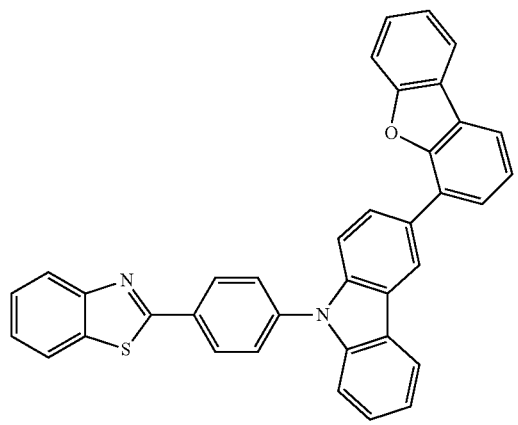
[Chemical Formula A-56]
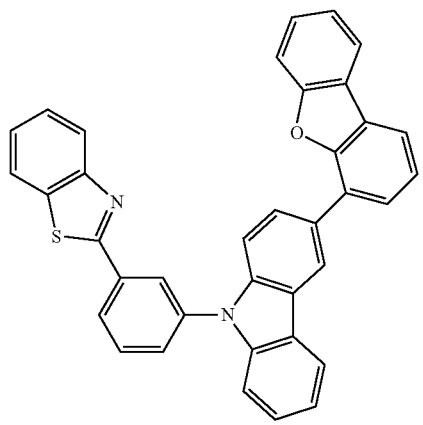
[Chemical Formula A-57]
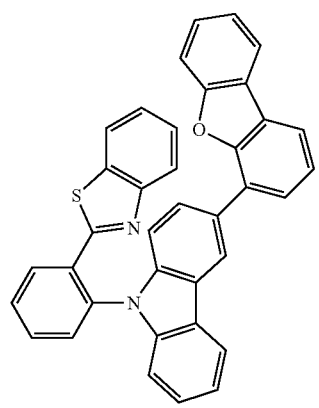
[Chemical Formula A-58]
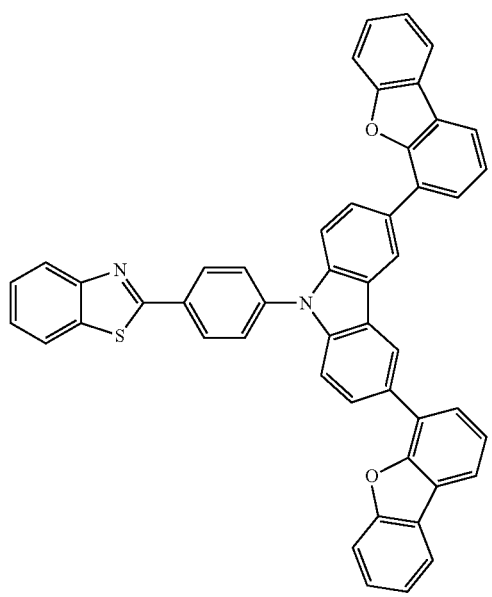

[Chemical Formula A-59]
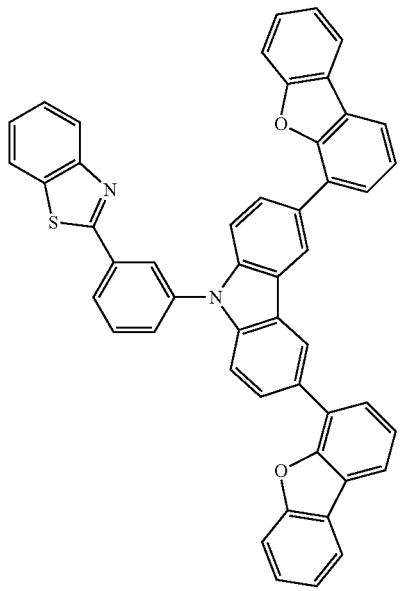
[Chemical Formula A-60]
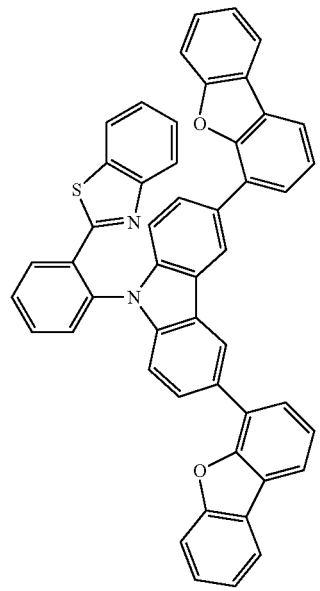
[Chemical Formula A-61]
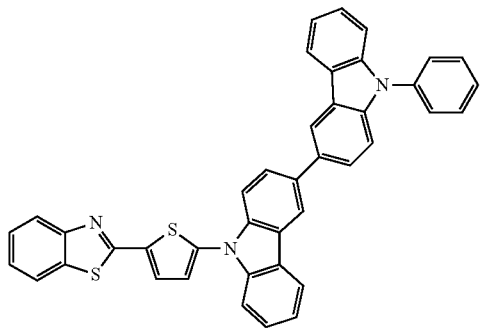
[Chemical Formula A-62]
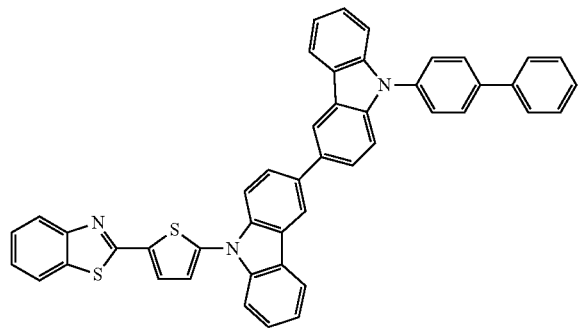
[Chemical Formula A-63]
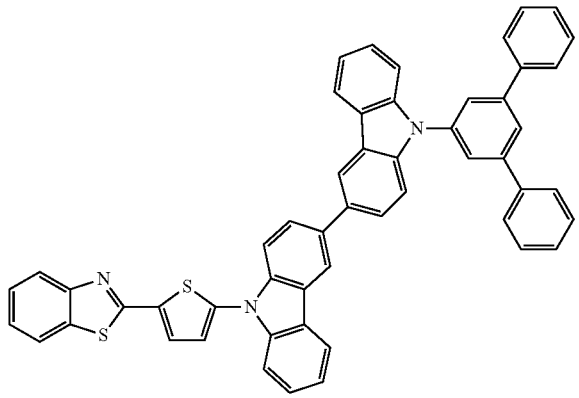
[Chemical Formula A-64]
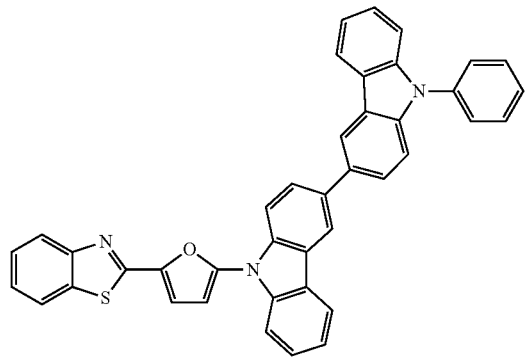

-continued
[Chemical Formula A-65]
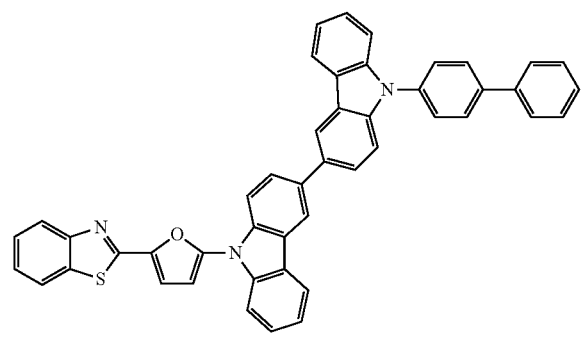
[Chemical Formula A-66]
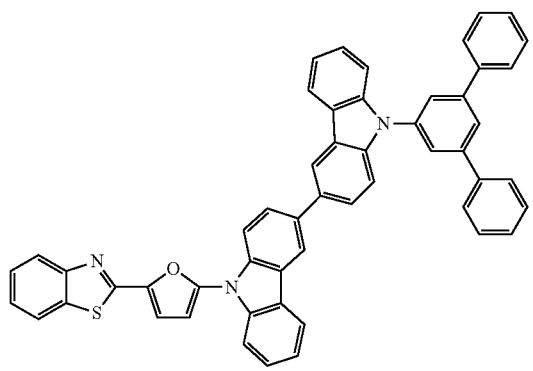
[Chemical Formula A-67]
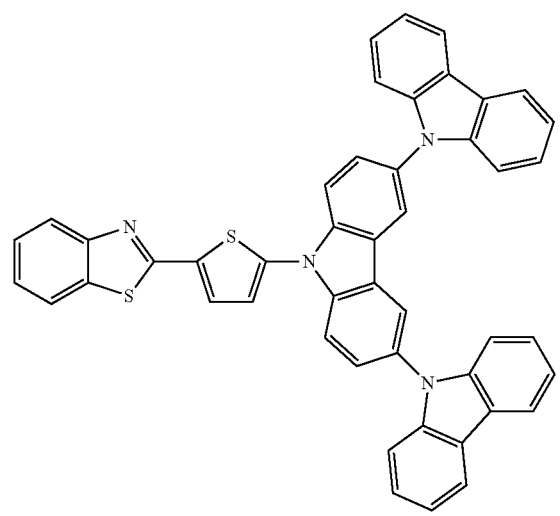
[Chemical Formula A-68]
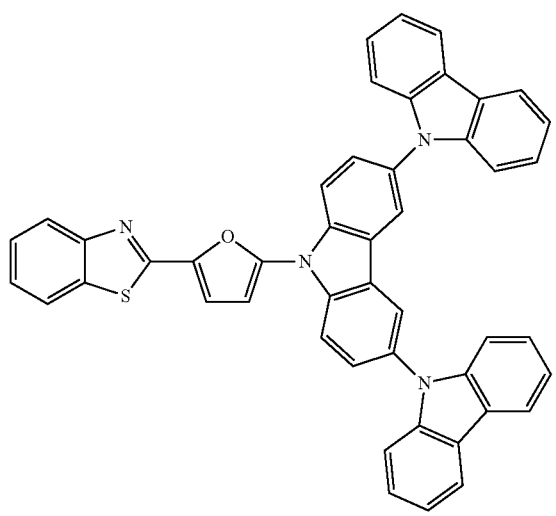
[Chemical Formula A-69]
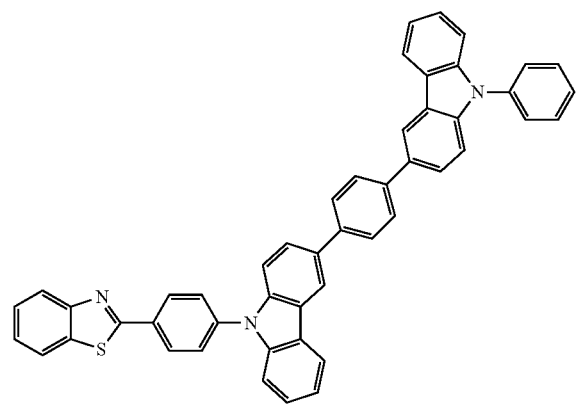
[Chemical Formula A-70]
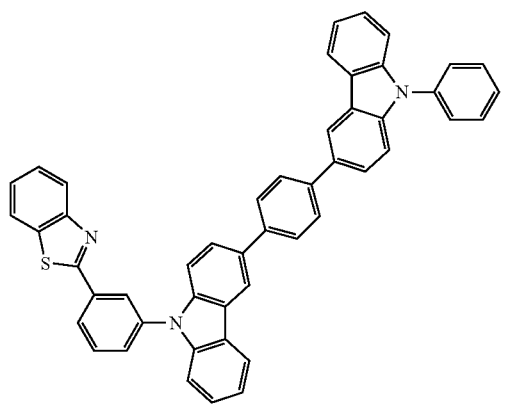

[Chemical Formula A-71]
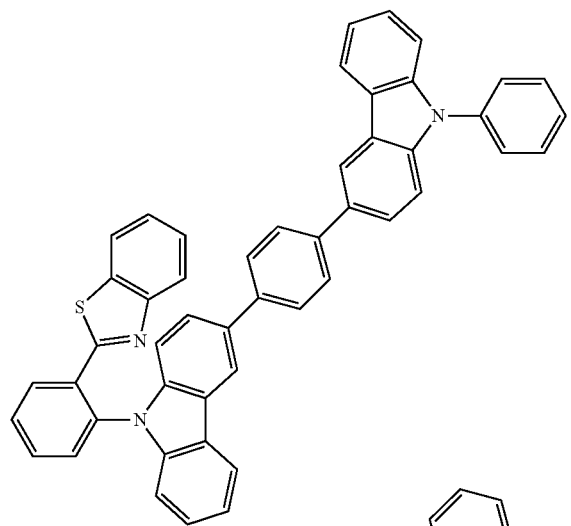
[Chemical Formula A-72]
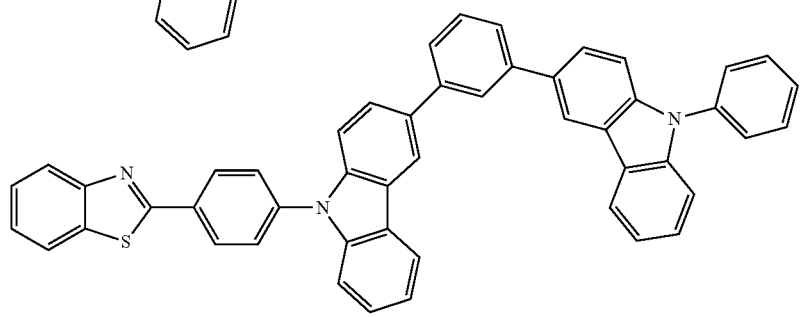
[Chemical Formula A-73]
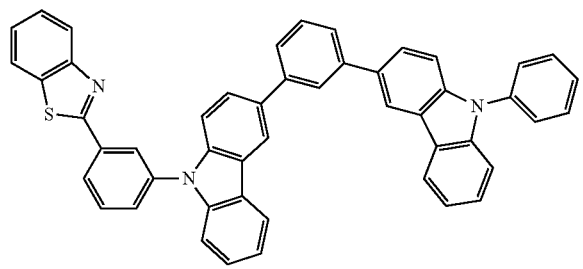
[Chemical Formula A-74]
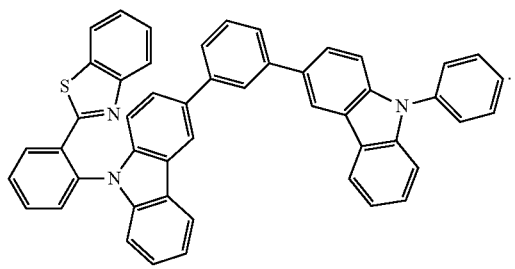
9. A compound for an organic optoelectronic device, wherein the compound for an organic optoelectronic device is one of compounds represented by the following Chemical Formulae B-1 to B-8:
[Chemical Formula B-1]
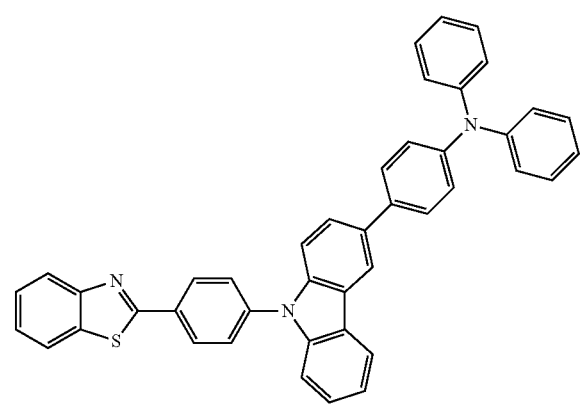
[Chemical Formula B-2]
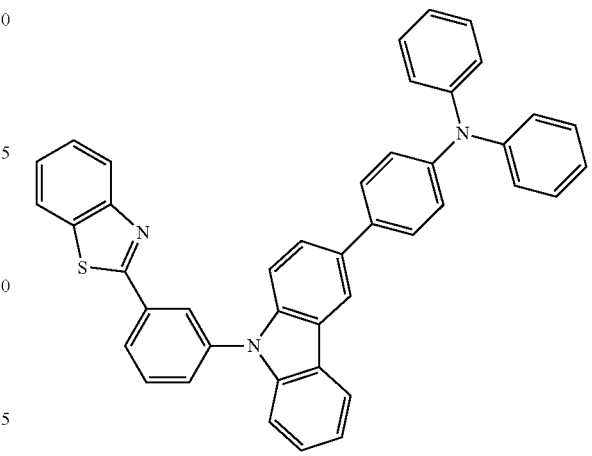

[Chemical Formula B-3]
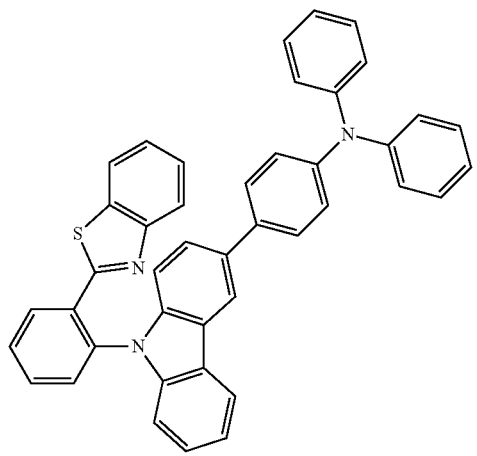
[Chemical Formula B-6]
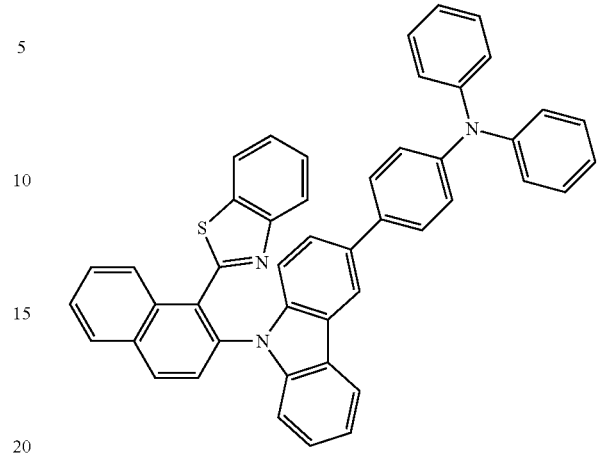
[Chemical Formula B-4]
[Chemical Formula B-7]
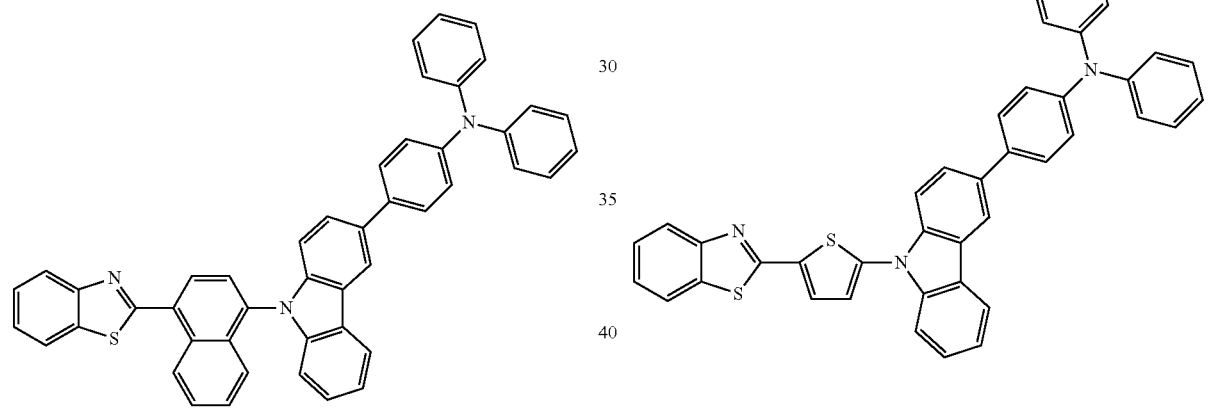
[Chemical Formula B-5]
[Chemical Formula B-8]
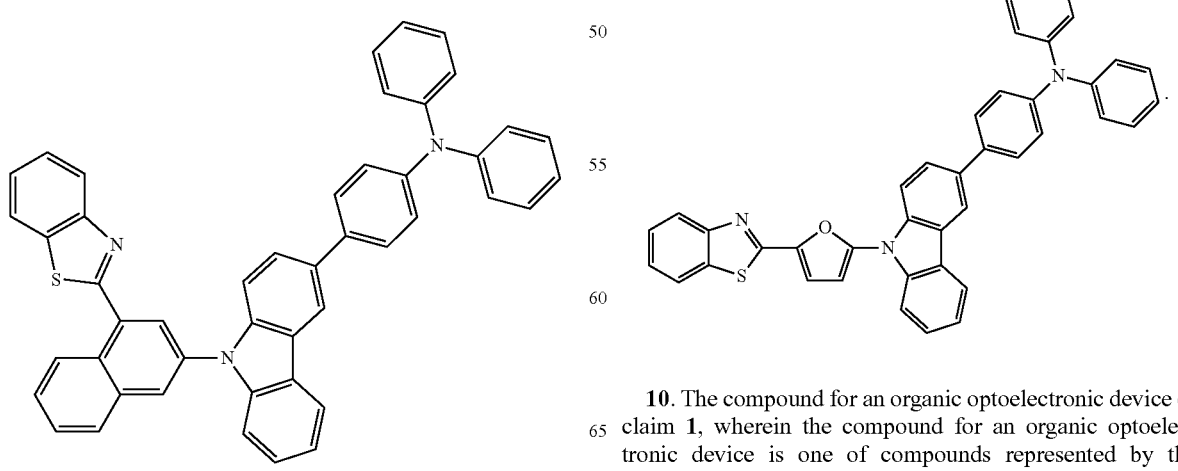
10. The compound for an organic optoelectronic device of claim 1, wherein the compound for an organic optoelectronic device is one of compounds represented by the following Chemical Formulae C-19 to C-45:

[Chemical Formula C-19]
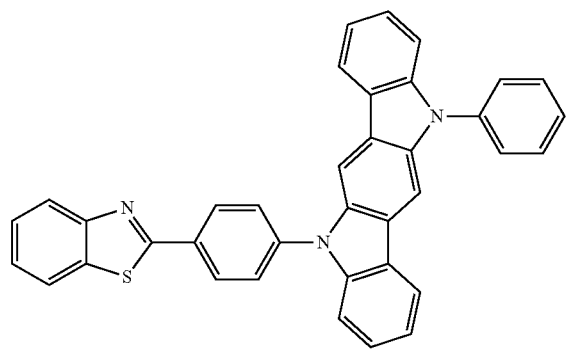
[Chemical Formula C-20]
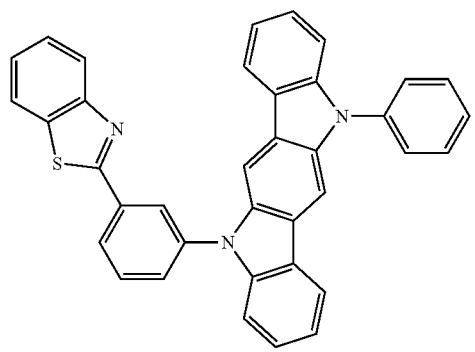
[Chemical Formula C-21]
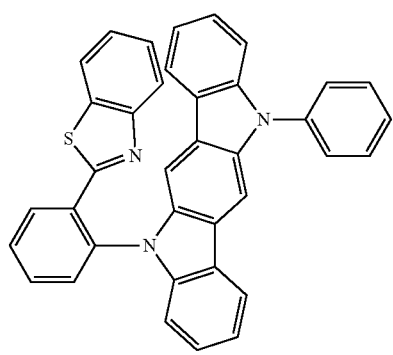
[Chemical Formula C-22]
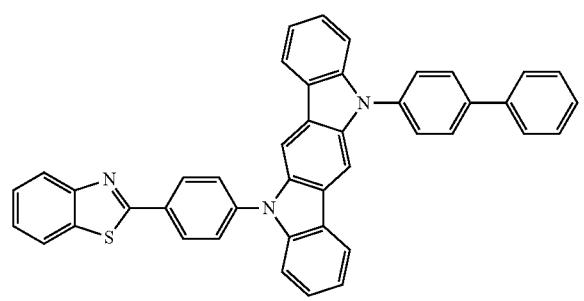
[Chemical Formula C-23]
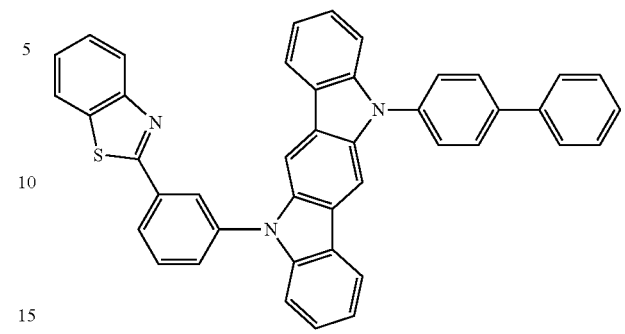
[Chemical Formula C-24]
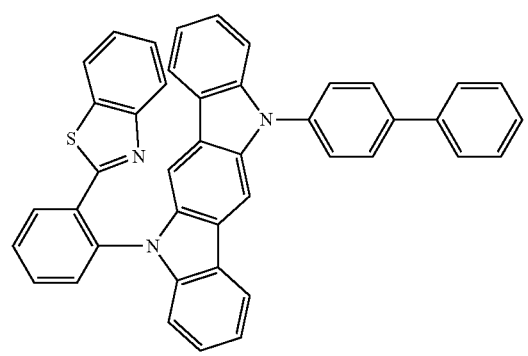
[Chemical Formula C-25]
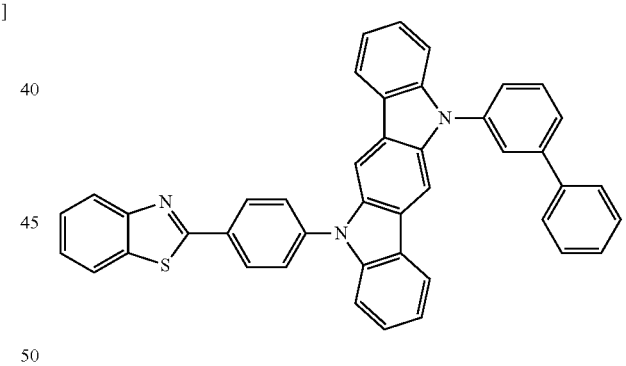
[Chemical Formula C-26]
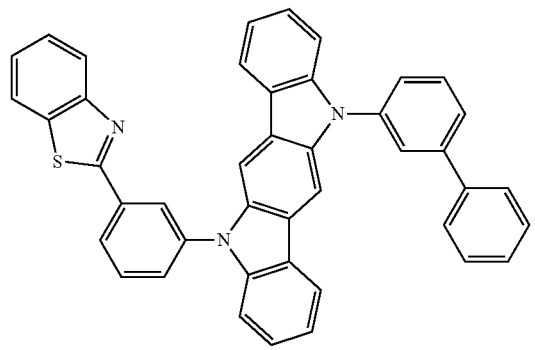

-continued
[Chemical Formula C-27]
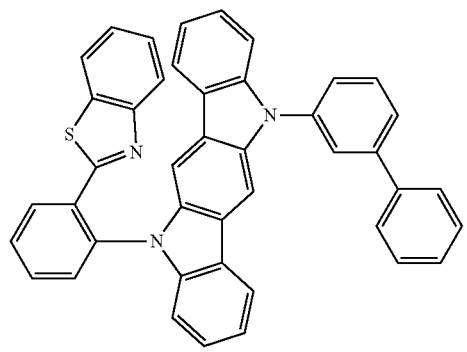
[Chemical Formula C-28]
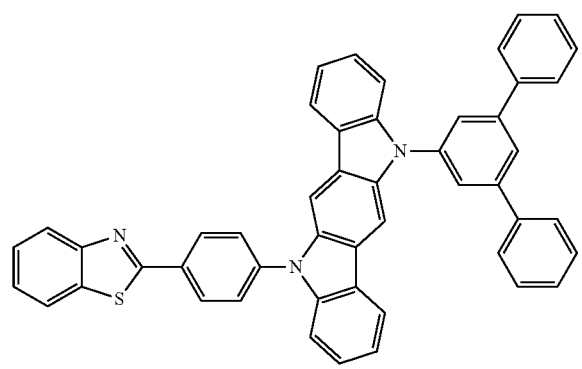
[Chemical Formula C-29]
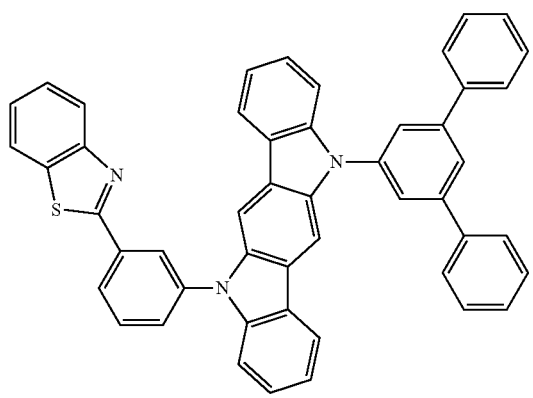
[Chemical Formula C-30]
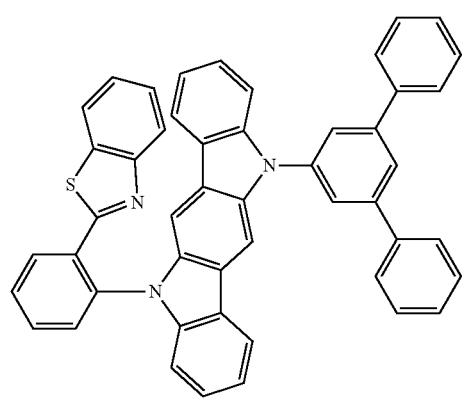
-continued
[Chemical Formula C-31]
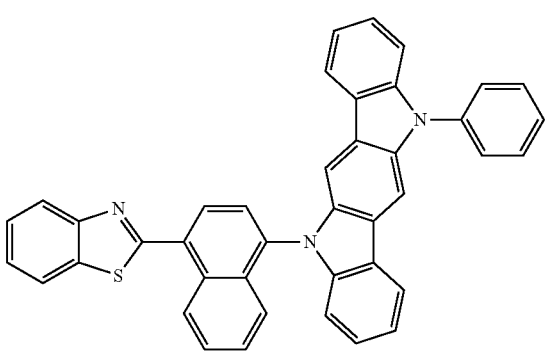
[Chemical Formula C-32]
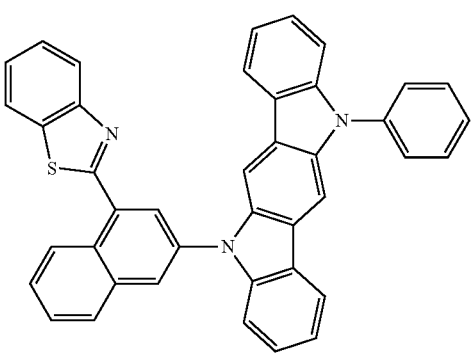
[Chemical Formula C-33]
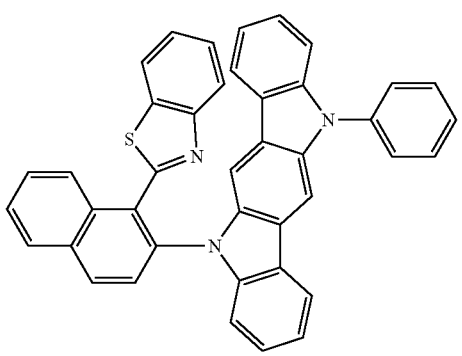
[Chemical Formula C-34]
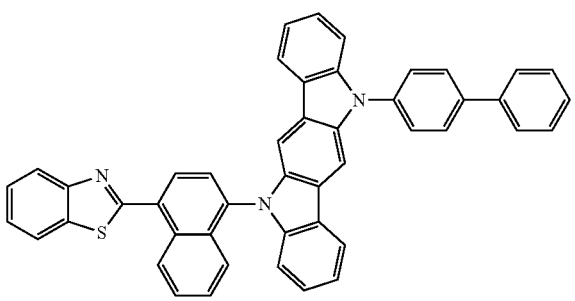

[Chemical Formula C-35]
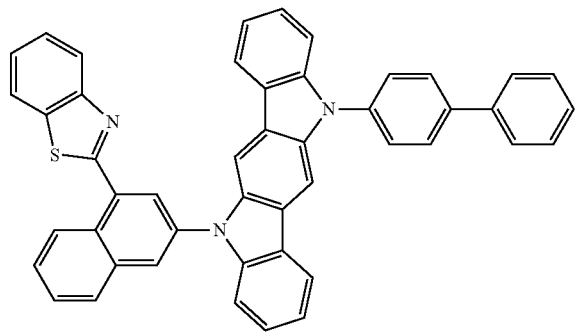
[Chemical Formula C-36]
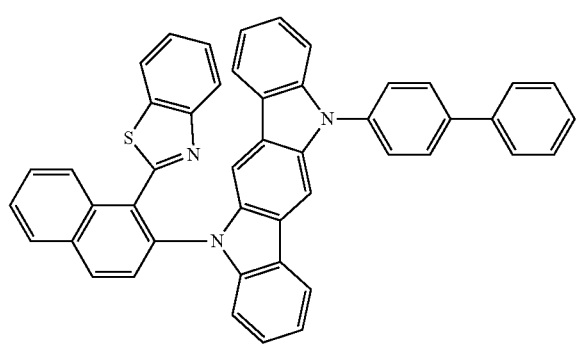
[Chemical Formula C-37]
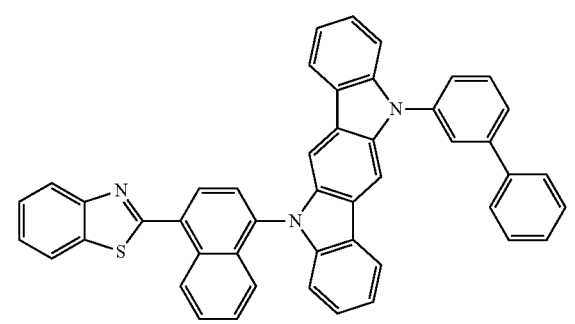
[Chemical Formula C-38]
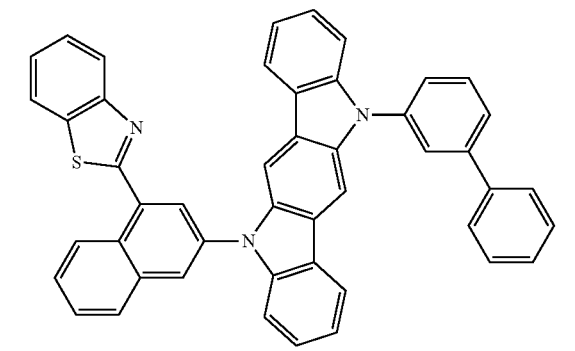
[Chemical Formula C-39]
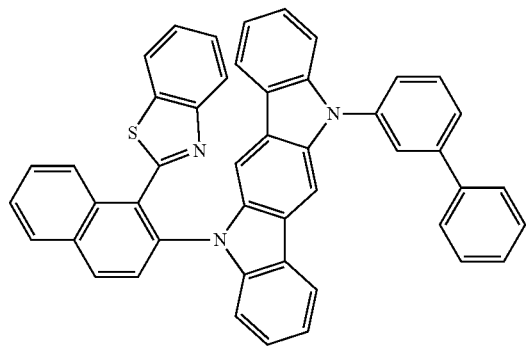
[Chemical Formula C-40]
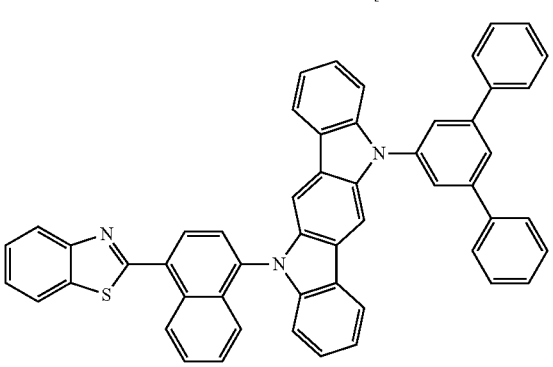
[Chemical Formula C-41]
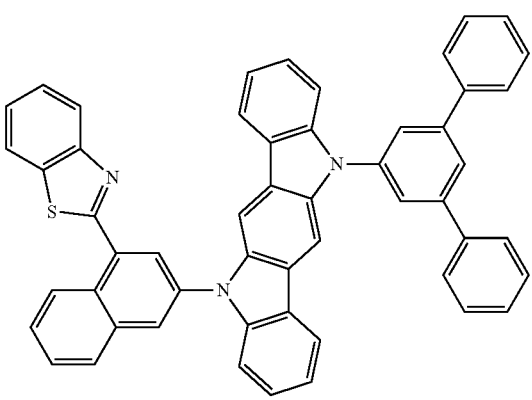
[Chemical Formula C-42]
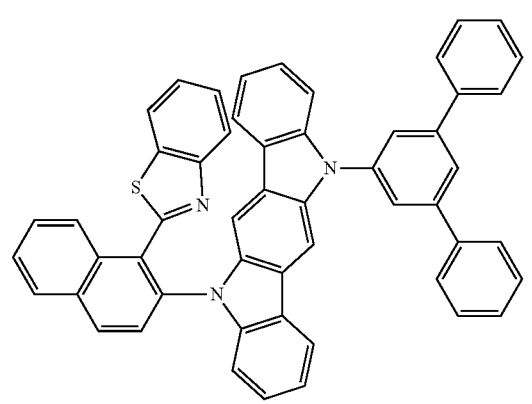

-continued
[Chemical Formula C-43]
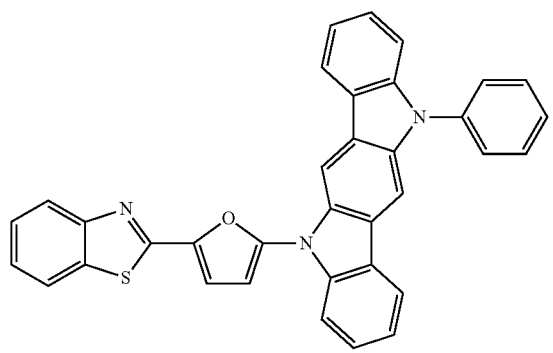
[Chemical Formula D-1]
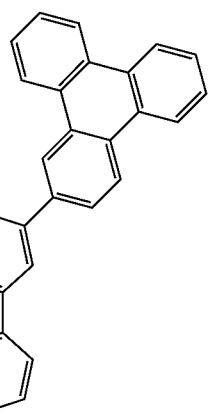
[Chemical Formula C-44]
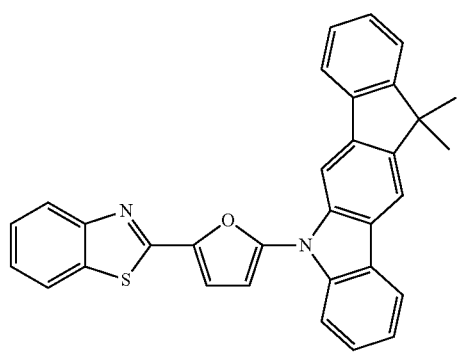
[Chemical Formula D-2]
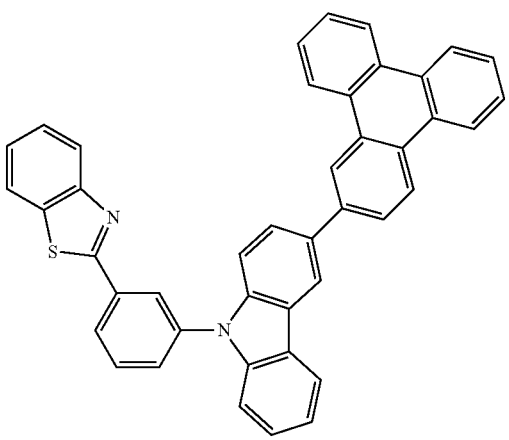
[Chemical Formula C-45]
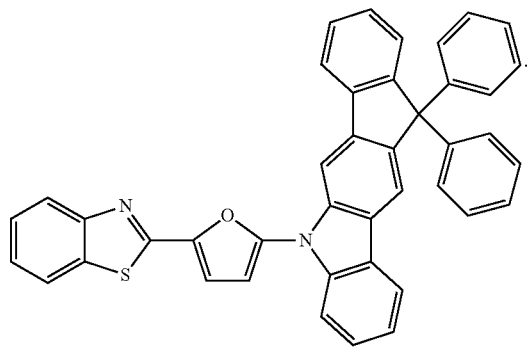
[Chemical Formula D-3]
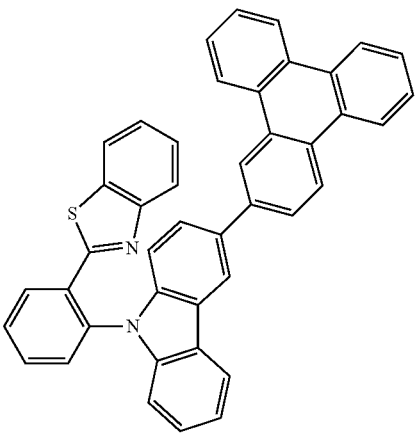
11. The compound for an organic optoelectronic device of claim 1, wherein the compound for an organic optoelectronic device is one of compounds represented by the following Chemical Formulae D-1 to D-8:

[Chemical Formula D-4]

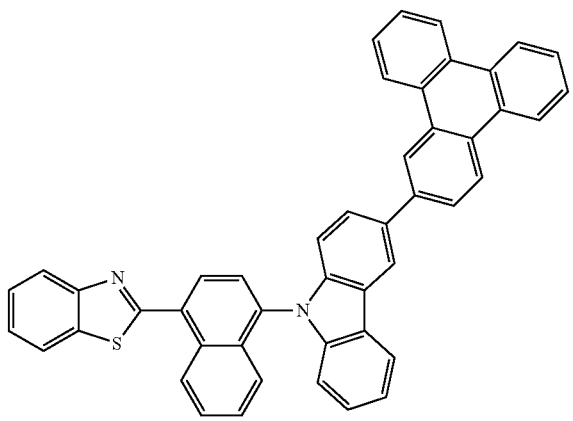

[Chemical Formula D-5]

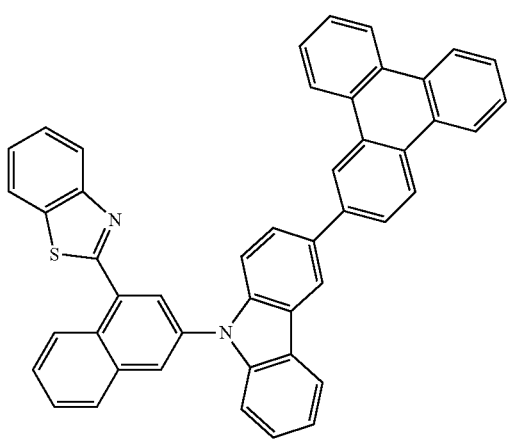

[Chemical Formula D-6]

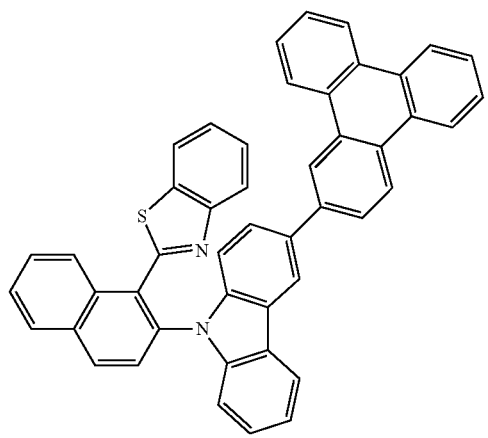

[Chemical Formula D-7]

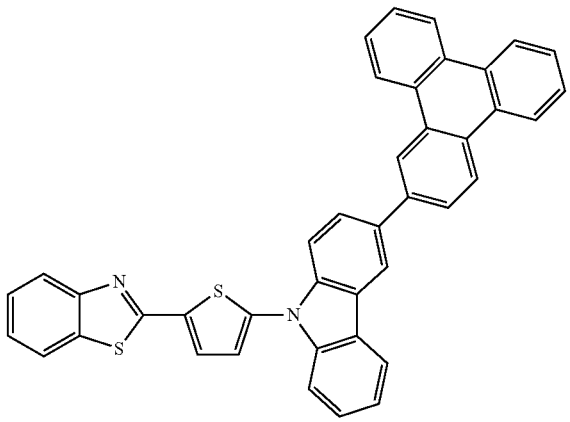

[Chemical Formula D-8]

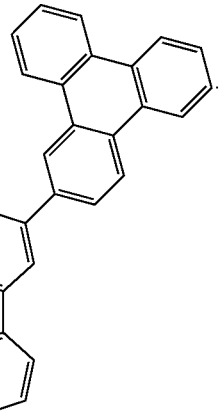

12. The compound for an organic optoelectronic device of claim 1, wherein the compound for an organic optoelectronic device has triplet exciton energy (T1) of greater than or equal to about 2.0 eV.

13. The compound for an organic optoelectronic device of claim 1, wherein the organic optoelectronic device is selected from an organic photoelectric device, an organic light emitting diode, an organic solar cell, an organic transistor, an organic photo-conductor drum, and an organic memory device.

14. An organic light emitting diode, comprising
an anode, a cathode, and at least one organic thin layer interposed between the anode and cathode,
wherein at least one of the organic thin layers comprises the above compound for an organic optoelectronic device of claim 1.

15. The organic light emitting diode of claim 14, wherein the organic thin layer is selected from an emission layer, a hole transport layer, a hole injection layer, an electron transport layer, an electron injection layer, a hole blocking layer, and a combination thereof.

16. The organic light emitting diode of claim 15, wherein the compound for an organic optoelectronic device is included in a hole transport layer (HTL) or a hole injection layer (HIL).

17. The organic light emitting diode of claim 15, wherein the compound for an organic optoelectronic device is included in an emission layer.

18. The organic light emitting diode of claim 17, wherein the compound for an organic optoelectronic device is used as a phosphorescent or fluorescent host material in an emission layer.

19. A display device comprising the above organic light emitting diode of claim 14.

* * * * *